United States Patent [19]
Petersen et al.

[11] Patent Number: 5,643,772
[45] Date of Patent: Jul. 1, 1997

[54] CRYPTOSPORIDIUM HYBRID VECTOR AND TRANSFORMED HOST CELLS

[75] Inventors: Carolyn Petersen, Berkeley; James Leech, Daly City; Richard C. Nelson, San Francisco; Jiri Gut, Novato, all of Calif.

[73] Assignee: The Regents of the University of California, Oakland, Calif.

[21] Appl. No.: 415,751

[22] Filed: Apr. 3, 1995

Related U.S. Application Data

[63] Continuation of Ser. No. 71,880, Jun. 1, 1993, abandoned, which is a continuation-in-part of Ser. No. 891,301, May 29, 1992, abandoned.

[51] Int. Cl.$^6$ .............................. C12N 15/00; C12N 1/20
[52] U.S. Cl. .................................... 435/172.3; 435/252.3; 536/23.7; 935/12
[58] Field of Search ...................... 536/23.7; 435/172.3, 435/252.3, 252.33, 320.1, 254.11, 240.2; 935/12

[56] References Cited

PUBLICATIONS

Doyle, P.S. et al. 1992. J. Cell. Biochem. Suppl. 16A, p. 146.
Reeves, C.D. et al. 1987. Gene vol. 52 pp. 257–266.
Dykstra, CC. et al. 1991. J. Protozool vol. 38(6) pp. 76S–78S (Abstract Only Provided).

Petersen, C., *The Mature erythrocyte surface antigen of Plasmodium falciparum is not required for knobs or cytoadherence*, Molecular and Biochemical Parasitology, 36:61–66, (1989).

Petersen, C., *The gene product of the Plasmodium falciparum 11.1 locus is a protein larger than one megadalton*, Molecular and biochemical Parasitology, 42:189–196, (1990).

Petersen, C., *Identification and Initial Characterization of Five Cryptosporidium parvum Sporozoite Antigen Genes*, Infection and Immunity, pp. 2343–2348, (Jun. 1992).

Petersen, C., *Characterization of a >900,000-$M_r$ Cryptosporidium parvum Sporozoite Glycoprotein Recognized by Protective Hyperimmune Bovine Colostral Immunoglobulin*, Infection and Immunity, pp. 5132–5138, (Dec. 1992).

Coppel, Ross, L., *Antibody Screening of Expression Libraries*, Methods in Molecular Biology, vol. 21: Protocols in Molecular Parasitology, Chapter 21, pp. 277–296, (1993).

Primary Examiner—James C. Housel
Assistant Examiner—Ginny Allen Portner
Attorney, Agent, or Firm—Hana Verny

[57] ABSTRACT

The invention comprises a Cryptosporidium hybrid vector comprising a regulatory DNA segment operably coupled to a DNA fragment encoding a polypeptide to which anti-Cryptosporidium antibodies specifically bind and transformed host cells comprising the hybrid vectors.

4 Claims, 4 Drawing Sheets

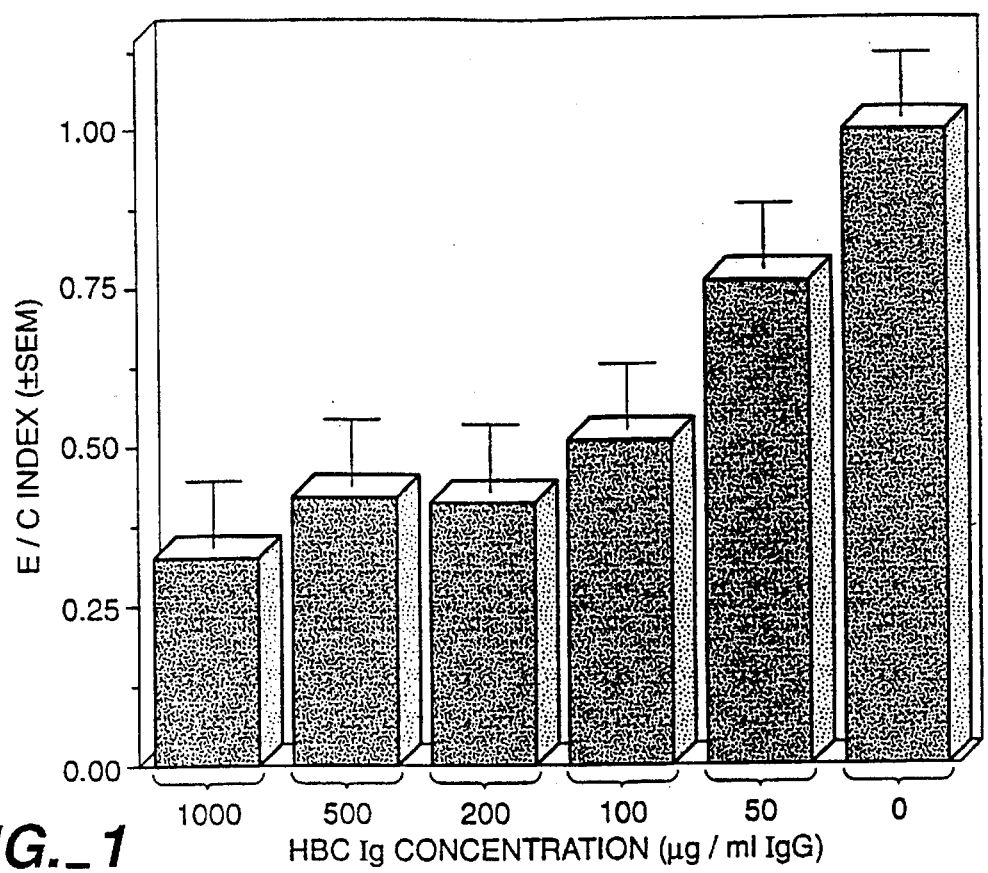
FIG._1
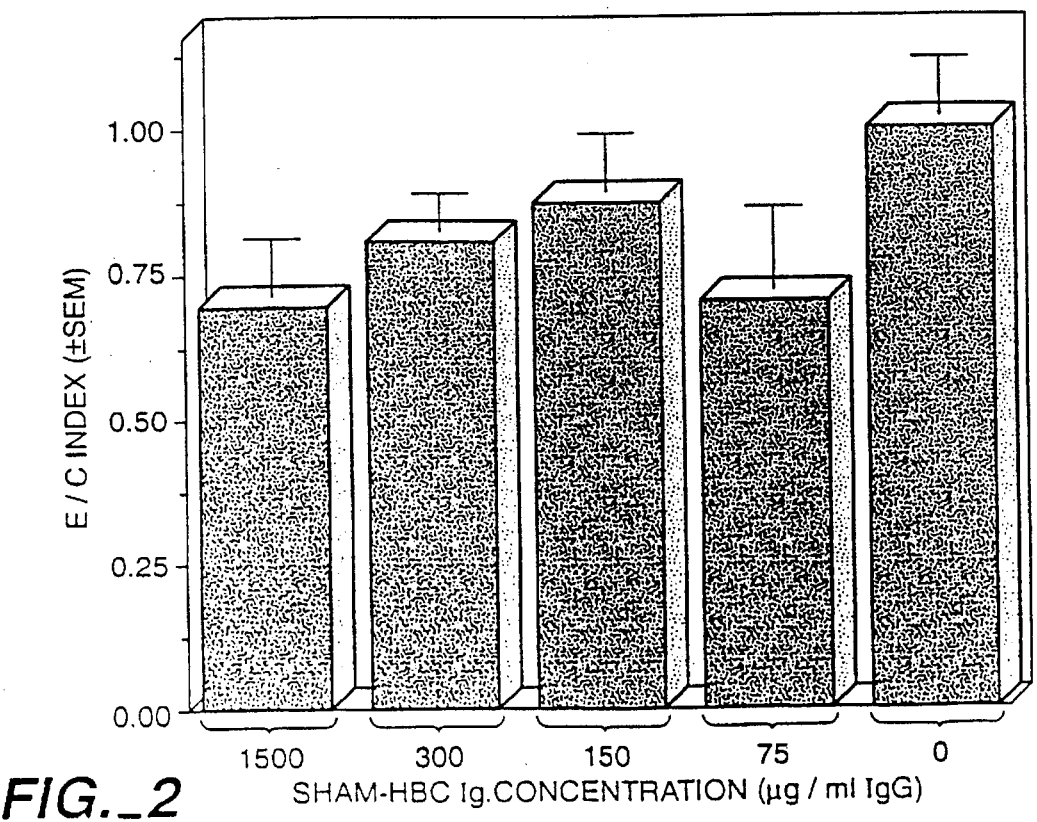
FIG._2

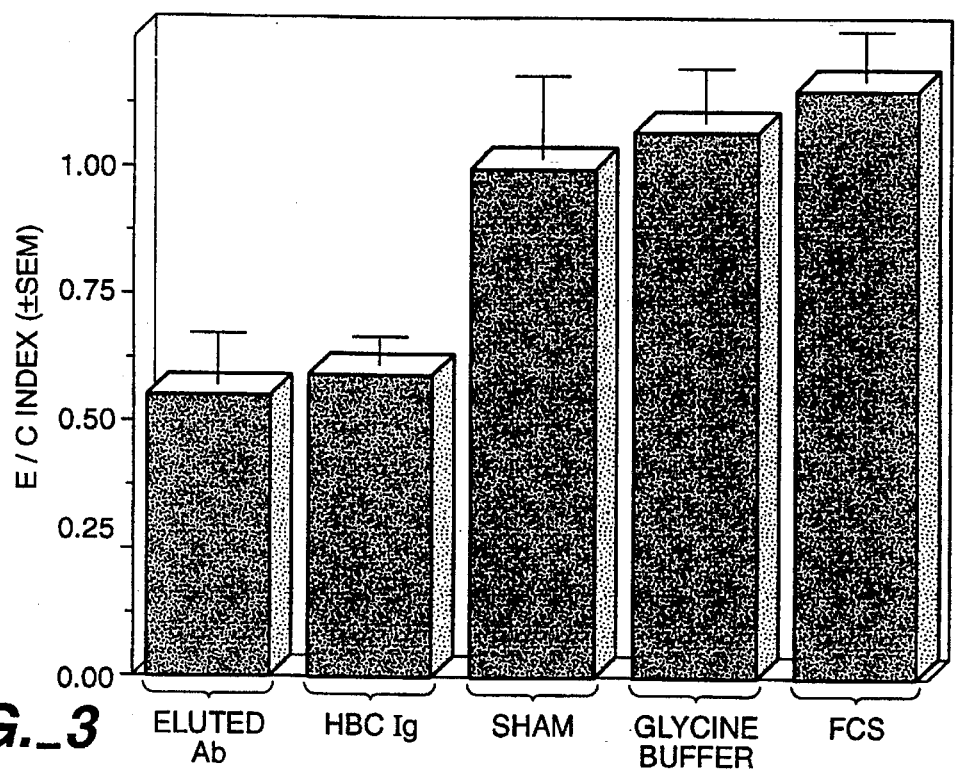
FIG._3
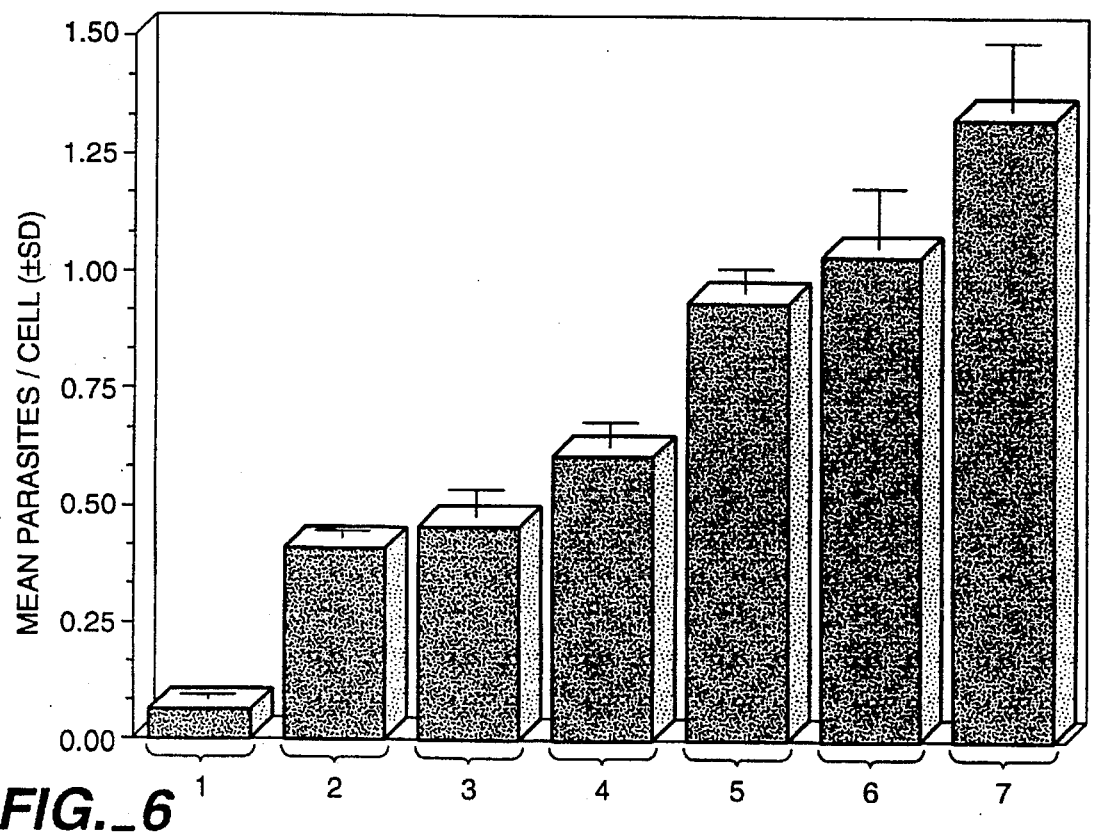
FIG._6

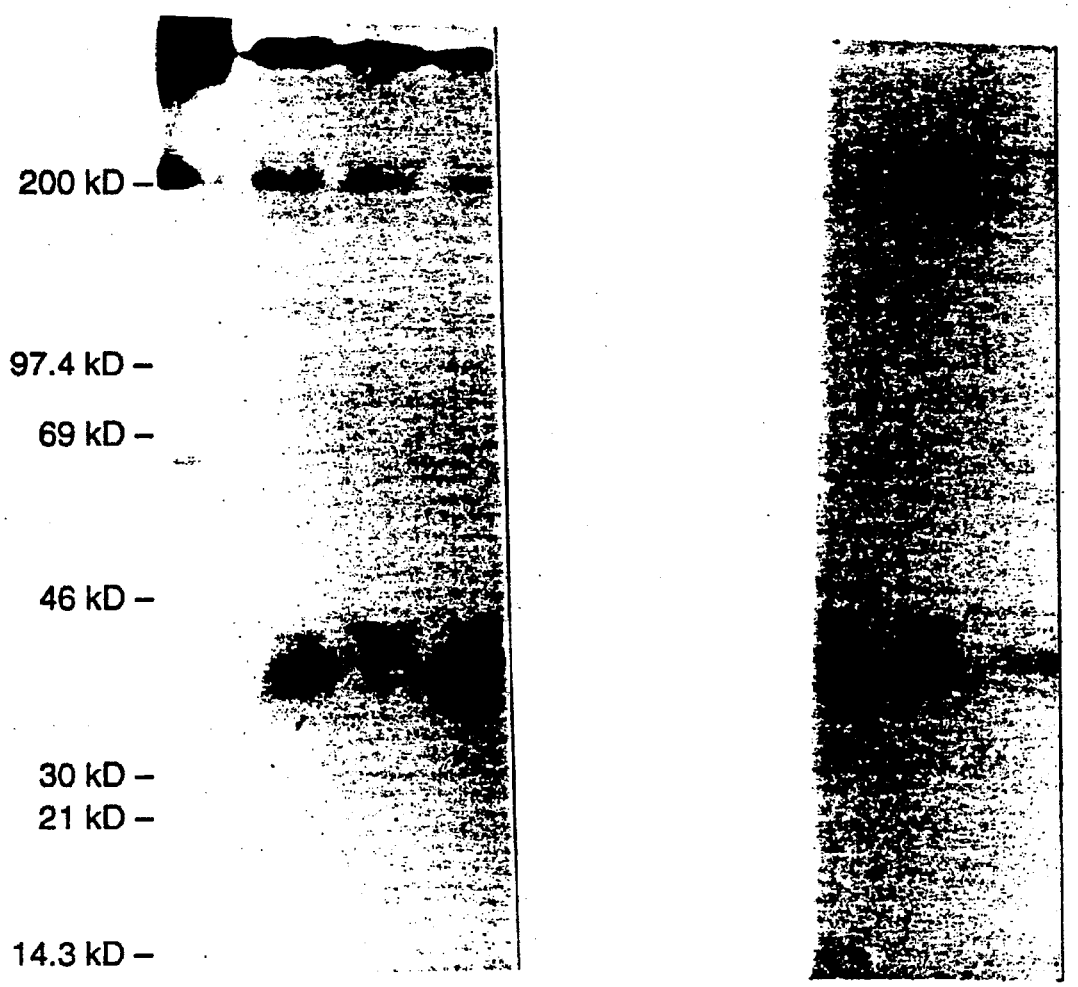
FIG._4

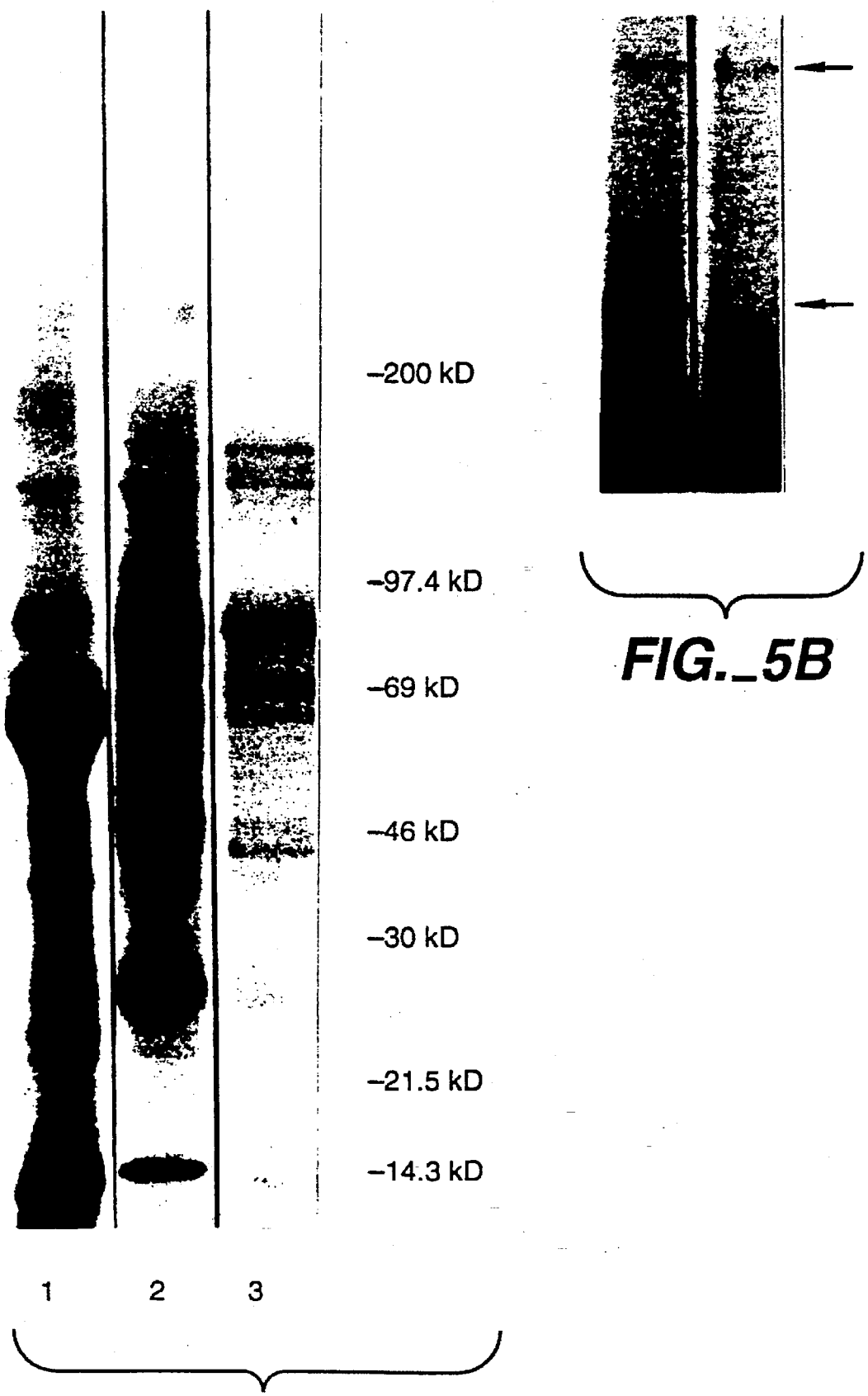
FIG._5B
FIG._5A

CRYPTOSPORIDIUM HYBRID VECTOR AND TRANSFORMED HOST CELLS

BACKGROUND OF THE INVENTION

This is a continuation of application of Ser. No. 08/071,880 filed on Jun. 1, 1993, now abandoned, which is a continuation-in-part of Ser. No. 07/891,301 filed on May 29, 1992 now abandoned.

This invention was developed at least partially with U.S. Government support under National Institutes of Health Grant Nos. AI-29882 and R43 AI 30295-01A1. The U.S. Government may have certain rights in this invention.

FIELD OF THE INVENTION

This invention relates to a novel polypeptide comprising an amino acid sequence capable of specifically binding antibodies raised against the protozoan pathogen Cryptosporidium spp. (Cryptosporidium). This invention also relates to DNA and RNA segments which encode such polypeptides. These polypeptides bind antibodies that afford protection against, ameliorate symptoms of, and accelerate recovery from, infection by this pathogen. These polypeptides may be produced from DNA or RNA sequences encoding them, and they may be used for the immunization of humans or animals against infection by Cryptosporidium. These polypeptides may also be used for the production of antibodies suitable to counter Cryptosporidium infection. Finally, this invention relates to the use of these polypeptides and antibodies raised against them in diagnosing infection by Cryptosporidium and diagnostic kits.

DESCRIPTION OF THE BACKGROUND

Cryptosporidium are parasitic agents causing infection in a wide variety of animals including birds, reptiles and mammals. *C. parvum* is believed to be the major cause of disease in humans and domestic animals. The disease is acute and self-limited in immunocompetent humans. It, however, causes a more severe and potentially lethal disease in persons affected with AIDS. In spite of the morbidity of cryptosporidiosis in AIDS patients, no effective immunotherapy or chemotherapy is available at the present time to counter this disease. Moreover, the understanding of the biology and biochemistry of Cryptosporidium, as well as the pathophysiology of cryptosporidiosis is still at an early stage.

*C. parvum* has been classified based on its ultrastructural features as a member of the phylum Apicomplexa. "Zoites" such as sporozoites, merozoites, and tachyzoites are the invasive stages of the Apicomplexa. The zoites are extracellular and have a unique trilaminar membrane, called the pellicle, which appears to mediate the attachment of the parasite to the host cell membrane. The pellicle is associated with subpellicular structures that are involved in motility. The zoites also share an anterior apical complex composed of specialized secretory organelles (rhoptries, micronemes and dense granules). These organelles secrete products which appear to facilitate the entry of the zoite into the host cell and the generation of the parasitophorous vacuole.

The *C. parvum* infection is initiated by the ingestion of oocysts, the excystation of oocysts with release of sporozoites and the invasion of gut epithelial cells by sporozoites. Thereafter, the intracellular forms mature and release new daughter merozoites which reinvade the gut epithelial cells. *C. parvum* also has a sexual cycle. The sexual cycle of *C. parvum* also occurs in the gut and results in the production of sporulated oocysts, some of which may excyst before being shed. In persistent infection of an immunocompromised host, both the merozoite and the endogenously produced sporozoite may contribute to the ongoing invasion by *C. parvum*. The relative contribution of each stage, however, remains unclear.

Sporozoites and merozoites are the only stages of *C. parvum* which are free in the gut and, therefore, accessible to neutralization by luminal antibody. In other Apicomplexan zoites, e.g., Plasmodium, Eimeria, and Toxoplasma, the pellicle and apicle complex proteins are targets of invasion-inhibiting antibodies in vitro, and neutralization antibodies in vivo. Polypeptides localized in the pellicles and apicle complex of *C. parvum* zoites are likely targets of endogenous host immune responses. To date, the most promising treatment for cryptosporidiosis or infection by *C. parvum*, is the passive oral transfer of anti-*C. parvum* hyperimmune bovine colostral immunoglobulin (HBC Ig). HBC Ig has been shown to react with numerous oocyst and sporozoite proteins on Western blots and to be therapeutic in neonatal mice. Whole hyperimmune bovine colostrum (HBC) has also been reported to inhibit infection by *C. parvum*. Duodenal infusions of HBC have been reported to ameliorate *C. parvum* infection in AIDS or other immunocompromised patients.

GP15, GP20 and P23 are examples of sporozoite proteins or glycoproteins which are exposed on the surface of *C. parvum*. These antigens are examples of targets of monoclonal antibodies raised against the corresponding oocysts/sporozoites. These monoclonal antibodies have been shown to prevent or attenuate infection in studies using animals challenged with *C. parvum*. Monoclonal antibodies such as 17.41 and 18.44 have been reported to partially protect mice from *C. parvum* infection, although the sizes of the target antigens are still unclear. Monoclonal antibody 18.44 recognizes a non-peptide antigen. In some instances, the epitope recognized by the monoclonal antibodies has been found in both sporozoites and merozoites.

Thus, there is still a need for agents useful for the immunotherapy of cryptosporidiosis in both uncompromised and immunocompromised subjects, e.g. AIDS, patients, which would prevent or limit the disease's manifestations. There is also still a need for an agent useful for the detection of ongoing *C. parvum* invasion, particularly in its early stages.

SUMMARY OF THE INVENTION

This invention relates to a biologically pure polypeptide comprising a biologically pure, isolated peptide capable of selectively and specifically binding to anti-Cryptosporidium antibodies.

This invention also relates to biologically pure DNA and RNA segments that encode the polypeptides described above.

Also part of this invention is a fusion protein comprising one of the polypeptides described above and a second unrelated polypeptide expressed by a regulatory DNA segment operably coupled to the DNA segment described above that encodes the polypeptide of this invention. Still part of this invention are fusion RNA and DNA polymers comprising the RNA or DNA of this invention and a second unrelated polyRNA or polyDNA segment.

In addition, this invention comprises a hybrid vector comprising the DNA segment described above operatively coupled thereto, and a hybrid eukaryotic or prokaryotic host carrying the hybrid vector of this invention.

This invention also relates to a method of retarding, inhibiting, or countering Cryptosporidium infection of a subject's cells comprising administering to a subject in need of such treatment an amount of an anti-Cryptosporidium antibody effective to retard the invasion by and/or development of Cryptosporidium of the subject's cells.

Also provided herein is a method of retarding, inhibiting or countering C. parvum infection of a subject's cells comprising administering to a subject in need of such treatment an amount of one of the polypeptide of this invention capable of eliciting from the subject a cell invasion and/or development inhibitory amount of anti-C. parvum antibodies.

In addition, this invention comprises a method of diagnosing Cryptosporidium infection of a subject, comprising contacting a body substance obtained from the subject with an anti-Cryptosporidium antibody; and detecting any selective binding of the antibody to any antigenic Cryptosporidium peptide present in the body substance.

This invention, in addition to the above, also encompasses a method of diagnosing Cryptosporidium infection of a subject, comprising contacting a body fluid obtained from the subject with the polypeptide of this invention; and detecting any selective binding of the polypeptide to any anti-Cryptosporidium antibodies in the body fluid.

Also part of this invention is a Cryptosporidium diagnostic kit, comprising anti-Cryptosporidium specific antibodies; and instructions for the use of the kit.

Furthermore, this invention also provides a Cryptosporidium infection diagnostic kit, comprising the polypeptide of this invention; and instructions for use of the kit.

A more complete appreciation of the invention and many of the attendant advantages thereof will be readily perceived as the same becomes better understood by reference to the following drawings.

BRIEF DESCRIPTION OF THE DRAWINGS

FIG. 1 depicts the inhibition of Cryptosporidium infection of epithelial cells by HBC Ig. 100–1000 µg/ml IgG resulted in a significant reduction (p<0.01) in the mean number of intracellular parasites/MDCK (Madin-Darby canine kidney) cell of up to 61% relative to fetal calf serum (FCS) and of up to 55% relative to sham HBC (SHAM-HBC) Ig controls, while no inhibition was observed at lower HBC Ig concentrations ($\leq$50 µg/ml IgG).

FIG. 2 depicts the effect of SHAM-HBC Ig on C. parvum infection of MDCK cells. No significant inhibition was observed for SHAM-HBC Ig at concentrations ranging from 1500 µg/ml to 75 µg/ml IgG with respect to FCS controls (p<0.01).

FIG. 3 depicts the results of another specific anti-Cryptosporidium antibody assay. HBC Ig antibodies (50–100 µg/ml IgG) eluted from C. parvum Western blots were utilized in a MDCK in vitro assay. The experimental data were normalized to SHAM-HBC IgG controls (75 µg/ml IgG). Significant inhibition of Cryptosporidium infectivity was observed for cultures treated with anti-Cryptosporidium Ab eluted from Western blot (Eluted Ab) and HBC Ig (100 µg/ml IgG) (HBC Ig) with respect to SHAM-HBC Ig (100 µg/ml IgG) (SHAM), glycine buffer and FCS controls (p<0.01).

FIG. 4 shows a Western Blot of C. parvum proteins developed with HBC Ig or SHAM-HBC Ig. Oocyst/sporozoite proteins were either blotted (lane 1) or immunoprecipitated with HBC Ig at dilutions 1/1,000 (lane 2), 1/5,000 (lane 3), and 1/10,000 (lane 4) and with SHAM-HBC Ig at the same dilutions as above (lanes 5–7). After electrophoresis, Western blots were developed with HBC Ig (lanes 1–4) or SHAM-HBC Ig (lanes 5–7) followed by [$^{125}$I]-Protein G, and autoradiographed.

FIG. 5(A)—Surface proteins of C. parvum sporozoites recognized by HBC Ig. Radioiodinated sporozoites were disrupted, and an aliquot of the membrane proteins was directly resuspended in SB and electrophoresed (lane 1). Alternatively, radiolabeled sporozoite membranes were SDS solubilized (lane 2) or Triton X-100 solubilized (lane 3) prior to immunoprecipitation with affinity bound HBC Ig. Proteins were resolved by SDS-PAGE, and autoradiographed for 8 hrs.

FIG. 5(B)—Detail of autoradiogram of lanes 2 and 3 exposed for 24 hrs. The >900 kD and about 250 kD apparent molecular weight (app. MW) molecules are indicated by arrows.

FIG. 6 depicts the in vitro inhibition of C. parvum infectivity by antibodies raised against the recombinantly obtained proteins encoded by S19, S34 and S2 Crytosporidium clones. Col. 1: anti-S19 ascites (dilution 1/20). Col. 2: anti-S34 ascites (dilution 1/20). Col. 3: anti-S2 ascites (dilution 1/20). Col. 4: HBC Ig (dilution 1/100). Col. 5: anti-GP900 ascites (dilution 1/20). Col. 6: SHAM-HBC Ig (dilution 1/100). Col. 7: FCS control.

Other objects, advantages and features of the present invention will become apparent to those skilled in the art from the following discussion.

DESCRIPTION OF THE PREFERRED EMBODIMENTS

This invention arose from a desire by the inventors to provide novel compositions suitable for therapeutic use in C. parvum infection, such as the active and passive immunotherapy of C. parvum infected subjects or to ameliorate symptoms produced by infection of the parasite. The polypeptides of this invention are also useful for the early detection of Cryptosporidium infection. The inventors targeted the protein components of the parasite for their work. Protein extracts of C. parvum were screened for polypeptide components evidencing specific binding to antibodies raised against the parasite. In order to isolate the DNA encoding such polypeptides, viral DNA expression libraries were constructed and then screened with polyclonal anti-C. parvum antibodies reactive with sporozoites and oocysts of the parasite. A large number of colonies were screened. The number of clones was significantly reduced when only those clones (57) that positively bound to the specific antibodies were kept. The antibodies binding to the polypeptides produced by the 57 clones were then purified by elution from the lawns containing the colonies, and employed to help to determine the apparent molecular weights (app. MW) of the different polypeptides of the parasite. These purified antibodies were also used to determine the location of endogenous immunofluorescent antigens (IFA) in the intact C. parvum organism.

A number of clones were identified and eventually segregated into distinct immunogenic C. parvum groups. Five of these distinct groups of polypeptides were then localized by IFA to the sporozoite pellicle and apical complex regions of the C. parvum organism, and the apparent molecular weights of the endogenous polypeptides were determined.

The above approach relying on the isolation of anti-C. parvum antibodies recognizing the cloned polypeptides afford advantages over a monoclonal antibody (MAb) approach. The antibodies utilized by the inventors are typically polyclonal antibodies that recognize multiple epitopes on the target polypeptide. The monoclonal antibodies elicited by the GP900 protein are monoepitopic, and carbohydrate specific, which renders them ineffective for screening a cDNA library. Moreover, in the present method, large amounts of recombinant polypeptide may be produced to, in turn, obtain a corresponding large quantity of polyclonal antibodies or to make the antibodies in animals. Furthermore, once polyclonal eluted antibodies recognizing the antigen of interest have been identified, the corresponding genes, by definition, are in hand for further analysis and use.

This invention provides a biologically pure polypeptide comprising a biologically pure, isolated peptide capable of specifically binding to anti-C. parvum antibodies, and optionally a second unrelated polypeptide to form a fusion protein.

The binding of the present peptides may be attained by contacting the peptide for each clone provided herein with polyclonal antibodies raised against Cryptosporidium or with monoclonal antibodies obtained by the fusion of, e.g., a myeloma cell line with an anti-Cryptosporidium antibody producing lymphocyte. The binding of the peptide in the biologically pure peptide to the antibodies may be determined by detection with anti-immunoglobulin antibodies conjugated to an indicator moiety which can be detected after development with a colorometric reagent, among other methods. For example, nitrocellulose membranes containing the biologically pure polypeptide may be incubated with the antibodies, washed, and then incubated with goat anti-mouse IgG conjugated to alkaline phosphatase (Promega) prior to development with, e.g., the colorometric reagents nitroblue tetrazolium and 5-bromo-4-chloro-3-indoyl phosphate. Alternatively, the indicator moiety may be radiolabeled, e.g., $^{125}$I labeled protein A, which binds to the antibodies. The detection in this instance is by exposure to radiographic film (see, e.g., Example 12).

In one preferred embodiment, the peptide in the polypeptide is capable of binding to a subgroup of antibodies that selectively bind the S34 polypeptide from C. parvum, polypetpides of clones encoding other peptides encompassed by the >900 kD app. MW protein or fusion proteins from clones that hybridize to the >900 kD app. MW DNA insert. All molecular wirghts reported in this patent were obtained by denaturing electrophoresis with BIS-polyacrylamide gels, unless otherwise specified. This subgroup of antibodies is capable of binding the >900 kD app. MW peptide from C. parvum, and they may be obtained by challenging an animal with C. parvum as shown in the examples. This subgroup of antibodies may be isolated from a mixture of polyclonal antibodies, as shown in the examples or by elution from the colonies that they bind to, after a polypeptide of a given specificity is produced by recombinant DNA technology, as also shown in the examples. These antibodies also specifically bind the S34 polypeptide, other peptides encompassed by the >900 kD app. MW protein, and fusion proteins thereof. Polypeptides other than the S34 polypeptide may be obtained by screening a C. parvum DNA library(ies) with the S34 DNA and monoclonal and polyclonal antibodies. In a preferred embodiment, the peptide in the polypeptide comprises a glycopeptide of app. MW >900 kD. This glycopeptide corresponds to at least a portion of the endogenous antigen isolated from the C. parvum parasite, as shown in the examples. In a still more preferred embodiment of the invention the peptide in the polypeptide comprises the amino acid sequence of the open reading frame (ORF) shown in Table 1 below or other open reading frames of the S34 DNA. Still other preferred polypeptides are those expressed by the S34 clone. In a most preferred embodiment, the polypeptide and fusion protein comprise one or more of the peptides shown in Table 4 below.

TABLE 1

Amino acid sequence of large S34 ORF

| 81 | | | | | | | | | 91 | | | | | | | | | |
|---|---|---|---|---|---|---|---|---|---|---|---|---|---|---|---|---|---|---|
| | gln | his | phe | leu | leu | gln | leu | glu | pro | gln | asp | asn | gln | gln | leu | leu | gln | leu |
| 101 | | | | | | | | | 111 | | | | | | | | | |
| glu | val | gln | ala | asn | gln | leu | leu | leu | pro | leu | ser | lys | ala | thr | thr | thr | thr | thr |
| 121 | | | | | | | | | 131 | | | | | | | | | |
| leu | asn | pro | ile | ile | thr | the | thr | thr | gln | lys | pro | thr | thr | thr | thr | thr | lys | val |
| 141 | | | | | | | | | 151 | | | | | | | | | |
| pro | gly | lys | pro | pro | ile | ala | thr | thr | thr | thr | leu | lys | pro | ile | val | thr | thr | thr |
| 161 | | | | | | | | | 171 | | | | | | | | | |
| thr | thr | lys | ala | thr | thr | thr | thr | thr | thr | val | pro | thr | thr | thr | thr | thr | thr | lys |
| 181 | | | | | | | | | 191 | | | | | | | | | |
| arg | asp | glu | met | thr | thr | thr | thr | pro | leu | pro | asp | ile | gly | asp | ile | glu | ile | thr |
| 201 | | | | | | | | | 211 | | | | | | | | | |
| pro | ile | pro | ile | glu | lys | met | leu | asp | lys | tyr | thr | arg | met | ile | tyr | asp | tyr | asn | ser |
| 221 | | | | | | | | | 231 | | | | | | | | | |
| gly | leu | leu | leu | asp | ser | asn | asp | glu | pro | ile | pro | gly | ser | gln | ala | gly | gln | ile | ala |
| 241 | | | | | | | | | 251 | | | | | | | | | |
| asp | thr | ser | asn | leu | phe | pro | gly | ser | asn | ser | gln | glu | tyr | trp | phe | thr | asn | (Sequence ID NO. 1) |

In another embodiment, the polypeptide of this invention is capable of binding a subgroup of anti-C. parvum antibodies that selectively bind a peptide selected from the group consisting of 15 and 32 to 35 kD (doublet) app. MW peptides from *C. parvum*, polypeptides of clones encoding other peptides encompassed by the 15 and 32 to 35 kD protein and fusion proteins of clones that hybridize to the S34 DNA insert. The subgroup of antibodies binding the 15 and 35 kD app. MW bands show substantially no binding affinity for the polypeptides expressed by the other clones but bind with specificity to the S24 protein, to other peptides encompassed by the 15 and 32 to 35 kD protein, and fusion proteins thereof. Polypeptides other than the S24 polypeptide may be obtained by screening a *C. parvum* DNA library(ies) with the S24 DNA and monoclonal and polyclonal antibodies. Still more preferred is a peptide that has an app. MW selected from the group consisting of 15 and 32 to 35 kD. These polypeptides cross-react with the peptide expressed by the S24 clone from *C. parvum*. In a still more preferred embodiment, the polypeptide and fusion protein of the invention comprise a peptide selected from the group peptides of Table 10 below.

In another aspect of this invention, the peptide in the polypeptide is capable of binding to a subgroup of antibodies that selectively bind to a peptide selected from the group consisting of the 68 and 95 kD app. MW peptides from *C. parvum*, polypeptides of clones encoding other peptides encompassed by the entire protein, and fusion proteins of clones that hybridize to the S19 DNA insert. The subgroup of antibodies binding to this particularly polypeptide of the S19 clone was found to be substantially non-overlapping with the group of antibodies that bind to the peptide of the S34 clone. In another preferred embodiment, the peptide has an app. MW selected from the group consisting of 68 kD and 95 kD. These peptides having an app. MW of 68 kD and 95 kD may be isolated in impure form from a *C. parvum* lysate electrophoresed on a gel, and then specifically bound with antibodies for this specific clone subgroup. The peptides and polypeptides may be prepared in substantially pure form by cloning as described herein. Also preferred is the peptide expressed by the S19 clone. In addition, other peptides binding to this subgroup of antibodies may also be obtained by recloning and expression of the DNA segments encoding them in an appropriate host as is known in the art. This subgroup of antibodies also binds to the S19 polypeptide, to other peptides encompassed by the 15 and 32 to 35 kD proteins, and fusion proteins thereof. Polypeptides comprising a peptide other than the S19 peptide may be obtained by screening a *C. parvum* DNA library(ies) with the S19 DNA and monoclonal and polyclonal antibodies. In a most preferred embodiment the polypeptide and fusion protein comprise a peptide shown in Table 6 below. Substantially no cross-reactivity exists between this group of peptides and the peptides of the other groups.

In another embodiment, the peptide in the polypeptide is capable of binding to a subgroup of anti-*C. parvum* antibodies that selectively bind to the 45 kD app. MW peptide from *C. parvum*. Also preferred, is the peptide expressed by the S2 clone, polypeptides of clones encoding other peptides encompassed by the entire protein, and fusion proteins of clones that hybridize to the S2 DNA insert. As in the previous cases, the subgroup of antibodies capable of binding to the 45 kD app. MW peptide from *C. parvum* may be isolated by elution after binding to the specific polypeptide expressed by a recombinant host carrying, e.g., the S2 clone. Monoclonal antibodies may also be obtained by methods known in the art such as the fusion of a lymphocyte expressing an antibody of this specificity with, e.g., a myeloma to form an antibody-producing hybridoma cell line of this given specificity. Substantially no overlapping or cross-reactivity has been found for the 45 kD app. MW peptide from *C. parvum* with the other polypeptides from clones corresponding to a different group. In a preferred embodiment of the polypeptide, the peptide has an app. MW of 45 kD. Such peptide may be produced by electrophoresing a lysate of *C. parvum*, Western blotting of the protein material and binding of polyclonal antibodies having specificity for the 45 kD peptide band thereto. The subgroup of antibodies selectively binding the 45 kD app. MW polypeptide also bind the S2 group of polypeptides, other peptides encompassed by the 45 kD protein, and fusion proteins thereof. Polypeptides other than the S2 polypeptide may be obtained by screening a *C. parvum* DNA library(ies) with the S2 DNA and monoclonal and polyclonal antibodies.

In another embodiment of the polypeptide, the peptide is capable of binding a subgroup of anti-*C. parvum* antibodies that selectively bind the 23 kD app. MW polypeptide from *C. parvum*, other peptides encompassed by the S7 protein or fusion proteins thereof. Preferred are the polypeptides having a 23 kD app. MW and that expressed by the S7 clone, polypeptide of clones encoding other peptides and fusion proteins of clones that hybridize to the S7 clone. The subgroup of antibodies shown to bind the 23 kD app. MW polypeptide also binds to the polypeptide expressed by the S7 clone group and fusion proteins thereof. This subgroup of antibodies shows substantially no-cross reactivity with other polypeptides from a different group of clones. In a preferred embodiment, the polypeptide and fusion protein comprise one or more peptide(s) shown in Table 8 below. In another preferred embodiment, the peptide in the polypeptide has an apparent molecular weight of 23 kD. Another preferred polypeptide is that expressed by the S7 clone. In still another preferred embodiment, the peptide in the polypeptide comprises fusion protein of the 23 kD polypeptide and a second unrelated peptide. In a still more preferred embodiment, the peptide comprises the peptide having the open frame sequence shown in Table 2 below, or other open reading frame sequences of the S24 DNA. In a most preferred embodiment, the polypeptide or hybrid protein comprise one or more of the peptides shown in Table 8 below.

TABLE 2

Amino acid sequence of large S7 ORF

41

51 ser  ile  glu  met

61

71 ser thr leu val arg lys leu ala pro asn phe thr ala glu ala val met ala asp gly

81

91 ser phe lys lys val ser leu ser asp tyr arg gly lys tyr val val leu phe phe tyr

TABLE 2-continued

Amino acid sequence of large S7 ORF

```
101                                     111
pro leu asn phe thr phe val cys pro ser glu ile leu ala phe asn gln ala gln lys 121                                     131
asp phe glu lys leu gly val gln leu leu ser cys ala gln leu ile leu asn thr pro 141                                     151
met leu his gly asp val leu leu leu asn lys val glu leu asp gln ser ile ser his 161                                     171
leu ser leu thr his leu ile gln leu ala arg thr met val tyr phe leu glu glu glu 181                                     191
gly ile ala leu arg gly leu phe ile ile asp lys glu gly arg val val arg ser glu 201                                     211
val ile tyr asp leu pro leu gly arg ser val glu glu thr leu arg val ile asp ala 221                                     231
leu gln phe thr glu thr tyr gly glu val cys pro ala asn trp lys lys gly gln lys 241                                     251
gly met ser ala thr his glu gly val ser ser tyr leu lys asp ser phe   (Sequence ID NO. 2)
```

Also part of this invention is a composition of matter that comprises
the polypeptide of this invention; and
a carrier, preferably a biologically-acceptable carrier, and more preferably a pharmaceutically-acceptable carrier.

Typical carriers are aqueous carriers such as water, buffered aqueous solutions, aqueous alcoholic mixtures, and the like. Compositions comprising carriers that are for pharmaceutical use, particularly for use in humans, comprise a carrier that is pharmaceutically-acceptable. Examples of such carriers are known in the art and need therefore not be provided herein.

The composition may comprise about 0.01 to 30 wt % of the polypeptide, and preferably about 2 to 20 wt % thereof. However, other proportions of the carrier to the polypeptide may also be utilized as an artisan will determine by the effectiveness of the treatment. The composition may further comprise other components such as an adjuvant, coloring, a pH adjuster, a filler, and the like, as is known in the art.

The carrier may be a solid or liquid carrier, depending on the route of administration. Typically, the polypeptides of the invention are administrated by the intravenous, subcutaneous or other systemic routes. Given the nature of polypeptides, they are preferably not administrated orally since they are rapidly degraded by the acid pH of the stomach.

Also provided herein is a biologically pure DNA segment encoding the polypeptide of the invention. In addition, provided herein are the DNA sequences for both strands of each clone. Moreover, given the degeneracy of the genetic code, there may be multiple DNA sequences encoding the same polypeptide. All are part of this invention. In a preferred embodiment of the invention, the DNA segment is selected from the group consisting of the DNA fragments of Tables 4, 6, 8, and 10, combinations and repeats thereof, and complementary and degenerate sequences thereof encoding the polypeptide(s). The DNA segments and fragments of different Cryptosporidium clone groups are shown in the tables provided with the examples. Also provided in the tables are the deduced amino acid sequences obtained by reading the two strands of DNA in all three possible reading frames. These amino acid sequences, however, may comprise some portions that are not part of the final polypeptide since they were obtained by translation of genomic polynucleotides and not from cDNA fragments. Thus, when transcription occurs, introns may be excised and the resulting polypeptide may have a substantially different amino acid sequence, be it because of a change in the reading frame or because of a portion was deleted at the RNA level. It is also possible that the deduced amino acid sequences represent solely a portion of the endogenous antigens, although they may comprise more than one epitope. In still another preferred embodiment, the DNA segment of this invention further comprises a second unrelated DNA sequence, such as a regulatory DNA sequence or any generic DNA sequence to add a large peptide to increase the immunogenicity of the polypeptide, that is operably coupled thereto. The addition of a regulatory DNA segment as the unrelated DNA segment permits the increased production of the expressed gene product, i.e., the polypeptide or hybrid protein.

Also part of this invention is an RNA segment that encodes the polypeptide of this invention. The different polypeptides are encoded by different RNA segments. In addition, the RNA segments may encompass degenerate sequences that encode the same polypeptide. All these are part of this invention. Also provided herein are RNA segments comprising substantially pure, isolated, RNA fragments corresponding to both strands of the DNA segments encoding the polypeptides of all five groups, combinations thereof and repeats thereof. A more preferred RNA segment of this invention comprises an RNA fragment selected from the group consisting of polyribonucleotide fragments corresponding to the DNA fragments of Tables 4, 6, 8 and 10, combinations and repeats thereof, and complementary and degenerate sequences thereof encoding the polypeptide of this invention. The RNA segments of this invention may be produced by transcription of the DNA segments disclosed herein by methods known in the art. In another preferred embodiment, the RNA segment further comprises an unrelated RNA segment that is operatively linked to the RNA segment of the invention.

Also provided herein is a fusion protein that comprises the polypeptide of the invention in all its different antigenic forms and a second unrelated polypeptide encoded by, e.g., a DNA segment operably coupled to the DNA segment encoding the polypeptide of the invention. An example of the second unrelated polypeptide is beta-galactosidase, where the DNA segment encoding this gene product also contains regulatory sequences. However, other polypeptides may also be used, such as to provide a large proteic component to increase immunogenicity. If the gene encoding the polypeptide of the invention is cloned within the beta-galactosidase gene, the two polypeptides may be expressed as a fusion protein and the amount of fusion protein produced is controlled by the regulatory sequences of the beta-galactosidase gene.

Also part of this invention is a hybrid vector, that comprises a vector capable of replication, transcription and expression of DNA segments operably coupled thereto; and a DNA segment encoding a polypeptide of this invention comprising at least one of the five immunologically different peptide groups disclosed herein operatively coupled thereto, wherein when the vector is placed in an appropriate host it can express the polypeptide encoded by the DNA segment. Examples of such vectors are pGex (Pharmacia), baculovirus, pET-9d (Novagen) or pRSET T7 (Invitrogen). However, other vectors may also be utilized. The vector may be a eukaryotic or a prokaryotic vector depending on the host selected for transfected and in which the gene product is going to be expressed.

This invention also encompasses a hybrid host carrying the hybrid vector of the invention. Examples of hosts suitable for use herein are prokaryotic and eukaryotic hosts such as *E. coli* K12 and related bacteria, and Sf9 or Sf21 insect cells (*Spodoptera frugiperda*), and chinese hamster ovary cells. However, other hosts may also be utilized.

Still part of this invention is another hybrid vector, that comprises a vector capable of replication, transcription and expression of DNA segments operably coupled thereto; and a DNA segment comprising a DNA fragment encoding at least one of the polypeptides of the invention and a second unrelated DNA segment, both sequences being operably coupled to one another and to the vector. The preparation of the hybrid vector described above is known in the art and need not be further described herein (Smith, D., and Johnson, K., "Single Step Purification of Polypeptides Expressed in *E. coli* as Fusions with Glutathione S-transferase", Gene 67:31(1988); Studier, F. W., Rosenberg, A. H., Dunn, J. J., and Dubendorff, J. W., "Use of T7 RNA Polymerase to Direct Expression of Cloned Genes", Meth. Enzymol. 185:60–89(1990)).

Also an important part of this invention is a method of diagnosing Cryptosporidium infection, that comprises contacting a body substance with an anti-Cryptosporidium antibody having specificity for the polypeptide of this invention; and detecting any selective binding of the antibody to any antigenic Cryptosporidium peptides present in the body substance. The detection of the antibody-polypeptide complex may be conducted by any method known in the art. This includes solid phase, double antibody, sandwich double antibody, and triple antibody assays, and the like, including ELISA assays. Also suitable for use herein are enzyme-linked immunoassays and radioactively labeled assays.

Also provided herein is a method of diagnosing Cryptosporidium infection, that comprises contacting a body substance with one of the polypeptides of this invention; and detecting any selective binding of the polypeptide to any anti-Cryptosporidium antibodies in the body substance. As in the previous case, the present antibody-polypeptide binding complex may be detected by a variety of methods such as those listed above. Examples of body substances are stools and other liquid or solid body output or tissue samples obtained from a subject. Examples of body fluids are blood, serum, saliva, urine, and the like. Methods for the preparation of the body substance and the body fluid are standard in the art and need not be further detailed herein (see, for example, Manual of Clinical Microbiology, Chapter 8, "Collection, Handling and Processing of Specimens", 4th edition, Eds, Lennette, E. H., Balows, A., Hausler, W. J. and Shadorny, A. J., American Society for Microbiology (1986)).

The immunotherapy of cryptosporidiosis in humans and animals may be conducted by the oral (intraluminal gastrointestinal) administration of the antibodies of the invention to patients with cryptosporidiosis to effectively reduce their symptomatology. In order to reduce to practice the invention, one of the present inventors and others conducted a multiplicity of experiments and made the following observations.

(1) The in vivo protective capacity of HBC was correlated with a significant inhibition of Cryptosporidium infection of MDCK cells by HBC Ig of the same lot, in a reproducible epithelial cell-Crysptosporidium assay. In a newborn calf model of acute crysptosporidiosis, HBC was shown to protect the animal from Crysptosporidium infection, to reduce the oocysts output to below the limit of detection, and to produce substantially no dehydration in the HBC treated animals. Moreover, an HBC Ig preparation was also shown to be protective in a therapeutic neonatal model of crysptosporidiosis, confirming that immune colostrum effectively and significantly reduces the infectivity and/or proliferation of Crysptosporidium. The in vitro inhibition of the invasion and intracellular development of Crysptosporidium was shown by one of the inventors and others to occur as a function of anti-Crysptosporidium titer as evidenced by its correlation with the corresponding immunoglobulin concentration in protective colostrum, and by the lack of biological activity of SHAM colostrum. In a supportive experiment, HBC Ig was also shown to significantly inhibit *C. parvum* infectivity in the Caco-2 cell line.

(2) The in vitro ability of HBC to prevent Crysptosporidium infectivity was shown to be, in fact, mediated by specific anti-Crysptosporidium antibodies and not by other antibodies or components, as shown by the inhibitory effect evidenced by the total antibodies eluted from a Western-blot of Crysptosporidium sporozoite/oocyst proteins. Fayer et al reported in 1990 that the antibodies in HBC were responsible for the protective activity of HBC in vivo. The experiments conducted by one of the inventors and others summarized here take Fayer's finding a step further by showing that antibodies to specific Crysptosporidium antigens are also responsible for the in vitro effect of the HBC Ig fraction. The inhibition in the in vitro assay correlated well with the effect of HBC and HBC Ig in vivo. Thus, the in vitro MDCK cell model stands validated as a model for detecting antibodies which are expected to be protective in vivo.

With the above validated model in hand, one of the inventors showed that antibodies raised to the fusion proteins of 3 of the antigens of the invention are significantly inhibitory in the in vitro MDCK cell model. This finding was then supported by similar results obtained with another epithelial cell line, MDBK cells. These observations indicate that the antibodies of the invention will be effective in vivo.

Thus, also part of this invention is a method of retarding, inhibiting or countering Cryptosporidium infection of a subject's cells comprising administering to a subject in need of such treatment an amount of the polypeptide of this invention capable of eliciting from the subject a host cell invasion and/or development inhibitory amount of anti-Cryptosporidium antibodies. Several Cryptosporidium polypeptides of this invention have been shown to elicit antibodies which inhibit Cryptosporidium infectivity and/or development inside the cell. In one preferred embodiment, the polypeptide of the invention, suitable for eliciting anti-Cryptosporidium antibodies in a mammal, comprises the S7, S24, S19, S34 or S2 polypeptides and other polypeptides encompassed by the corresponding entire proteins. More preferred are the S19, S34 and S2 polypeptides and other polypeptides encompassed by the corresponding entire proteins, and most preferred are S19 and S34 and other polypeptides encompassed by the corresponding entire proteins. Typically, a dose of about 0.02 to 10 mg is preferred, and more preferred is an amount of about 0.1 to 1 mg. However, other amounts are also suitable, as an artisan would know to adjust in accordance to weight and other variables such as the severity of the challenge.

This invention also provides a method of retarding, inhibiting or countering a Cryptosporidium infection of a subject's cells comprising administering to a subject in need of such treatment an amount of an antibody capable of binding to one or more of the polypeptides described above effective to retard the Cryptosporidium invasion of and/or development in the subject's cells. Antibodies selectively binding to several Cryptosporidium polypeptides have been shown by the inventors and others to inhibit Cryptosporidium infectivity in vitro. In one preferred embodiment, the antibody comprises anti-S7, anti-S24, anti-S19, anti-S34, or anti-S2 antibodies or mixtures thereof, other antibodies capable of selectively binding to other polypeptides encompassed by the corresponding entire proteins. More preferred are the anti-S19, anti-S34, anti-S2 or anti-S24 antibodies and other antibodies capable of selectively binding to other polypeptides encompassed by the corresponding entire proteins and even more preferred are the anti-S19, anti-S34 and anti-S2 antibodies and other polypeptides encompassed by the corresponding entire proteins. Typically, the antibodies specific for Cryptosporidium may be administered in an amount of about 0.01 to 100 g, and more preferably about 1 to 35 g. However, other amounts may also be prescribed depending on the severity of the infection and other variables, as an artisan would know.

Both the polypeptide and the antibodies of this invention may be administered in a composition also comprising a carrier, preferably a biologically-acceptable carrier, and even more preferably a pharmaceutically-acceptable carrier. Examples of carriers are those described above. Formulations suitable for the administration of polypeptides and antibodies such as those described herein are known in the art, and need not be further described herein. Typically, other components stimulatory of immune response may be added as well as fillers, coloring, and the like.

Still part of this invention is a kit for the diagnosis of Cryptosporidium infection, that comprises the polypeptide of this invention; and instructions for use of the kit.

This kit may be utilized for the detection of endogenous antibodies produced by a subject that is afflicted with cryptosporidiosis. Even at the early stages where the parasite is commencing invasion of a subject's cells, some amount of Cryptosporidium specific antibody may be detected in serum.

Also provided herein is another Cryptosporidium diagnostic kit, that comprises anti-Cryptosporidium antibodies having specificity for one of the polypeptides of this invention; and instructions for use of the kit.

Thus, kit may be utilized for the detection of Cryptosporidium polypeptides, a sign that there is parasite present in the subject being tested.

In addition to the above, the kits may also comprise a control, anti-antibodies, protein A/G, and the like, suitable for conducting the different assays referred to above.

Having now generally described this invention, the same will be better understood by reference to certain specific examples, which are included herein for purpose of illustration only and are not intended to be limiting of the invention or any embodiment thereof, unless so specified.

EXAMPLES

Example 1

Parasites

Cryptosporidium sp. oocysts isolated from patients with AIDS at San Francisco General Hospital were used in the production of polyclonal and monoclonal antibodies and for molecular karyotype analysis.

Oocysts were isolated by resuspension of 1 vol. of feces with 2 vol. of a saturated NaCl solution. All subsequent procedures were done at 4° C. After centrifugation at 1,000 g, the supernatant was recovered and the procedure repeated 3 times. The oocysts were recovered from the pooled supernatants by centrifugation, purified further in a 55%–27.5%–14% sucrose gradient at 1000 g for 20 min., and stored in PBS. Prior to use, the oocysts were sterilized by incubation in 15% commercial bleach, and washed by repeated centrifugation and re-suspension in PBS. The purified oocysts were excysted by incubation in Rpmi medium (gibco) with the addition of 0.75% sodium taurocholate (Sigma), pH 7, for 40–60 min. at 37° C.

Sporozoites were separated from unexcysted oocysts and debris by filtration through a polycarbonate 3 µm pore size membrane (Millipore).

Cryptosporidium oocysts from calves (Dr. Bruce Anderson, University of Idaho) were used for the isolation of DNA for the construction of the lambda gt11 genomic expression libraries. Cryptosporidium parvum oocysts of an AUCP-1 isolate (Dr. Byron Blagburn, Auburn University, Auburn, Ala.) propagated in Holstein calves were used for Western blots and indirect immunofluorescent antibody (IFA) studies.

Example 2

Preparation of Murine Polyclonal and Anti-oocyst/ Sporozoite MAbs 10 week-old female BALB/c mice were immunized four times intraperitoneally with approximately $5 \times 10^5$ sonicated C. parvum oocysts. The ascites were extracted and the antibodies isolated there- from. The polyclonal antibody fraction of the ascites was shown to react with the C. parvum sporozoite surface, the oocyst surface and internal antigens of the oocysts as assessed by an IFA as described in Petersen et al., Infect. Immun. 60(12):5132 (1992).

For monoclonal antibody production, mice were immunized intravenously with the supernatant from sonicated *C. parvum* oocysts three days before fusion as previously described by Kearney et al and Danforth et al (Kearney et al., J. Immunol. 123:1548(1979); Danforth et al., J. Parasitol. 68:1029(1982)). The hybridoma supernatants were used as the source of antibodies.

Six sporozoite monoclonal antibodies were obtained. The 10C6, 7B3 and E6 monoclonal antibodies were determined to be of subclass IgG1 by an ELISA (Zymed) assay. The supernatants of the corresponding hybridoma cultures were used for IFA studies and Western blots.

Example 3

Immunoprecipitation Study

A *C. parvum* extract was prepared from a lysate using 2% SDS and 1% Triton X-100, and immunoprecipitated as described by Leech et al (Leech et al., J. Exp. Med. 159:1567(1984)). Monoclonal antibodies obtained in Example 2 above were added to the lysate and the resulting immune complexes collected with protein A/G agarose beads. The *C. parvum* polypeptides from the immune complexes were separated on 5% SDS-PAGE gels and analyzed using a Western blot.

Example 4

Surface Iodination and Furhter Immunoprecipitation Studies

Sporozoites were washed twice by resuspension in Dulbecco-PBS with the addition of 1% glucose, taken to a final concentration of $10^9$ cells/ml, and radiolabeled with 300 µCi of $^{125}$INa (Amersham, Arlington Heights, Ill.) in an Iodogen (Pierce, Rockford, Ill.) coated glass vial as previously described, with the exception that addition of 5 mM KI was omitted (Gardiner, P. R., et al., "Iodination and Identification of Surface Membrane Antigens in Procyclic *Trypanosoma rhodesiense*", J. Imm. 131 (1 ):453 (1983)). Radiolabeled sporozoites were subsequently washed three times in RPMI medium with protease inhibitors as described above. After disruption of the labeled sporozoites by 5 cycles of freezing-thawing, the membrane pellet and the soluble fraction containing cytoplasmic proteins were collected. An aliquot of the membrane pellet was directly boiled in SB, and stored at –70° C. (sporozoite membrane proteins).

The remaining membrane material was divided into two radiolabeled samples. Prior to immunoprecipitation, one aliquot was extracted by boiling in SB as above, followed by addition of 9 vol. of NETT (0.15M NaCl; 5 mM EDTA; 0.5M Tris; 0.5% Triton X-100; pH 7.4) with 1% BSA (Sigma), 1% Triton-X 100, and protease inhibitors (SDS solubilized membranes). The other radiolabeled membrane sample was extracted directly with 3 vol. of NETT with 1% BSA, 1% Triton X-100, and protease inhibitors (Triton X-100 solubilized membranes). Both samples were pre-cleared by addition of 1 µl SHAM-HBC Ig followed by overnight incubation at 4° C. Subsequently, 200 µl of Protein G-Sepharose 4B beads were added and the samples rocked for 1 hr. at room temperature. After centrifugation at 10,000 g, HBC Ig affinity bound to Protein G-Sepharose 4B beads (300 µl) were added to the supernatants and the samples rocked for an additional 2 hrs. at 37° C.

The immunoprecipitates were washed sequentially with NETT buffer alone and NETT containing 1% BSA (Sigma) or 500 mM NaCl, then boiled in SB and stored at –70° C. Proteins were separated in 5–15% gradient gels by SDS-PAGE, and processed for autoradiography using X-Omat film (Kodak). Iodination controls consisted of trichloroacetic acid (TCA) precipitates of the soluble fraction containing sporozoite cytoplasmic proteins which were also processed as described above.

Example 5

Preparation of HBC

Hyperimmune bovine colostrum (HBC lot#40529) was obtained from ImmuCell Corporation (Portland, Me.) and was prepared by repeated parenteral immunization of Holstein cows during pre-parturition with partially excysted *C. parvum* oocysts. Immunogens were emulsified in Freund's adjuvant.

SHAM-HBC (lot #41038) was prepared after immunization with a commercial herd health vaccine which was also given to cows immunized with *C. parvum* to prepare HBC (lot#40529).

Colostra were collected using standard dairy practices and frozen. A 0.45 µm filtered, lyophilized colostral whey immunoglobulin (Ig) preparation, free of low molecular weight solutes, was prepared from pooled colostra from several immunized animals. Colostra were partially purified to obtain antibody products highly enriched for IgG (HBC Ig and SHAM-HBC Ig).

Colostral Ig concentrates were prepared using large scale production methods developed at ImmuCell Corp. Briefly, a pasteurized whey preparation of colostrum was prepared to eliminate the majority of caseins and fat. This preparation was then subjected to a series of ultrafiltration and microfiltration steps to remove small molecular weight solutes such as lactose and some whey proteins/peptides as well as particulate matter including residual fat and caseins. The resulting concentrate was filtered, dried and shown to be stable at room temperature. These preparations were greater than 85% protein by weight, and greater than 55% IgG on a protein basis. The degree of IgG purification was at least 2 fold.

The HBC of lot #40529 was used in the animal protection studies of Example 32 below, and the HBC Ig (50 mg/ml IgG) of the same lot was used in the in vitro inhibition of development studies of Example 34 below. Anti-Cryptosporidium Ab titers were determined independently several times for each colostrum preparation. HBC Ig (lot #40529) had an average anti-Cryptosporidium antibody titer of $1/176,000$ U/ml for a 43 µg/ µl IgG concentration by ELISA. SHAM-HBC Ig (lot #41038) had an approximately ten fold lower average antibody titer to Cryptosporidium antigens by ELISA (17,000 U/ml for a 45 µg/ µl IgG concentration), probably due to natural infection of the animals in the field.

Example 6

Assessment of in vivo Efficacy of HBC

Four newborn, colostrum deprived Holstein calves were fed 100 ml HBC (lot#40529) plus 2 quarts commercial milk replacer at 4 hrs. of age (treated group). Similarly, four calves were fed non-immune colostrum (control group) and all other parameters were equal. All 8 animals were challenged at 12 hrs. of age with $5 \times 10^6$ oocysts of *C. parvum*. All animals were fed 100 ml of SHAM-HBC or HBC every 24 hrs. and 2 qt milk replacer every 12 hrs.

Clinical observations of diarrhea and dehydration were made every 12 hrs. over a 7 day interval on all calves, and fecal samples were taken every 12 hrs. Fecal and dehydration scores were tabulated from days 5–7, the days of peak patency. Oocyst shedding was tabulated over days 5–9 post infection in ¾ treated animals and ⅔ controls. Samples from the remaining animals were not available. Oocyst shedding was measured by mixing 1 vol. fecal sample with 4 vol. Sheather's solution and enumerating the refractive oocysts in a hemocytometer. Confirmation of the oocyst counts was performed with a commercial immunofluorescence kit utilizing a monoclonal anti-oocyst antibody (Merifluor, Meridian Diagnostics, Cincinnati, Ohio).

The efficacy of the immune colostrum preparation for protecting the treated calves from $C.$ $parvum$ infection was demonstrated in statistically significant differences between treated and control animals in cumulative fecal scores ($p<0.01$ by one tailed t test) and dehydration scores ($p<0.01$ by one tailed t test).

No dehydration occurred in the treated group whereas all of the calves in the control group showed some signs of dehydration. The oocyst output was dramatically reduced in the treated group ($<10^3$ oocysts per total fecal output, the limit of detection) when compared to the control group (geometric mean oocyst output=$5.62\times10^8$).

These results clearly show that the immune colostrum treatment was effective to reduce the initial colonization by $C.$ $parvum$ parasites as well as to suppress the intestinal proliferation of the $C.$ $parvum$ parasites which were not initially neutralized.

Example 7

Preparation of $C.$ $parvum$ DNA Expression Libraries

Two $C.$ $parvum$ lambda gt11 genomic expression libraries were constructed. A restriction fragment expression library described by Kim et al and Nelson et al was utilized (Kim et al., Mol. Biochem. Parasitol., 50:105(1992); Nelson et al., J. Protozool. 386:52 (1991)).

A second expression library was constructed using aliquots of $C.$ $parvum$ DNA which was partially digested with DNase I in 33 mM Tris-HCl pH 7.4, 5 mM $CaCl_2$ for 15 min. Briefly, EDTA was added to a concentration of 20 mM, and aliquots removed and extracted once with phenol, and pooled. The pooled sample was extracted twice with phenol, twice with chloroform:isoamyl alcohol and once with diethyl ether and then ethanol precipitated. The DNA was subsequently treated with Klenow and T4 DNA polymerases to repair staggered ends, with EcoRI methylase to protect internal EcoRI sites and ligated to EcoRI linkers (pCCGAATTCGG) as is known in the art (Petersen et al., Infect. Immunol. (1992), supra). The polymeric linkers were removed by EcoRI digestion, and the DNA was purified by exclusion chromatography on Sephadex G-100. Any DNA eluting in the void volume was ethanol precipitated and ligated to EcoRI-cleaved, alkaline phosphatase-treated lambda gt11 arms, packaged in vitro, plated and amplified in $E.$ $coli$ strain Y1090. The resulting library was 70% recombinant and contained 1.2 million independent clones.

Example 8

Screening of the Two Expression Libraries

The two libraries were screened with polyclonal anti-$C.$ $parvum$ oocyst/sporozoite antibodies obtained as described in Example 2 and positive clones were plaque purified as described by Petersen et al., Infect. Immun. (1992), supra. 275,000 plaques from the amplified restriction fragment library were screened. 52 of those clones expressing fusion proteins were identified and purified. In addition, 225,000 plaques of the DNase library were screened and 5 of those clones were identified as positive and purified.

Example 9

Separation of Antibody Subgroups Specifically Binding Polypeptides from 5 Distinct Groups Antibodies specifically binding to the 5 distinct sporozoite polypeptide groups from IPTG-induced confluent plaque lifts of purified lambda gt11 clones were selected by affinity chromatography from a polyclonal anti-$C.$ $parvum$ oocyst/sporozoite antibody preparation on the respective plaque-lifts. The antibodies were then eluted with 10 mM glycine pH 2.6, and 150 mM NaCl as described by Beall and Mitchell (Beall and Mitchell, J. Immunol. Meth. 86:217 (1986); Coppel et al., Protocols in Molec. Parasitol., in Methods in Molecular Biology Series, Humana Press, New Jersey (1993); Petersen et al., Mol. Biochem. Parasitol. 42:189 (1990)). Antibodies were isolated from each of the 57 expressing clones.

Example 10

Sibling Analysis of Recombinant Clones

Approximately 400 plaque forming units (pfu) of each of the lambda gt11 purified clones and wild type lambda gt11 were individually dotted in a grid pattern onto a lawn of Y1090 on 152 mm Petri dishes. The dishes were incubated for 3 hrs at 37° C., and then a nitrocelluose filter saturated with 50 mm IPTG was applied to each lawn and allowed to incubate overnight. The filters were then removed and washed three times in TBSTA (10 mM Tris-HCl, pH 8.0; 150 mM NaCl; 0.05% Tween; 0.2% Na azide), and blocked with 1% BSA-TBSTA. Each of the 57 filters was incubated with a single antibody sample prepared from one of the clones for 2 hrs., washed 3 times with TBSTA and incubated with goat anti-mouse IgG conjugated to alkaline phosphatase (Promega) for 1 hr. The filters were then developed with the colorometric reagents nitro-blue tetrazolium and 5-bromo-4-chloro-3-indoyl phosphate.

Each of the 57 recombinants was thus segregated into 1 of 5 sibling groups based on the immunologic cross-reactivity of their encoded antigens. For example, antibodies isolated from clone S34 bound to fusion proteins expressed by clones S34, S38, S41 and S57 but not to the proteins expressed by the other 53 recombinants or wild type lambda gt11 clones. Correspondingly, antibodies isolated from clone S38 bound to clones S34, S38, S41 and S57 but to none of the other clones. The number of clones in each of the sibling groups is indicated in column 2 of Table 3 below.

TABLE 3

| Sibling Group | Number of Clones | IFA Localization | MW of Protein |
|---|---|---|---|
| | Sporozoite Proteins Encoded by Cloned C. parvum Gene | | |
| S34 | 4 | 1/2 sporozoite | >900 |
| S19 | 2 | apical | 68/95 |
| S2 | 4 | flocculant | 45 |

TABLE 3-continued

| | Sporozoite Proteins Encoded by Cloned *C. parvum* Gene | | |
|---|---|---|---|
| Sibling Group | Number of Clones | IFA Localization | MW of Protein |
| S7 | 1 | diffuse | 23 |
| S24 | 5 | diffuse | 15/32–35 |

Example 11

Indirect IFA Localization of Endogenous Antigens in Sporozoites and Oocysts

Slides containing air-dried, acetone-fixed sporozoites and oocysts were incubated with antibodies isolated as described in Example 8 above for 1 hr in a humidified chamber, washed with phosphate buffered saline, pH 7.4, and incubated with affinity purified goat anti-mouse IgG/IgA/IgM conjugated with fluorescein isothiocyanate (Zymed). The slides were counterstained with Evan's blue, and coverslips were applied onto them. The slides were then observed and photographed with a microscope (Nikon Optiphot) equipped for immunofluorescence with fluorescein.

A diffuse IFA staining pattern of sporozoites was produced with the antibodies. This pattern indicated which of the sibling groups contained clones encoding *C. parvum* polypeptides that were candidates to reside in the sporozoite pellicle. The IFA staining of the anterior portion of the sporozoites, where rhoptries, micronemes and dense granules are located, served to identify candidate apical organelle polypeptides.

The antibodies eluted from clones of the S34 group reacted with the anterior one-half of fixed sporozoites on an IFA whereas antibodies eluted from clones of the S19 group reacted with the anterior tip of the sporozoite in a very localized manner and antibodies eluted from clones of the S2 group exhibited a flocculant pattern over the sporozoites. The antibodies eluted from the single S7 clone, and members of the S24 group on the other hand, reacted diffusely with the fixed sporozoite on IFA but not with the oocyst.

The localization of antigens specific for the antibodies eluted from cloned antigens is indicated in column 3 of Table 3 above.

Example 12

Identification of Endogenous Antigens Encoded by Cloned Gene Fragments

One hundred million oocysts were suspended in 500 µl of a protease inhibitor cocktail containing 100 µM leupeptin (Sigma), 100 µM chymostatin (Sigma), 100 µM pepstatin (Sigma), 100 µM trans-epoxysuccinyl-L-leucylamido (4-guanidino)-butane (Sigma), 100 µM phenylmethylsulfonyl fluoride (Sigma), 50 mM N alpha-para-tosyl-L lysine chloromethyl ketone (Sigma), 150 mM NaCl and 500 mM EDTA, pH 8.0, and lysed by 5 freeze-thaw cycles. Western blots were prepared as described by Petersen et al (Petersen et al., Mol. Biochem. Parasitol. 42:189(1990)), and incubated with the individual eluted antibodies.

Alkaline phosphatase labeled second antibodies and the substrates described above, were used to detect antigens which bound to the eluted antibody. The Western blots were scanned with a Hewlett Packard flatbed scanning densitometer in reflectance mode prior to photography. Nebulin (900 kD; Stedman et al., Genomics 2:1(1988)), and titin (2500 kD, Kurzban and Wang, Biochem. Biophys. Res. Commun. 150:1155(1989)), were used as high molecular weight standards. These standards were provided by Dr. Kuan Wang, University of Texas, Austin.

The antibodies eluted from the five sibling groups encoding sporozoite proteins recognized distinct polypeptides on Western blots. The antibodies eluted from clones of the S34 group bound to a polypeptide of apparent molecular weight >900 kD on Western blots of oocyst/sporozoite proteins. This polypeptide migrated faster than titin at 2500 kD and slower than nebulin at 900 kD.

Antibodies eluted from clones of the S19 group bound to a polypeptide apparent molecular weight 68 kD, and weakly bound to a polypeptide of molecular weight 95 kD. The antibodies eluted from the S2 group bound to a 45 kD polypeptide. The antibodies eluted from the S7 group bound to a 23 kD polypeptide, and antibodies eluted from the S24 group bound to a 15 kD polypeptide doublet and to a 32–35 kD polypeptide doublet on Western blots.

Western blots probed with the murine oocyst/sporozoite antibodies from which the eluted antibodies were isolated indicated that the antibodies reacted with many different oocyst/sporozoite antigens. Control eluted antibodies prepared from wild type lambda gt11 clones which only express beta-galactosidase showed substantially no binding to oocyst/sporozoite polypeptides. This clearly indicates that the elution process yielded highly specific antibody. It is unclear if the fact that multiple polypeptide bands were identified by the S19 and S24 eluted antibodies is due to antigenic cross-reactivity or post-translational processing. Although parasite proteolysis occurring prior to lysis in protease inhibitors cannot be ruled out it appears unlikely since use of the protease cocktail routinely allowed the detection of the polypeptide of apparent molecular weight >900 kD of the S34 family in undegraded form. This indicates that protein degradation is minimal.

The molecular weights of endogenous polypeptides for which the antibodies eluted from the cloned antigens have specificity is indicated in column 4 of Table 3 above.

Example 13

Detection of High Molecular Weight *C. parvum* Polypeptide with HBC IgG

A whole oocyst/sporozoite lysate was electrophoresed in a 5% SDS-PAGE gel and Western blotted with HBC IgG. At least 10 polypeptides were identified. Because of the compression effect of the polypeptides in the region below the 46 kD band, the number of polypeptides in that region bound by HBC is uncertain. Sham IgG did not identify any proteins. An antigen identified by HBC IgG which generated a very strong signal co-migrated with a very high molecular weight antigen recognized by MAb 10C6.

Immunoprecipitation of Triton X-100 soluble oocyst/sporozoite proteins with monoclonal antibody 10C6 followed by SDS-PAGE and Western blot with HBC Ig confirmed that the antigenic sites reside on the same molecule. Control lanes indicate that additional antigens are heavy and light chains from antibodies in the fractionated immune complexes. Coomassie blue staining of SDS-PAGE gels suggested that the >900 kD antigen predominates over other proteins in oocyst/sporozoite lysates.

Studies with surface labeled parasites immunoprecipitated with HBC Ig indicated that the >900 kD antigen is surface exposed.

Example 14

Binding of Sporozoite Specific Monoclonal Antibodies to >900 kD Apparent MW Polypeptide

Immunoprecipitation of Triton X-100 extracted oocyst/sporozoite polypeptides with monoclonal antibody 10C6 followed by Western blot with monoclonal antibodies 10C6, 7B3 and E6 evidenced that all three monoclonal antibodies bound to the same molecular weight >900 kD band. Thus, three of six monoclonal antibodies developed to sporozoites had specificities directed at epitopes of this antigen. In addition, three monoclonal antibodies out of eight raised against intracellular organisms recognize this same antigen suggesting that it, or a crossreacting antigen, is also present in the merozoites.

The 7B3 monoclonal antibody also identified a 38 kD apparent molecular weight antigen on a Western blot of whole oocyst/sporozoite lysates but not on Western blots of whole sporozoite lysates. This suggests that a molecule from oocysts that is insoluble in Triton-X-100 also reacts with monoclonal antibody 7B3, the monoclonal antibody reacting with the anterior portion of fixed sporozoites on an IFA. When the 10C6 monoclonal antibody was used in an IFA of fixed intracellular merozoites cultivated in MDCK cells, a linear pattern was obtained that suggested localization at the pellicle of the elongated merozoite. This indicates that the epitope for which the monoclonal antibody 10C6 has specificity is also present in this second invasive stage.

Example 15

Inhibition of C. parvum Infection by GP900 Polypeptide Specific Monoclonal Antibody

Sporozoites were obtained from oocysts isolated from calves infected with the AUCP-1 strain of C. parvum. The sporozoites were cultured in vitro on Madin-Darby canine kidney (MDCK) cells as described by Gut et al (Gut et al., J. Protozool. 386:56 (1991)).

Briefly, freshly excysted, untreated, sporozoites were allowed to invade monolayers of MDCK cells in a quantitative fashion. The sporozoites underwent cycles of asexual and sexual development.

In another experiment, when viable sporozoites were pre-incubated for 30 minutes with monoclonal antibody 10C6, it inhibited the invasion of MDCK cells by greater than 90% when compared to control antibody.

GP900 thus appears to be an effective target for passive or active antibody immunotherapy. In addition, monoclonal antibody 10C6 was shown to be an effective antibody against GP900.

Example 16

The >900 kD App. MW C. parvum Polypeptide is N-glycosylated

A Western blot analysis of oocyst/sporozoite polypeptides immunoprecipitated with monoclonal antibody 10C6 indicated that the S34 eluted antibodies bind to the >900 kD polypeptide that is also immunoprecipitated by monoclonal antibody 10C6. Thus, the S34 polypeptide encodes a portion of the >900 kD app. MW polypeptide. The >900 kD polypeptide is a highly immunogenic molecule that binds to the 10C6, 783 and E6 monoclonal antibodies and to HBC IgG.

A C. parvum lysate was incubated overnight at 37° C. with N-glycosidase F (Boehringer Mannhelm, EC 3.2.2.18) according to Boehringer Mannhelm instructions, and then electrophoresed in a 5% SDS PAGE gel and Western blotted. To control proteolysis during the incubation, the C. parvum lysate was incubated under the same conditions in the absence of N-glycosidase F enzyme.

The oocyst/sporozoite proteins were treated with N glycosidase F, and then electrophoresed on a 5% SDS PAGE gel and Western blotted with the 10C6, 7B3 and E6 monoclonal antibodies. None of the monoclonal antibodies detected an antigen on the Western blots. However, the S34-eluted antibodies recognized multiple C. parvum N-deglycosylated proteins of apparent molecular weight <200 kD.

Taken together these results indicate the following.

1) The monoclonal antibodies react with an epitope that requires intact N-glycosylation.
2) The polypeptide is thus a glycopeptide.
3) The apparent molecular weight of the N-deglycosylated polypeptide is <190 kD.
4) Immunoprecipitation of Triton X-100 soluble oocyst/sporozoite polypeptides and SDS extraction of the Triton X-100 insoluble pellet indicate the >900 kD apparent molecular weight glycoprotein to be mostly Triton X-100 soluble.

Example 17

A Single Copy Gene Encodes >900 kD Apparent Molecular Weight Glycoprotein

The genomic Southern analysis and $^{32}$P dATP labeling of a 1.2 kb S34 DNA insert cloned into pGem was carried out as described by Petersen et al. (Petersen et al., Mol. Biochem. Parasitol. 36:61 (1989)).

After hybridization, the membranes were washed with 0.1× SSPE, 0.25% Sarkosyl at 65° C. and an autoradiogram obtained. The autoradiogram of the genomic Southern blot was scanned with a Hewlett Packard flatbed scanning densitometer prior to photography. The chromosomes were transferred to membranes and molecular karyotype analysis was performed probing with pGemS34 as described by Kim et al. (Kim, et al., Mol. Biochem. Parasitol. 50:105 (1992)).

Genomic Southern analysis showed the 1.2 kb S34 insert to hybridize with single BstE II, Apa I, Bcl I, Cla I and SSp I fragments of approximate size of 9.0, >23, >23, 6, and 4 kb, respectively, and with two restriction fragments generated by Ba II.

These results show the >900 kD glycoprotein to be encoded by a single copy gene. Molecular kararoyotypic analysis also showed that the gene is located on the largest detected C. parvum chromosome, a chromosome of approximately 1,400 kb in both bovine and human isolates.

Example 18

DNA Sequence of Clone S34

The DNA nucleotide sequence of the C. parvum insert of clone S34 was determined by chain termination DNA sequencing (Sanger, F., et. al., Proc. Nat. Acad. Sci. (USA) 74:5463 (1977)). Cryptosporidium DNA inserts were excised from lambda gt11 with EcoRI and ligated into m13 (Messing, J., Methods in Enzymology 101:20 (1983)) prior to sequencing. Sequencing was carried out exactly as detailed on pages 6–9 of the Sequenase$^R$ Version 2.0 protocol provided with the commercially available enzyme, Sequenase$^R$ (United States Biochemical, pages 6–9). Labeled m13 mixtures were separated by denaturing gel electrophoresis using a Bio-Rad sequencing cell.

The DNA sequence obtained and that of its complementary strand are provided in Table 4 below as well as the 6 possible amino acid sequences deduced therefrom.

TABLE 4

DNA and amino acid sequence of clone S34

SEQUENCE DESCRIPTION: SEQ ID NO. 3:

| Glu 1 | Phe | Pro | Asp | Arg 5 | Ser | Leu | Asp | Phe | Thr 10 | Ile | Pro | Pro | Val | Ala 15 | Gly |
|---|---|---|---|---|---|---|---|---|---|---|---|---|---|---|---|
| His | Asn | Ser | Cys 20 | Ser | Ile | Ile | Val | Gly 25 | Val | Ser | Gly | Asp | Gly 30 | Lys | Ile |
| His | Val | Ser 35 | Pro | Tyr | Gly | Ser | Lys 40 | Asp | Val | Ser | Leu | Ile 45 | Ser | Ala | Pro |
| Ile | Gln 50 | Pro | Ser | Glu | Leu | Phe 55 | Asn | Glu | Val | Tyr | Cys 60 | Asp | Thr | Cys | Thr |
| Ala 65 | Lys | Tyr | Gly | Ala | Ile 70 | His | Ser | Gly | Tyr | Gln 75 | Thr | Ser | Ala | Asp | Phe 80 |
| Val | Thr | Thr | Leu | Pro 85 | Thr | Thr | Thr | Gly | Ala 90 | Ala | Gly | Gln | Pro | Thr 95 | Thr |
| Thr | Thr | Thr | Gly 100 | Ser | Pro | Ser | Lys | Pro 105 | Thr | Thr | Thr | Thr | Thr 110 | Ile | Xaa |
| Gly | Asn | Asn 115 | Asn | His | Asn | Asn | Ser 120 | Xaa | Ser | Asn | His | Tyr 125 | Asn | Asn | Asn |
| Ser | Lys 130 | Thr | Asn | Asn | Asn | Asn 135 | Asn | Asn | Lys | Gly | Ser 140 | Arg | Xaa | Ala | Thr |
| Asn 145 | Ser | His | Asn | Asn | Asn 150 | Asn | Ile | Lys | Ala | Asn 155 | Ser | Tyr | Asn | Asn | Asn 160 |
| Asn | Lys | Ser | Asn | Asn 165 | Asn | Asn | Asn | Asn | Asn 170 | Ser | Ala | Asn | Asp | Asn 175 | Tyr |
| Tyr | Tyr | Gln | Glu 180 | Arg | Arg | Asn | Asp | Asn 185 | Asn | Asn | Asp | Thr | Ile 190 | Thr | Xaa |
| Tyr | Arg | Xaa 195 | His | Xaa | Asn | Tyr | Thr 200 | Asn | Pro | Asn | Xaa | Lys 205 | Asp | Val | Gly |
| Xaa | Val 210 | His | Lys | Asn | Asp | Leu 215 | Xaa | Leu | Xaa | Gln | Trp 220 | Phe | Ile | Ile | Arg |
| Leu 225 | Xaa | Xaa | Xaa | Thr | Asn 230 | Ser | Arg | Phe | Ser | Ser 235 | Arg | Thr | Asn | Ser | Xaa 240 |
| Tyr | Lys | Gln | Phe | Ile 245 | Pro | Arg | Phe | Lys | Leu 250 | Thr | Arg | Val | Leu | Val 255 | Tyr |
| Gln | Leu | Ile | Gln 260 | Trp | Leu | Val | Phe | His 265 | Leu | Ile | Gln | Asn | Gln 270 | Val | Ile |
| Xaa | Tyr | Ile 275 | His | Ile | Pro | Ile | Lys 280 | Gln | Cys | Leu | Val | Tyr 285 | Arg | Tyr | His |
| Ile | Leu 290 | Leu | Leu | Arg | Ile | Xaa 295 | Gln | Leu | Ile | Leu | Met 300 | Lys | Leu | Arg | Phe |
| Thr 305 | Asn | Xaa | Tyr | Thr | His 310 | Trp | Leu | Pro | Ile | Gly 315 | Ser | Ser | Gln | Phe | Asp 320 |
| Ser | Val | Gln | Ser | Arg 325 | Asn | Trp | Xaa | Ile | Val 330 | Cys | Pro | Ile | Ser | Asp 335 | Glu |
| Ile | Met | Asn | Gly 340 | Thr | Ile | Ala | Gly | Ile 345 | Val | Ser | Gly | Ile | Ser 350 | Ala | Ser |
| Glu | Ser | Leu 355 | Leu | Ser | Gln | Lys | Ser 360 | Leu | | | | | | | |

SEQUENCE DESCRIPTION: SEQ ID NO. 4:

| Arg | Val | Pro | Arg | Xaa 5 | Lys | Phe | Gly | Phe | His 10 | Asn | Ser | Ser | Ser 15 | Trp |
|---|---|---|---|---|---|---|---|---|---|---|---|---|---|---|

TABLE 4-continued

DNA and amino acid sequence of clone S34

Pro Xaa Gln Leu Phe Asn Asn Ser Trp Cys Glu Arg Arg Trp Lys Asn
         20                  25                  30

Ser Arg Lys Pro Ile Arg Phe Xaa Gly Cys Leu Ser Asn Lys Cys Ser
         35              40                  45

Asn Thr Thr Phe Xaa Val Ile Gln Xaa Ser Leu Leu Arg His Leu Tyr
    50              55                  60

Cys Glu Val Trp Cys Asn Ser Leu Trp Ile Ser Asn Phe Ser Xaa Phe
65                  70              75                  80

Arg Asn Asn Thr Ser Tyr Tyr Asn Trp Ser Arg Arg Thr Thr Asn Asn
             85              90                  95

Tyr Tyr Asn Trp Lys Ser Lys Gln Thr Asn Tyr Tyr Tyr His Tyr Leu
         100             105                 110

Arg Gln Gln Gln Pro Gln Gln Leu Leu Ile Gln Ser Leu Gln Gln Gln
         115             120             125

Leu Lys Asn Gln Gln Gln Gln Gln Gln Gln Arg Phe Gln Val Ser His
    130             135                 140

Gln Xaa Pro Gln Gln Gln Gln His Xaa Ser Gln Xaa Leu Gln Gln Gln
145         150                     155                 160

Gln Gln Lys Gln Gln Gln Gln Gln Gln Gln Cys Gln Arg Gln Leu
             165             170                 175

Leu Leu Pro Arg Glu Thr Lys Xaa Gln Gln Gln Arg His His Tyr Leu
         180             185                 190

Ile Ser Val Thr Leu Lys Leu His Gln Ser Gln Leu Lys Arg Cys Trp
    195             200                 205

Ile Ser Thr Gln Glu Xaa Phe Met Thr Ile Thr Val Val Tyr Tyr Xaa
    210             215                 220

Thr Leu Met Met Asn Gln Phe Gln Val Leu Lys Gln Asp Lys Xaa Leu
225             230             235                 240

Ile Gln Ala Ile Tyr Ser Gln Val Gln Thr His Lys Ser Thr Gln Leu
             245             250             255

Pro Ile Asp Pro Met Val Gly Leu Pro Phe Asp Pro Lys Ser Gly Asn
         260             265             270

Leu Val His Pro Tyr Thr Asn Gln Thr Met Ser Gly Leu Ser Val Ser
    275             280             285

Tyr Leu Ala Ala Lys Asn Leu Thr Val Asp Thr Asp Glu Thr Thr Val
    290             295             300

Tyr Gln Leu Ile His Ser Leu Val Thr His Trp Ile Gln Ser Val Xaa
305             310             315             320

Phe Arg Ser Ile Gln Lys Leu Val Asn Cys Leu Ser Asn Ile Arg Xaa
             325             330             335

Asp Asn Glu Trp Asn Asn Cys Arg Tyr Cys Phe Arg Asn Phe Cys Lys
         340             345             350

Xaa Val Ile Ile Ile Ser Glu Ile Ala
         355             360

SEQUENCE DESCRIPTION: SEQ ID NO. 5:

Ala Ser Ser Gln Ile Glu Val Trp Ile Ser Gln Phe Leu Gln Xaa Leu
             5               10              15

Ala Ile Thr Ala Val Gln Xaa Xaa Leu Val Xaa Ala Ala Met Glu Lys
         20              25                  30

Phe Thr Xaa Ala His Thr Val Leu Arg Met Ser Leu Xaa Xaa Val Leu
         35              40              45

Gln Tyr Asn Leu Leu Ser Tyr Ser Met Lys Phe Ile Ala Thr Leu Val
    50              55              60

TABLE 4-continued

DNA and amino acid sequence of clone S34

| Leu 65 | Arg | Ser | Met | Val | Gln 70 | Phe | Thr | Leu | Asp | Ile 75 | Lys | Leu | Gln | Leu | Ile 80 |
| Ser | Xaa | Gln | His | Phe 85 | Leu | Leu | Gln | Leu | Glu 90 | Pro | Gln | Asp | Asn | Gln 95 | Gln |
| Leu | Leu | Gln | Leu 100 | Glu | Val | Gln | Ala | Asn 105 | Gln | Leu | Leu | Leu | Pro 110 | Leu | Ser |
| Lys | Ala | Thr 115 | Thr | Thr | Thr | Thr | Thr 120 | Leu | Asn | Pro | Ile | Ile 125 | Thr | Thr | Thr |
| Thr | Gln 130 | Lys | Pro | Thr | Thr | Thr 135 | Thr | Thr | Lys | Val 140 | Pro | Gly | Lys | Pro |
| Pro 145 | Ile | Ala | Thr | Thr | Thr 150 | Thr | Thr | Leu | Lys | Pro 155 | Ile | Val | Thr | Thr | Thr 160 |
| Thr | Thr | Lys | Ala | Thr 165 | Thr | Thr | Thr | Thr | Thr 170 | Val | Pro | Thr | Thr 175 | Thr |
| Thr | Thr | Thr | Lys 180 | Arg | Asp | Glu | Met | Thr 185 | Thr | Thr | Thr | Thr | Pro 190 | Leu | Pro |
| Asp | Ile | Gly 195 | Asp | Ile | Glu | Ile | Thr 200 | Pro | Ile | Pro | Ile | Glu 205 | Lys | Met | Leu |
| Asp | Lys 210 | Tyr | Thr | Arg | Met | Ile 215 | Tyr | Asp | Tyr | Asn | Ser 220 | Gly | Leu | Leu | Leu |
| Asp 225 | Ser | Asn | Asp | Glu | Pro 230 | Ile | Pro | Gly | Ser | Gln 235 | Ala | Gly | Gln | Ile | Ala 240 |
| Asp | Thr | Ser | Asn | Leu 245 | Phe | Pro | Gly | Ser | Asn 250 | Ser | Gln | Glu | Tyr | Trp 255 | Phe |
| Thr | Asn | Xaa | Ser 260 | Asn | Gly | Trp | Ser | Ser 265 | Ile | Xaa | Ser | Lys | Ile 270 | Arg | Xaa |
| Phe | Ser | Thr 275 | Ser | Ile | Tyr | Gln | Ser 280 | Asn | Asn | Val | Trp | Phe 285 | Ile | Gly | Ile |
| Ile | Ser 290 | Cys | Cys | Xaa | Glu | Phe 295 | Asp | Ser | Xaa | Tyr | Xaa 300 | Xaa | Asn | Tyr | Gly |
| Leu 305 | Pro | Ile | Asp | Thr | Leu 310 | Thr | Gly | Tyr | Pro | Leu 315 | Asp | Pro | Val | Ser | Leu 320 |
| Ile | Pro | Phe | Asn | Pro 325 | Glu | Thr | Gly | Glu | Leu 330 | Phe | Val | Gln | Tyr | Gln 335 | Met |
| Arg | Xaa | Xaa | Met 340 | Glu | Gln | Leu | Gln | Val 345 | Leu | Phe | Gln | Glu | Phe 350 | Leu | Gln |
| Val | Ser | His 355 | Tyr | Tyr | Leu | Arg | Asn 360 | Arg | Ser | | | | | | |

SEQUENCE DESCRIPTION: SEQ ID No. 27:

```
GCGAGTTCCC AGATAGAAGT TTGGATTTCA CAATTCCTCC AGTAGCTGGC CATAACAGCT    60

GTTCAATAAT AGTTGGTGTG AGCGGCGATG GAAAAATTCA CGTAAGCCCA TACGGTTCTA   120

AGGATGTCTC TCTAATAAGT GCTCCAATAC AACCTTCTGA GTTATTCAAT GAAGTTTATT   180

GCGACACTTG TACTGCGAAG TATGGTGCAA TTCACTCTGG ATATCAAACT TCAGCTGATT   240

TCGTAACAAC ACTTCCTACT ACAACTGGAG CCGCAGGACA ACCAACAACT ACTACAACTG   300

GAAGTCCAAG CAAACCAACT ACTACTACCA CTATCTAAGG CAACAACAAC CACAACAACT   360

CTTAATCCAA TCATTACAAC AACAACTCAA AAACCAACAA CAACAACAAC AACAAAGGTT   420
```

TABLE 4-continued

DNA and amino acid sequence of clone S34

```
CCAGGTAAGC CACCAATAGC CACAACAACA ACAACATTAA AGCCAATAGT TACAACAACA   480

ACAACAAAAG CAACAACAAC AACAACAACA ACAGTGCCAA CGACAACTAC TACTACCAAG   540

AGAGACGAAA TGACAACAAC AACGACACCA TTACCTGATA TCGGTGACAT TGAAATTACA   600

CCAATCCCAA TTGAAAAGAT GTTGGATAAG TACACAAGAA TGATTTATGA CTATAACAGT   660

GGTTTATTAT TAGACTCTAA TGATGAACCA ATTCCAGGTT CTCAAGCAGG ACAAATAGCT   720

GATACAAGCA ATTTATTCCC AGGTTCAAAC TCACAAGAGT ACTGGTTTAC CAATTGATCC   780

AATGGTTGGT CTTCCATTTG ATCCAAAATC AGGTAATTTA GTACATCCAT ATACCAATCA   840

AACAATGTCT GGTTTATCGG TATCATATCT TGCTGCTAAG AATTTGACAG TTGATACTGA   900

TGAAACTACG GTTACCAAT TGATACACTC ACTGGTTACC CATTGGATCC AGTCAGTTTG   960

ATTCCGTTCA ATCCAGAAAC TGGTGAATTG TTTGTCCAAT ATCAGATGAG ATAATGAATG  1020

GAACAATTGS AGGTATTGTT TCAGGAATTT CTGCAAGTGA GTCATTATTA TCTCAGAAAT  1080
CGCTCC                                                             1086
```

SEQUENCE DESCRIPTION: SEQ ID NO. 47:

```
CGC TCA AGG GTC TAT CTT CAA ACC TAA AGT GTT AAG GAG GTC ATC GAC CGG TAT TGT   57

CGA CAA GTT ATT ATC AAC CAC ACT CGC CGC TAC CTT TTT AAG TGC ATT CGG GTA TGC  114

CAA GAT TCC TAC AGA GAG ATT ATT CAC GAG GTT ATG TTG GAA GAC TCA ATA AGT TAC  171

TTC AAA TAA CGC TGT GAA CAT GAC GCT TCA TAC CAC GTT AAG TGA GAC CTA TAG TTT  228

GAA GTC GAC TAA AGC ATT GTT GTG AAG GAT GAT GTT GAC CTC GGC GTC CTG TTG GTT  285

GTT GAT GAT GTT GAC CTT CAG GTT CGT TTG GTT GAT GAT GAT GGT GAT AGA TTC CGT  342

TGT TGT TGG TGT TGT TGA GAA TTA GGT TAG TAA TGT TGT TGT TGA GTT TTT GGT TGT  399

TGT TGT TGT TGT TGT TTC CAA GGT CCA TTC GGT GGT TAT CGG TGT TGT TGT TGT TGT  456

AAT TTC GGT TAT CAA TGT TGT TGT TGT TGT TTT CGT TGT TGT TGT TGT TGT TGT TGT  513

CAC GGT TGC TGT TGA TGA TGA TGG TTC TCT CTG CTT TAC TGT TGT TGT TGC TGT GGT  570

AAT GGA CTA TAG CCA CTG TAA CTT TAA TGT GGT TAG GGT TAA CTT TTC TAC AAC CTA  627

TTC ATG TGT TCT TAC TAA ATA CTG ATA TTG TCA CCA AAT AAT AAT CTG AGA TTA CTA  684

CTT GGT TAA GGT CCA AGA GTT CGT CCT GTT TAT CGA CTA TGT TCG TTA AAT AAG GGT  741

CCA AGT TTG AGT GTT CTC ATG ACC AAA TGG TTA ACT AGG TTA CCA ACC AGA AGG TAA  798

ACT AGG TTT TAG TCC ATT AAA TCA TGT AGG TAT ATG GTT AGT TTG TTA CAG ACC AAA  855
```

| TABLE 4-continued | |
|---|---|
| DNA and amino acid sequence of clone S34 | |
| TAG CCA TAG TAT AGA ACG ACG ATT CTT AAA CTG TCA ACT ATG ACT ACT TTG ATG CCA | 912 |
| AAT GGT TAA CTA TGT GAG TGA CCA ATG GGT AAC CTA GGT CAG TCA AAC TAA GGC AAG | 969 |
| TTA GGT CTT TGA CCA CTT AAC AAA CAG GTT ATA GTC TAC TCT ATT ACT TAC CTT GTT | 1026 |
| AAC GTC CAT AAC AAA GTC CTT AAA GAC GTT CAC TCA GTA ATA ATA GAG TCT TTA GCG | 1083 |
| AGG | 1086 |

SEQUENCE DESCRIPTION: SEQ ID NO. 35:

Arg Thr Gly Leu Tyr Phe Asn Pro Asn Xaa Leu Glu Glu Leu Leu Gln Gly Tyr
                5                   10                  15
Cys Ser Asn Leu Leu Leu Gln His Ser Arg Arg His Phe Phe Glu Arg Leu Gly
    20              25                  30                  35
Met Arg Asn Xaa Pro His Arg Glu Leu Leu His Glu Leu Val Val Lys Gln Thr
            40              45                  50
Ile Xaa His Leu Lys Asn Arg Cys Lys Tyr Gln Ser Thr His His Leu Glu Ser
55              60                  65                  70
Gln Ile Asp Phe Lys Leu Gln Asn Arg Leu Leu Val Glu Xaa Xaa Leu Gln Leu
        75                  80                  85                  90
Arg Leu Val Val Leu Leu Xaa Xaa Leu Gln Phe Asp Leu Cys Val Leu Xaa Xaa
                95                  100                 105
Xaa Trp Xaa Arg Leu Cys Cys Cys Gly Cys Cys Ser Lys Ile Trp Asp Asn Cys
    110                 115                 120                 125
Cys Cys Ser Leu Phe Trp Cys Cys Cys Cys Cys Leu Asn Trp Thr Leu Trp
            130             135                 140
Trp Tyr Gly Cys Cys Cys Cys Cys Xaa Leu Trp Tyr Asn Cys Cys Cys Cys Cys
145             150                 155                 160
Phe Cys Cys Cys Cys Cys Cys Cys Cys His Trp Arg Cys Ser Ser Ser Gly Leu
        165                 170                 175                 180
Ser Val Phe His Cys Cys Cys Arg Cys Trp Xaa Arg Ile Asp Thr Val Asn Phe
            185                 190                 195
Asn Cys Trp Asp Trp Asn Phe Leu His Gln Ile Leu Val Cys Ser His Asn Ile
    200                 205                 210                 215
Val Ile Val Thr Thr Xaa Xaa Xaa Val Arg Ile Ile Phe Trp Asn Trp Thr Arg
                220                 225                 230
Leu Cys Ser Leu Tyr Ser Ile Cys Ala Ile Xaa Glu Trp Thr Xaa Val Xaa Leu
235                 240                 245                 250
Leu Val Pro Lys Gly Ile Ser Gly Ile Thr Pro Arg Gly Asn Ser Gly Phe Asp
        255                 260                 265                 270
Pro Leu Lys Thr Cys Gly Tyr Val Leu Xaa Val Ile Asp Pro Lys Asp Thr Asp
            275                 280                 285
Tyr Arg Ala Ala Leu Phe Lys Val Thr Ser Val Ser Ser Val Val Thr Xaa Trp
    290                 295                 300                 305
Asn Ile Cys Glu Ser Thr Val Trp Gln Ile Trp Asp Thr Gln Asn Arg Glu Ile
                310                 315                 320
Trp Phe Ser Thr Phe Gln Lys Asp Leu Ile Leu His Ser Leu Ser His Phe Leu
325                 330                 335                 340
Gln Leu Tyr Gln Lys Leu Phe Lys Gln Leu His Thr Met Ile Ile Glu Ser Ile
        345                 350                 355                 360
Ala Gly
362

SEQUENCE DESCRIPTION: SEQ ID NO. 36:

TABLE 4-continued

DNA and amino acid sequence of clone S34

| Ser | Asn | Gly | Ser | Leu 5 | Leu | Lys | Ser | Lys | Val 10 | Ile | Gly | Gly | Thr | Ala 15 | Pro | Trp | Leu | Leu |
| Gln 20 | Glu | Ile | Ile | Thr | Pro 25 | Thr | Leu | Pro | Ser | Pro 30 | Phe | Ile | Xaa | Thr | Leu 35 | Gly | Tyr | Pro |
| Glu | Leu 40 | Ser | Thr | Glu | Arg | Ile 45 | Leu | Ala | Gly | Ile | Cys 50 | Gly | Glu | Ser | Asn | Asn 55 | Leu | Ser |
| Thr | Xaa | Gln 60 | Ser | Val | Gln | Val | Ala 65 | Phe | Tyr | Pro | Ala | Ile 70 | Xaa | Glu | Pro | Tyr | Xaa 75 | Val |
| Glu | Ala | Ser | Lys 80 | Thr | Val | Val | Ser | Gly 85 | Val | Val | Val | Pro | Ala 90 | Ala | Pro | Cys | Gly | Val 95 |
| Val | Val | Val | Val | Pro 100 | Leu | Gly | Leu | Leu | Gly 105 | Val | Val | Val | Val | Val 110 | Ile | Xaa | Pro | Leu |
| Leu 115 | Leu | Trp | Leu | Leu | Glu 120 | Xaa | Asp | Leu | Xaa | Xaa 125 | Leu | Leu | Leu | Glu | Phe 130 | Val | Leu | Leu |
| Leu | Leu 135 | Leu | Leu | Leu | Pro | Glu 140 | Leu | Tyr | Ala | Val | Leu 145 | Leu | Trp | Leu | Leu | Leu 150 | Leu | Met |
| Leu | Ala | Leu 155 | Leu | Xaa | Leu | Leu | Leu 160 | Leu | Leu | Leu | Leu | Leu 165 | Leu | Leu | Leu | Leu | Leu 170 | Leu |
| Ala | Leu | Ser | Leu 175 | Xaa | Xaa | Xaa | Trp | Ser 180 | Leu | Arg | Phe | Ser | Leu 185 | Leu | Leu | Ser | Val | Met 190 |
| Val | Gln | Tyr | Arg | His 195 | Cys | Gln | Phe | Xaa | Val 200 | Leu | Gly | Leu | Gln | Phe 205 | Ser | Thr | Pro | Tyr |
| Thr 210 | Cys | Leu | Phe | Ser | Lys 215 | His | Ser | Tyr | Cys | His 220 | Asn | Ile | Ile | Leu | Ser 225 | Xaa | His | His |
| Val | Leu 230 | Glu | Leu | Asn | Glu | Leu 235 | Leu | Val | Phe | Leu | Gln 240 | Tyr | Leu | Cys | Asn | Ile 245 | Gly | Leu |
| Asn | Leu | Ser 250 | Val | Leu | Thr | Ser | Thr 255 | Xaa | Trp | Asn | Ile | Trp 260 | His | Asn | Thr | Lys | Trp 265 | Lys |
| Ile | Trp | Phe | Xaa 270 | Thr | Ile | Xaa | Tyr | Met 275 | Trp | Ile | Gly | Ile | Leu 280 | Cys | His | Arg | Thr | Xaa 285 |
| Arg | Tyr | Xaa | Ile | Lys 290 | Ser | Ser | Leu | Ile | Gln 295 | Cys | Asn | Ile | Ser | Ile 300 | Phe | Ser | Arg | Asn |
| Val 305 | Leu | Gln | Tyr | Val | Xaa 310 | Gln | Asn | Gly | Met | Pro 315 | Asp | Leu | Xaa | Asn | Ser 320 | Glu | Thr | Xaa |
| Asp | Leu 325 | Phe | Gln | His | Ile | Thr 330 | Gln | Gly | Ile | Asp | Ser 335 | Ser | Ile | Ile | Phe | Pro 340 | Val | Ile |
| Ala | Pro | Ile 345 | Thr | Glu | Pro | Ile | Glu 350 | Ala | Leu | Ser | Asp | Asn 355 | Asn | Asp | Xaa | Phe | Asp 360 | Ser 361 |

SEQUENCE DESCRIPTION: SEQ ID NO. 37:

| Leu | Glu | Trp | Ile | Ser 5 | Thr | Gln | Ile | Glu | Cys 10 | Asn | Arg | Trp | Tyr | Ser 15 | Ala | Met | Val | Ala |
| Thr 20 | Xaa | Tyr | Tyr | Asn | Thr 25 | His | Ala | Ala | Ile | Ser 30 | Phe | Asn | Val | Tyr | Ala 35 | Trp | Val | Thr |
| Arg | Leu 40 | Ile | Asp | Arg | Xaa | Tyr 45 | Thr | Ser | Trp | Tyr | Leu 50 | Arg | Arg | Leu | Xaa | Glu 55 | Ile | Phe |
| Asn | Ile | Ala 60 | Val | Ser | Thr | Ser | Arg 65 | Leu | Ile | Thr | Cys | Asn 70 | Val | Arg | Ser | Ile | Leu 75 | Ser |
| Xaa | Ser | Ile | Glu 80 | Tyr | Cys | Cys | Lys | Arg 85 | Ser | Cys | Ser | Ser | Gly 90 | Cys | Ser | Leu | Trp | Cys 95 |
| Ser | Ser | Cys | Ser | Ser 100 | Thr | Trp | Ala | Phe | Trp 105 | Ser | Ser | Ser | Gly | Ser 110 | Asp | Leu | Ala | Val |
| Val 115 | Val | Val | Val | Val | Arg 120 | Leu | Gly | Ile | Met | Val 125 | Val | Val | Val | Xaa | Phe 130 | Gly | Val | Val |

TABLE 4-continued

DNA and amino acid sequence of clone S34

| | | | | | | | | | | | | | | | | | | |
|---|---|---|---|---|---|---|---|---|---|---|---|---|---|---|---|---|---|---|
| Val | Val 135 | Val | Val | Phe | Thr | Gly 140 | Pro | Leu | Gly | Gly | Ile 145 | Ala | Val | Val | Val | Val 150 | Val | Asn |
| Phe | Gly | Ile 155 | Thr | Val | Val | Val 160 | Val | Phe | Ala | Val | Val 165 | Val | Val | Val | Val | Val 170 | Thr | |
| Gly | Val | Val | Val 175 | Val | Val | Val | Leu | Leu 180 | Ser | Ser | Ile | Val | Val 185 | Val | Val | Val | Gly | Asn 190 |
| Gly | Ser | Ile | Pro | Ser 195 | Met | Ser | Ile | Val | Gly 200 | Ile | Gly | Ile | Ser | Phe 205 | Ile | Asn | Ser | Leu |
| Tyr 210 | Val | Leu | Ile | Ile | Xaa 215 | Ser | Xaa | Leu | Leu | Pro 220 | Lys | Asn | Asn | Ser | Glu 225 | Leu | Ser | Ser |
| Gly | Ile 230 | Gly | Pro | Glu | Xaa | Ala 235 | Pro | Cys | Ile | Ala | Ser 240 | Val | Leu | Leu | Lys | Asn 245 | Gly | Pro |
| Glu | Phe | Glu 250 | Cys | Ser | Tyr | Gln | Asn 255 | Val | Leu | Gln | Asp | Leu 260 | Pro | Gln | Asp | Glu | Met 265 | Gln |
| Asp | Leu | Ile | Leu 270 | Tyr | Asn | Leu | Val | Asp 275 | Met | Tyr | Trp | Asp | Phe 280 | Leu | Thr | Gln | Asn | Ile 285 |
| Pro | Ile | Met | Asp | Gln 290 | Gln | Xaa | Ser | Asn | Ser 295 | Leu | Gln | Tyr | Gln | His 300 | Phe | Xaa | Pro | Lys |
| Gly 305 | Ile | Ser | Val | Ser | Val 310 | Pro | Xaa | Gly | Asn | Ser 315 | Gly | Thr | Leu | Lys | Ile 320 | Gly | Asn | Leu |
| Gly | Ser 325 | Val | Pro | Ser | Asn | Asn 330 | Thr | Trp | Tyr | Xaa | Ile 335 | Leu | Tyr | His | Ile | Ser 340 | Cys | Asn |
| Cys | Thr | Asn 345 | Asn | Xaa | Ser | Asn | Arg 350 | Cys | Thr | Leu | Xaa | Xaa 355 | Xaa | Arg | Leu | Phe | Arg 360 | Glu 361 |

The longest open reading frame in the 1087 nucleotides of the insert, 176 amino acids, starts at nucleotide 247 (CAA CAC . . . ) in a phase 1 translation. It starts at the first nucleotide and proceeds left to right.

This sequence was obtained as described in Example 17 by reading into the DNA insert and generating sequencing primers. Table 5 below provides the enzyme restriction map of this clone, generated by computer from the sequence itself.

Example 19

DNA Sequence of Clone S19

A partial DNA nucleotide sequence of the *C. parvum* insert of clone S19 was determined as described for

TABLE 6

DNA and amino acid sequences of clone S19

SEQUENCE DESCRIPTION: SEQ ID NO. 9:

| Phe | Arg | Gln | Leu | Met | Pro | Asn | Asn | Gln | Leu | Arg | Leu | Ala | Arg | Gly | Gly |
|---|---|---|---|---|---|---|---|---|---|---|---|---|---|---|---|
| | | | | 5 | | | | | 10 | | | | | 15 | |

| Asn | Leu | Cys | Xaa | Gln | Val | Gln | Glu | Ile | Ser | Gln | Glu | Ser | Arg | Met | Leu |
|---|---|---|---|---|---|---|---|---|---|---|---|---|---|---|---|
| | | | 20 | | | | | 25 | | | | | 30 | | |

| His | Xaa | Thr | Gln | Gln | Pro | Val | Pro | Gln | Val | Cys | Xaa | Thr | Val |
|---|---|---|---|---|---|---|---|---|---|---|---|---|---|
| | | 35 | | | | | 40 | | | | | 45 | |

SEQUENCE DESCRIPTION: SEQ ID NO. 10:

| Ile | Pro | Ala | Ile | Asn | Ala | Lys | Gln | Ser | Ala | Gln | Ile | Ser | Xaa | Arg | Trp |
|---|---|---|---|---|---|---|---|---|---|---|---|---|---|---|---|
| | | | | 5 | | | | | 10 | | | | | 15 | |

| Lys | Ser | Met | Leu | Thr | Ser | Pro | Gly | Asp | Lys | Pro | Gly | Val | Ala | Asn | Val |
|---|---|---|---|---|---|---|---|---|---|---|---|---|---|---|---|
| | | | 20 | | | | | 25 | | | | | 30 | | |

| Ala | Leu | Asn | Ser | Ala | Ala | Ser | Ser | Thr | Ser | Val | Leu | Asp | Ser |
|---|---|---|---|---|---|---|---|---|---|---|---|---|---|
| | | 35 | | | | | 40 | | | | | 45 | |

SEQUENCE DESCRIPTION: SEQ ID NO. 11:

| Asn | Ser | Gly | Asn | Xaa | Cys | Gln | Thr | Ile | Ser | Ser | Asp | Xaa | Leu | Glu | Val |
|---|---|---|---|---|---|---|---|---|---|---|---|---|---|---|---|
| | | | | 5 | | | | | 10 | | | | | 15 | |

| Glu | Ile | Tyr | Val | Asn | Lys | Ser | Arg | Arg | Xaa | Ala | Arg | Ser | Arg | Glu | Cys |
|---|---|---|---|---|---|---|---|---|---|---|---|---|---|---|---|
| | | | 20 | | | | | 25 | | | | | 30 | | |

| Cys | Ile | Lys | Leu | Ser | Ser | Gln | Phe | His | Lys | Cys | Val | Arg | Gln | Tyr |
|---|---|---|---|---|---|---|---|---|---|---|---|---|---|---|
| | | 35 | | | | | 40 | | | | | 45 | | |

SEQUENCE DESCRIPTION: SEQ ID NO. 29:

AATTCCGGCA ATTAATGCCA ACAATCAGC TCAGATTAGC TAGAGGTGGA AATCTATGTT   60

AACAAGTCCA GGAGATAAGC CAGGAGTCGC GAATGTTGCA TTAAACTCAG CAGCCAGTTC   120

CACAAGTGTG TTAGACAGTA T   141

SEQUENCE DESCRIPTION: SEQ ID NO. 48:

TTA AGG CCG TTA ATT ACG GTT TGT TAG TCG AGT CTA ATC GAT CTC CAC CT T TAG ATA   57

CAA TTG TTC AGG TCC TCT ATT CGG TCC TCA GCG CTT ACA ACG TAA TTT GAG TCG TCG   114

GTC AAG GTG TTC ACA CAA TCT GTC ATA   141

SEQUENCE DESCRIPTION: SEQ ID NO. 38:

| Ile | Gly | Ala | Ile | Leu | Ala | Leu | Cys | Asp | Ala | Xaa | Ile | Leu | Xaa | Leu | His | Phe | Asp | Ile |
|---|---|---|---|---|---|---|---|---|---|---|---|---|---|---|---|---|---|---|
| | | | | 5 | | | | | 10 | | | | | 15 | | | | |

| Asn | Val | Leu | Gly | Pro | Ser | Leu | Gly | Pro | Thr | Ala | Phe | Thr | Ala | Asn | Phe | Glu | Ala | Ala |
|---|---|---|---|---|---|---|---|---|---|---|---|---|---|---|---|---|---|---|
| 20 | | | | | 25 | | | | | 30 | | | | | 35 | | | |

| Leu | Glu | Val | Leu | Thr | Asn | Ser | Leu | Ile |
|---|---|---|---|---|---|---|---|---|
| | 40 | | | | | 45 | | 47 |

SEQUENCE DESCRIPTION: SEQ ID NO. 39:

| Asn | Arg | Cys | Asn | Ile | Gly | Phe | Leu | Xaa | Ser | Leu | Asn | Ala | Leu | Pro | pro | Phe | Arg | His |
|---|---|---|---|---|---|---|---|---|---|---|---|---|---|---|---|---|---|---|
| | | | | 5 | | | | | 10 | | | | | 15 | | | | |

| Xaa | Cys | Thr | Thr | Ser | Ile | Leu | Trp | Ser | Asp | Arg | Ile | Asn | Cys | Xaa | Val | Xaa | Cys | Gly |
|---|---|---|---|---|---|---|---|---|---|---|---|---|---|---|---|---|---|---|
| 20 | | | | | 25 | | | | | 30 | | | | | 35 | | | |

| Thr | Gly | Cys | Thr | His | Xaa | Val | Thr |
|---|---|---|---|---|---|---|---|
| | 40 | | | | | 45 | 46 |

SEQUENCE DESCRIPTION: SEQ ID NO. 40:

TABLE 6-continued

DNA and amino acid sequences of clone S19

| | | | | | | | | | | | | | | | | |
|---|---|---|---|---|---|---|---|---|---|---|---|---|---|---|---|---|
| Glu | Pro | Leu | Xaa | His | Trp | Val | Ile | Leu | Glu | Ser | Xaa | Ser | Ser | Thr | Ser | Ile | Xaa | Thr |
| | | | | 5 | | | | | 10 | | | | | 15 | | | | |
| Leu | Leu | Asp | Leu | Leu | Tyr | Ala | Leu | Leu | Arg | Ser | His | Gln | Met | Leu | Ser | Leu | Leu | Trp |
| 20 | | | | | 25 | | | | | 30 | | | | | 35 | | | |
| Asn | Trp | Leu | His | Thr | Leu | Cys | Tyr | | | | | | | | | | | |
| | 40 | | | | | 45 | 46 | | | | | | | | | | | |

This sequence was obtained using universal primers (US Biochemical). Table 7 below provides the enzyme restriction map of this clone generated from the sequence.

TABLE 7

Enzyme Restriction Map of DNA from Clone S19

```
                                              88 BstU I              114 Bsr I
                              40 Rma I        87 Nru I               110 Fnu4H I
              11 Ase I        40 Mae I   58 Hpa I    84 Ple I        110 Bst71 I
    5 Hpa II         19 Tth111 II   40 Bfa I  58 HinC II  84 Hinf I   110 Bbv I
    |   |          |            |         |      | ||             |   |
    ┌───────────────────────────────────────────────────────────────────┐
    └───────────────────────────────────────────────────────────────────┘
      4/20-S19 sequence             141 base pairs         Unique Sites
```

The correct reading frame for the 141 nucleotides of the insert remains to be determined. Antibodies elicited by immunization with *C. parvum* that bind to the 68 and 95 kD peptide bands of the *C. parvum* lysate also bind to the S19 polypeptide.

Example 20

DNA Sequence of Clone S7

The DNA nucleotide sequence of the *C. parvum* insert of clone S7 was determined as described for the S34 clone. The DNA sequence obtained and that of its complementary stand are shown in Table 8 below as are the six possible amino acid sequences deduced therefrom.

TABLE 8

DNA and amino acid sequences of clone S7

SEQUENCE DESCRIPTION: SEQ ID NO. 15:

| | | | | | | | | | | | | | | |
|---|---|---|---|---|---|---|---|---|---|---|---|---|---|---|
| Gly | Asn | Tyr | Pro | Ser | Leu | Leu | Leu | Arg | Asp | Ile | Thr | Glu | Asp | Ile | Xaa |
| | | | | 5 | | | | | 10 | | | | | 15 | |
| Val | Gln | Asn | Lys | Leu | Thr | Leu | Asn | Gln | Xaa | Ile | Gln | Phe | Val | Asn | Leu |
| | | | 20 | | | | | 25 | | | | | 30 | | |
| Ile | Xaa | Phe | Pro | Val | Lys | Xaa | Asn | Ile | Phe | Tyr | Lys | Ile | Arg | Tyr | Tyr |
| | | 35 | | | | | 40 | | | | | 45 | | | |
| Ser | Ile | Leu | Lys | Tyr | Thr | Ile | Val | Tyr | Xaa | Asn | Glu | Tyr | Ile | Ser | Xaa |
| | 50 | | | | | 55 | | | | | 60 | | | | |
| Lys | Val | Ser | Thr | Lys | Leu | Tyr | Cys | Xaa | Ser | Cys | Tyr | Gly | Arg | Trp | Phe |
| 65 | | | | | 70 | | | | | 75 | | | | | 80 |
| Ile | Gln | Glu | Gly | Leu | Leu | Glu | Arg | Leu | Gln | Arg | Lys | Ile | Arg | Cys | Ile |
| | | | | 85 | | | | | 90 | | | | | 95 | |
| Val | Leu | Leu | Ser | Ile | Lys | Leu | His | Ile | Cys | Met | Ser | Ile | Xaa | Asn | Leu |
| | | | 100 | | | | | 105 | | | | | 110 | | |

TABLE 8-continued

| DNA and amino acid sequences of clone S7 |
|---|

Ser Ile Gln Ser Ser Thr Lys Arg Leu Xaa Glu Ile Gly Ser Thr Ala
     115          120          125

Pro Leu Val Cys Ser Val Asp Ser Gln Tyr Ser His Ala Ala Trp Arg
130               135         140

Arg Thr Pro Leu Glu Gln Gly Gly Ile Gly Pro Val Asn Phe Pro Leu
145              150          155         160

Ile Ser Asp Ser Ser His Ser Ile Ser Lys Asn Tyr Gly Val Leu Ser
          165          170          175

Arg Gly Arg Arg Tyr Cys Ser Gln Arg Phe Ile His His Xaa Gln Gly
        180          185          190

Gly Ser Arg Cys Ser Phe Xaa Ser Asn Leu Xaa Leu Thr Ile Arg Lys
     195          200          205

Ile Ser Arg Arg Asn Ser Thr Cys Tyr Xaa Cys Thr Ser Ile His Xaa
   210             215          220

Asn Leu Trp Xaa Ser Leu Pro Ser Lys Leu Glu Glu Gly Pro Lys Arg
225              230          235         240

Asn Val Ser Tyr Ser Xaa Arg Cys Phe Gln Leu Ser Xaa Gly Leu Ile
         245          250          255

Leu Glu Xaa Phe Asn Phe Ser Asn Glu Pro Asn Phe Phe Leu Ile Xaa
        260          265          270

Leu Phe Leu Cys Ser Tyr Lys Ser Asp Ala Asn Glu Tyr Arg Arg Leu
     275          280          285

His Ile Xaa Ile Leu Cys Gly Asp Xaa Ile Val Glu Xaa Val Gln Ile
   290             295          300

Asn Pro Gly Val Val Asn Val Val Leu Asn Phe Cys Asn Leu Ser Phe
305              310          315         320

Phe Phe Leu Leu Thr Tyr Leu Ser Trp Cys Xaa Gln Ser Ser Ile Arg
         325          330          335

Asn His Tyr Ser Ser Ser Lys Ala Gly Arg Arg Ser Pro Xaa
         340          345          350

SEQUENCE DESCRIPTION: SEQ ID NO. 16:

Arg Glu Leu Pro Leu Ile Ile Ala Ser Arg Tyr Asn Xaa Gly Tyr Leu
          5                 10          15

Gly Thr Lys Xaa Ile Asp Leu Glu Ser Ile Asn Ser Ile Cys Glu Phe
        20           25          30

Asn Leu Ile Ser Ser Lys Val Lys Tyr Phe Leu Gln Asn Ser Leu Leu
     35          40          45

Phe His Phe Lys Val Tyr Asn Ser Leu Leu Lys Xaa Val His Xaa Leu
   50             55          60

Glu Ser Xaa His Gln Thr Leu Leu Leu Lys Leu Leu Trp Gln Met Val
65               70          75         80

His Ser Arg Arg Ser Pro Xaa Ala Thr Thr Glu Glu Asn Thr Leu Tyr
        85           90          95

Cys Ser Ser Ile His Xaa Thr Ser His Leu Tyr Val His Leu Lys Ser
         100          105         110

Xaa His Ser Ile Lys His Lys Lys Thr Leu Arg Asn Trp Glu Tyr Ser
     115          120         125

Ser Ser Arg Val Leu Ser Xaa Phe Ser Ile Leu Pro Cys Cys Met Glu
   130          135         140

Thr Tyr Ser Ser Xaa Thr Arg Trp Asn Trp Thr Ser Gln Phe Pro Thr
145             150          155         160

Tyr Leu Xaa Leu Ile Ser Phe Asn Xaa Gln Glu Leu Trp Cys Thr Phe
         165          170         175

TABLE 8-continued

DNA and amino acid sequences of clone S7

Ser Arg Lys Lys Val Leu Leu Ser Glu Val Tyr Ser Ser Leu Thr Arg
        180                 185                 190

Arg Val Ala Leu Phe Val Leu Lys Xaa Ser Met Thr Tyr His Xaa Glu
        195                 200                 205

Asp Gln Ser Lys Lys Leu Tyr Val Leu Leu Met His Phe Asn Ser Leu
        210                 215                 220

Lys Pro Met Val Lys Phe Ala Gln Gln Thr Gly Arg Arg Ala Lys Lys
225                 230                 235                 240

Glu Cys Gln Leu Leu Met Lys Val Phe Pro Val Ile Leu Arg Thr His
                245                 250                 255

Phe Arg Met Ile Xaa Phe Phe Lys Xaa Thr Lys Phe Phe Phe Asn Leu
            260                 265                 270

Thr Phe Phe Met Xaa Leu Xaa Ile Arg Cys Lys Xaa Val Ser Ser Ser
        275                 280                 285

Pro His Leu Asp Pro Leu Trp Arg Leu Asp Cys Gly Ile Gly Ala Asn
    290                 295                 300

Lys Pro Trp Ser Cys Xaa Cys Ser Val Lys Phe Leu Xaa Phe Ile Phe
305                 310                 315                 320

Phe Phe Leu Ile Asn Leu Pro Phe Leu Val Leu Ala Val Phe Tyr Xaa
                325                 330                 335

Lys Ser Leu Leu Phe Phe Gln Gly Arg Lys Lys Val Ser Leu
            340                 345                 350

SEQUENCE DESCRIPTION: SEQ ID NO. 17:

Pro Gly Ile Thr Pro His Tyr Cys Phe Glu Ile Xaa Leu Arg Ile Phe
            5                   10                  15

Arg Tyr Lys Ile Asn Xaa Pro Xaa Ile Asn Lys Phe Asn Leu Xaa Ile
            20                  25                  30

Xaa Phe Asn Phe Gln Xaa Ser Glu Ile Phe Phe Thr Lys Phe Ala Ile
        35                  40                  45

Ile Pro Phe Xaa Ser Ile Gln Xaa Ser Ile Glu Met Ser Thr Leu Val
    50                  55                  60

Arg Lys Leu Ala Pro Asn Phe Thr Ala Glu Ala Val Met Ala Asp Gly
65                  70                  75                  80

Ser Phe Lys Lys Val Ser Leu Ser Asp Tyr Arg Gly Lys Tyr Val Val
                85                  90                  95

Leu Phe Phe Tyr Pro Leu Asn Phe Thr Phe Val Cys Pro Ser Glu Ile
            100                 105                 110

Leu Ala Phe Asn Gln Ala Gln Lys Asp Phe Glu Lys Leu Gly Val Gln
        115                 120                 125

Leu Leu Ser Cys Ala Gln Leu Ile Leu Asn Thr Pro Met Leu His Gly
    130                 135                 140

Asp Val Leu Leu Leu Asn Lys Val Glu Leu Asp Gln Ser Ile Ser His
145                 150                 155                 160

Leu Ser Leu Thr His Leu Ile Gln Leu Ala Arg Thr Met Val Tyr Phe
                165                 170                 175

Leu Glu Glu Glu Gly Ile Ala Leu Arg Gly Leu Phe Ile Ile Asp Lys
            180                 185                 190

Glu Gly Arg Val Val Arg Ser Glu Val Ile Tyr Asp Leu Pro Leu Gly
        195                 200                 205

Arg Ser Val Glu Glu Thr Leu Arg Val Ile Asp Ala Leu Gln Phe Thr
    210                 215                 220

Glu Thr Tyr Gly Glu Val Cys Pro Ala Asn Trp Lys Lys Gly Gln Lys
225                 230                 235                 240

TABLE 8-continued

DNA and amino acid sequences of clone S7

| | | | | | | | | | | | | | |
|---|---|---|---|---|---|---|---|---|---|---|---|---|---|
| Gly | Met | Ser | Ala | Thr 245 | His | Glu | Gly | Val | Ser 250 | Ser | Tyr | Leu | Lys | Asp 255 | Ser |
| Phe | Xaa | Asn | Asp 260 | Leu | Ile | Phe | Gln | Met 265 | Asn | Gln | Ile | Phe | Phe 270 | Xaa | Ser |
| Asp | Phe | Phe 275 | Tyr | Val | Val | Ile | Asn 280 | Gln | Met | Gln | Met | Ser 285 | Ile | Val | Val |
| Ser | Thr 290 | Ser | Arg | Ser | Ser | Val 295 | Ala | Thr | Arg | Leu | Trp 300 | Asn | Arg | Cys | Lys |
| Xaa 305 | Thr | Leu | Glu | Leu | Leu 310 | Met | Xaa | Cys | Xaa | Ile 315 | Phe | Val | Ile | Tyr | Leu 320 |
| Phe | Phe | Ser | Tyr | Xaa 325 | Leu | Thr | Phe | Leu | Gly 330 | Val | Ser | Ser | Leu 335 | Leu |
| Glu | Ile | Ile | Thr 340 | Leu | Leu | Pro | Arg | Pro 345 | Glu | Glu | Gly | Leu | Leu 350 | Glu |

SEQUENCE DESCRIPTION: SEQ ID NO. 31:

| | | | | | | |
|---|---|---|---|---|---|---|
| CCGGGAATTA | CCCCTCATTA | TTGCTTCGAG | ATATAACTGA | GGATATTTAG | GTACAAAATA | 60 |
| AATTGACCTT | GAATCAATAA | ATTCAATTTG | TGAATTTAAT | TTAATTTCCA | GTAAAGTGAA | 120 |
| ATATTTTTA | CAAAATTCGC | TATTATTCCA | TTTTAAAGTA | TACAATAGTC | TATTGAAATG | 180 |
| AGTACATTAG | TTAGAAAGTT | AGCACCAAAC | TTTACTGCTG | AAGCTGTTAT | GGCAGATGGT | 240 |
| TCATTCAAGA | AGGTCTCCTT | GAGCGACTAC | AGAGGAAAAT | ACGTTGTATT | GTTCTTCTAT | 300 |
| CCATTAAACT | TCACATTTGT | ATGTCCATCT | GAAATCTTAG | CATTCAATCA | AGCACAAAAA | 360 |
| GACTTTGAGA | AATTGGGAGT | ACAGCTCCTC | TCGTGTGCTC | AGTTGATTCT | CAATACTCCC | 420 |
| ATGCTGCATG | GAGACGTACT | CCTCTTGAAC | AAGGTGGAAT | TGGACCAGTC | AATTTCCCAC | 480 |
| TTATCTCTGA | CTCATCTCAT | TCAATTAGCA | AGAACTATGG | TGTACTTTCT | CGAGGAAGAA | 540 |
| GGTATTGCTC | TCAGAGGTTT | ATTCATCATT | GACAAGGAGG | GTCGCGTTGT | TCGTTCTGAA | 600 |
| GTAATCTATG | ACTTACCATT | AGGAAGATCA | GTCGAAGAAA | CTCTACGTGT | TATTGATGCA | 660 |
| CTTCAATTCA | CTGAAACCTA | TGGTGAAGTT | TGCCCAGCAA | ACTGGAAGAA | GGGCCAAAAA | 720 |
| GGAATGTCAG | CTACTCATGA | AGGTGTTTCC | AGTTATCTTA | AGGACTCATT | TTAGAATGAT | 780 |
| TTAATTTTTC | AAATGAACCA | AATTTTTTTT | TAATCTGACT | TTTTTTATGT | AGTTATAAAT | 840 |
| CAGATGCAAA | TGAGTATCGT | CGTCTCCACA | TCTAGATCCT | CTGTGGCGAC | TAGATTGTGG | 900 |
| AATAGGTGCA | AATAAACCCT | GGAGTTCTTA | ATGTAGTGTT | AAATTTTTGT | AATTTATCTT | 960 |
| TTTTTTTCTT | ATTAACTTAC | CTTTCTTGGT | GTTAGCAGTC | TTCTATTAGA | AATCATTACT | 1020 |
| CTTCTTCCAA | GGCCGGAAGA | AGGTCTCCTT | GAG | | | 1053 |

SEQUENCE DESCRIPTION: SEQ ID NO. 49:

TABLE 8-continued

DNA and amino acid sequences of clone S7

| | | | | | | | | | | | | | | | | | | | |
|---|---|---|---|---|---|---|---|---|---|---|---|---|---|---|---|---|---|---|---|
| GGC | CCT | TAA | TGG | GGA | GTA | ATA | ACG | AAG | CTC | TAT | ATT | GAC | TCC | TAT | AAA | TCC | ATG | TTT | 57 |
| TAT | TTA | ACT | GGA | ACT | TAG | TTA | TTT | AAG | TTA | AAC | ACT | TAA | ATT | AAA | TTA | AAG | GTC | ATT | 114 |
| TCA | CTT | TAT | AAA | AAA | TGT | TTT | AAG | CGA | TAA | TAA | GGT | AAA | ATT | TCA | TAT | GTT | ATC | AGA | 171 |
| TAA | CTT | TAC | TCA | TGT | AAT | CAA | TCT | TTC | AAT | CGT | GGT | TTG | AAA | TGA | CGA | CTT | CGA | CAA | 228 |
| TAC | CGT | CTA | CCA | AGT | AAG | TTC | TTC | CAG | AGG | AAC | TCG | CTG | ATG | TCT | CCT | TTT | ATG | CAA | 285 |
| CAT | AAC | AAG | AAG | ATA | GGT | AAT | TTG | AAG | TGT | AAA | CAT | ACA | GGT | AGA | CTT | TAG | AAT | CGT | 342 |
| AAG | TTA | GTT | CGT | GTT | TTT | CTG | AAA | CTC | TTT | AAC | CCT | CAT | GTC | GAG | GAG | AGC | ACA | CGA | 399 |
| GTC | AAC | TAA | GAG | TTA | TGA | GGG | TAC | GAC | GTA | CCT | CTG | CAT | GAG | GAG | AAC | TTG | TTC | CAC | 456 |
| CTT | AAC | CTG | GTC | AGT | TAA | AGG | GTG | AAT | AGA | GAC | TGA | GTA | GAG | TAA | GTT | AAT | CGT | TCT | 513 |
| TGA | TAC | CAC | ATG | AAA | GAG | CTC | CTT | CTT | CCA | TAA | CGA | GAG | TCT | CCA | AAT | AAG | TAG | TAA | 570 |
| CTG | TTC | CTC | CCA | GCG | CAA | CAA | GCA | AGA | CTT | CAT | TAG | ATA | CTG | AAT | GGT | AAT | CCT | TCT | 627 |
| AGT | CAG | CTT | CTT | TGA | GAT | GCA | CAA | TAA | CTA | CGT | GAA | GTT | AAG | TGA | CTT | TGG | ATA | CCA | 684 |
| CTT | CAA | ACG | GGT | CGT | TTG | ACC | TTC | TTC | CCG | GTT | TTT | CCT | TAC | AGT | CGA | TGA | GTA | CTT | 741 |
| CCA | CAA | AGG | TCA | ATA | GAA | TTC | CTG | AGT | AAA | ATC | TTA | CTA | AAT | TAA | AAA | GTT | TAC | TTG | 798 |
| GTT | TAA | AAA | AAA | ATT | AGA | CTG | AAA | AAA | ATA | CAT | CAA | TAT | TTA | GTC | TAC | GTT | TAC | TCA | 855 |
| TAG | CAG | CAG | AGG | TGT | AGA | TCT | AGG | AGA | CAC | CGC | TGA | TCT | AAC | ACC | TTA | TCC | ACG | TTT | 912 |
| ATT | TGG | GAC | CTC | AAC | AAT | TAC | ATC | ACA | ATT | TAA | AAA | CAT | TAA | ATA | GAA | AAA | AAA | AGA | 969 |
| ATA | ATT | GAA | TGG | AAA | GAA | CCA | CAA | TCG | TCA | GAA | GAT | AAT | CTT | TAG | TAA | TGA | GAA | GAA | 1026 |
| GGT | TCC | GGC | CTT | CTT | CCA | GAG | GAA | CTC | | | | | | | | | | | 1053 |

SEQUENCE DESCRIPTION: SEQ ID NO. 41:

Arg Ser Asn Gly Arg Met Ile Ala Glu Leu Tyr Leu Gln Pro Tyr Lys Pro Val Phe
            5                            10                        15

Tyr Ile Ser Arg Ser Asp Ile Phe Glu Ile Gln Ser Asn Leu Lys Ile Glu Leu Leu
20                    25                        30                  35

Thr Phe Tyr Lys Lys Cys Phe Glu Ser Asn Asn Trp Lys Leu Thr Tyr Leu Leu Arg
    40                        45                        50                        55

Asn Phe His Thr Cys Xaa Asn Ser Leu Xaa Cys Trp Val Lys Ser Ser Phe Ser Asn
          60                          65                        70                        75

His Cys Ile Thr Xaa Glu Leu Leu Asp Gly Gln Ala Val Val Ser Ser Phe Val Asn
             80                          85                        90                        95

Tyr Gln Glu Glu Ile Trp Xaa Val Glu Cys Lys Tyr Thr Trp Arg Phe Asp Xaa Cys
                    100                        105                        110

Glu Ile Leu Cys Leu Phe Val Lys Leu Phe Gln Ser Tyr Leu Glu Glu Arg Thr Ser
115                   120                        125                        130

TABLE 8-continued

DNA and amino acid sequences of clone S7

| | | | | | | | | | | | | | | | | | |
|---|---|---|---|---|---|---|---|---|---|---|---|---|---|---|---|---|---|
| Leu | Gln 135 | Asn | Glu | Ile | Ser | Gly 140 | His | Gln | Met | Ser | Val 145 | Tyr | Glu | Glu | Gln | Val 150 | Leu | His |
| Phe | Gln | Val 155 | Leu | Xaa | Asn | Gly | Val 160 | Xaa | Arg | Gln | Ser | Met 165 | Glu | Asn | Leu | Xaa 170 | Cys | Ser |
| Ser | His | His | Val 175 | Lys | Glu | Leu | Phe | Phe 180 | Thr | Asn | Ser | Glu | Ser 185 | Thr | Xaa | Glu | Asp | Asn 190 |
| Val | Leu | Leu | Thr | Ala 195 | Asn | Asn | Thr | Arg | Phe 200 | Tyr | Asp | Ile | Val | Xaa 205 | Trp | Xaa | Ser | Ser |
| Xaa 210 | Asp | Phe | Phe | Ser | Xaa 215 | Thr | Asn | Asn | Ile | Cys 220 | Lys | Leu | Glu | Ser | Phe 225 | Gly | Ile | Thr |
| Phe | Asn 230 | Ala | Trp | Cys | Val | Pro 235 | Leu | Leu | Ala | Leu | Phe 240 | Ser | His | Xaa | Ser | Ser 245 | Met | Phe |
| Thr | Asn | Gly 250 | Thr | Ile | Lys | Leu | Val 255 | Xaa | Lys | Leu | Ile | Ile 260 | Xaa | Asn | Lys | Leu | His 265 | Val |
| Leu | Asn | Lys | Lys 270 | Leu | Arg | Val | Lys | Lys 275 | Ile | Tyr | Asn | Tyr | Ile 280 | Leu | His | Leu | His | Thr 285 |
| Asp | Asp | Asp | Gly | Cys 290 | Arg | Ser | Gly | Arg | His 295 | Arg | Ser | Ser | Gln | Pro 300 | Ile | Pro | Ala | Phe |
| Leu 305 | Gly | Gln | Leu | Gln | Xaa 310 | His | Leu | Thr | Leu | Asn 315 | Lys | Tyr | Asn | Ile | Lys 320 | Lys | Lys | Arg |
| Ile | Leu 325 | Lys | Gly | Lys | Lys | Thr 330 | Asn | Ala | Thr | Lys | Xaa 335 | Xaa | Phe | Asp | Asn | Ser 340 | Lys | Lys |
| Trp | Pro | Arg 345 | Phe | Phe | Thr | Glu | Lys 350 | Leu 351 | | | | | | | | | | |

SEQUENCE DESCRIPTION: SEQ ID NO. 42:

| | | | | | | | | | | | | | | | | | |
|---|---|---|---|---|---|---|---|---|---|---|---|---|---|---|---|---|---|
| Pro | Phe | Xaa | Gly | Glu 5 | Asn | Asn | Ser | Arg | Ser 10 | Ile | Val | Ser | Ser | Ile 15 | Xaa | Thr | Cys | Phe |
| Leu 20 | Asn | Val | Lys | Phe | Xaa 25 | Tyr | Ile | Xaa | Asn | Thr 30 | Phe | Lys | Ile | Xaa | Asn 35 | Gly | Thr | Phe |
| His | Phe 40 | Ile | Lys | Xaa | Leu | Ile 45 | Arg | Xaa | Xaa | Glu | Met 50 | Lys | Phe | Tyr | Val | Ile 55 | Thr | Xaa |
| Gln | Phe | Ser 60 | Tyr | Met | Leu | Xaa | Phe 65 | Thr | Leu | Val | Leu | Ser 70 | Xaa | Gln | Gln | Leu | Gln 75 | Xaa |
| Pro | Leu | His | Asn 80 | Met | Xaa | Ser | Pro | Arg 85 | Arg | Ser | Arg | Ser | Cys 90 | Leu | Phe | Ile | Arg | Gln 95 |
| Ile | Thr | Arg | Arg | Asp 100 | Met | Leu | Ser | Xaa | Met 105 | Gln | Ile | Asp | Met | Gln 110 | Phe | Arg | Leu | Met |
| Xaa 115 | Asp | Leu | Val | Phe | Leu 120 | Ser | Gln | Ser | Ile | Pro 120 | Leu | Val | Ala | Gly | Arg 130 | Thr | His | Glu |
| Thr | Ser 135 | Glu | Xaa | Tyr | Glu | Trp 140 | Ala | Ala | His | Leu | Arg 145 | Val | Gly | Arg | Ser | Cys 150 | Pro | Pro |
| Ile | Pro | Gly 155 | Thr | Leu | Lys | Gly | Ser 160 | Ile | Glu | Ser | Glu | Asp 165 | Xaa | Glu | Ile | Leu 170 | Leu | Phe |
| Xaa | Pro | Thr | Ser 175 | Glu | Arg | Pro | Leu | Leu 180 | Tyr | Gln | Glu | Xaa | Leu 185 | Asn | Ile | Xaa | Xaa | Gln 190 |
| Cys | Pro | Pro | Asp 195 | Arg | Gln | Glu | Asn | Gln 200 | Leu | Leu | Arg | His | Ser 205 | Val | Met | Leu | Phe | Ile |
| Leu 210 | Arg | Leu | Phe | Glu | Val 215 | His | Xaa | Gln | His | Val 220 | Glu | Ile | Xaa | Gln | Phe 225 | Arg | His | His |
| Leu | Lys 230 | Gly | Leu | Leu | Ser | Ser 235 | Ser | Pro | Gly | Phe | Leu 240 | Phe | Thr | Leu | Xaa | Glu 245 | His | Leu |
| His | Lys | Trp 250 | Asn | Asp | Xaa | Pro | Ser 255 | Met | Lys | Ser | His | Asn 260 | Leu | Lys | Glu | Phe | Ser 265 | Gly |

TABLE 8-continued

DNA and amino acid sequences of clone S7

| | | | | | | | | | | | | | | | | | |
|---|---|---|---|---|---|---|---|---|---|---|---|---|---|---|---|---|---|
| Phe | Lys | Lys | Lys 270 | Ile | Gln | Ser | Lys | Lys 275 | His | Leu | Xaa | Leu | Asp 280 | Ser | Ala | Phe | Ser | Tyr 285 |
| Arg | Arg | Arg | Trp | Met 290 | Xaa | Ile | Arg | Gln | Pro 295 | Ser | Xaa | Ile | Thr | Ser 300 | Tyr | Thr | Cys | Ile |
| Phe 305 | Gly | Pro | Thr | Thr | Leu 310 | Thr | Thr | Asn | Phe | Lys 315 | Gln | Leu | Lys | Asp | Lys 320 | Lys | Lys | Lys |
| Asn | Val 325 | Xaa | Arg | Glu | Gln | His 330 | Xaa | Cys | Asp | Glu | Ile 335 | Leu | Phe | Xaa | Xaa | Glu 340 | Glu | Glu |
| Leu | Ala | Pro 345 | Leu | Leu | Asp | Gly | Gln 350 | | | | | | | | | | | |

SEQUENCE DESCRIPTION: SEQ ID NO. 43:

| | | | | | | | | | | | | | | | | | |
|---|---|---|---|---|---|---|---|---|---|---|---|---|---|---|---|---|---|
| Pro | Ile | Val | Gly | Xaa 5 | Xaa | Gln | Lys | Ser | Ile 10 | Tyr | Ser | Leu | Ile | Asn 15 | Leu | Tyr | Leu | Ile |
| Phe 20 | Gln | Gly | Gln | Ile | Leu 25 | Leu | Asn | Leu | Lys | His 30 | Ile | Xaa | Asn | Leu | Lys 35 | Trp | Tyr | Leu |
| Ser | Ile 40 | Asn | Lys | Val | Phe | Asn 45 | Ala | Ile | Ile | Gly | Asn 50 | Xaa | Leu | Ile | Cys 55 | Tyr | Asp | Ile |
| Ser | Ile | Leu 60 | Val | Asn | Thr | Leu | Phe 65 | Asn | Ala | Gly | Phe | Lys 70 | Val | Ala | Ser | Ala 75 | Thr | Ile |
| Ala | Ser | Pro | Glu 80 | Asn | Leu | Phe | Thr | Glu 85 | Lys | Leu | Ser | Xaa | Leu 90 | Pro | Phe | Tyr | Thr 95 | Thr |
| Asn | Asn | Lys | Xaa | Gly 100 | Asn | Phe | Lys | Val | Asn 105 | Thr | His | Gly | Asp | Ser 110 | Ile | Lys | Ala | Asn |
| Leu 115 | Xaa | Ala | Cys | Phe | Ser 120 | Lys | Ser | Phe | Asn | Pro 125 | Thr | Cys | Ser | Arg | Glu 130 | His | Ala | Xaa |
| Asn | Ile 135 | Arg | Leu | Val | Gly | Met 140 | Ser | Cys | Pro | Ser | Thr 145 | Ser | Arg | Lys | Phe | Leu 150 | Thr | Ser |
| Asn | Ser | Trp 155 | Asp | Ile | Glu | Trp | Lys 160 | Asp | Arg | Val | Xaa | Arg 165 | Met | Xaa | Asn | Ala | Leu 170 | Val |
| Ile | Thr | Tyr | Lys 175 | Arg | Ser | Ser | Ser | Pro 180 | Ile | Ala | Arg | Leu | Pro 185 | Lys | Asn | Met | Met | Ser 190 |
| Leu | Ser | Pro | Arg | Thr 195 | Thr | Arg | Glu | Ser | Thr 200 | Ile | Xaa | Ser | Lys | Gly 205 | Asn | Pro | Leu | Asp |
| Thr 210 | Ser | Ser | Val | Arg | Arg 215 | Thr | Ile | Ser | Ala | Ser 220 | Xaa | Asn | Val | Ser | Val 225 | Xaa | Pro | Ser |
| Thr | Gln 230 | Gly | Ala | Phe | Gln | Phe 235 | Phe | Pro | Trp | Phe | Pro 240 | Ile | Asp | Ala | Val | Xaa 245 | Ser | Pro |
| Thr | Glu | Leu 250 | Xaa | Arg | Leu | Ser | Glu 255 | Asn | Xaa | Phe | Ser | Lys 260 | Ile | Lys | Xaa | Ile | Phe 265 | Trp |
| Ile | Lys | Lys | Xaa 270 | Asp | Ser | Lys | Lys | Xaa 275 | Thr | Thr | Ile | Phe | Xaa 280 | Ile | Cys | Ile | Leu | Ile 285 |
| Thr | Thr | Glu | Val | Asp 290 | Leu | Asp | Glu | Thr | Ala 295 | Val | Leu | Asn | His | Phe 300 | Leu | His | Leu | Tyr |
| Val 305 | Arg | Ser | Asn | Asn | Ile 310 | Tyr | His | Xaa | Ile 315 | Lys | Thr | Ile | Xaa | Arg 320 | Lys | Lys | Glu | Xaa |
| Xaa 325 | Ser | Val | Lys | Arg | Pro 330 | Thr | Leu | Leu | Arg | Arg 335 | Asn | Ser | Ile | Met | Val 340 | Arg | Arg | Gly |
| Leu | Gly | Ser 345 | Ser | Pro | Arg | Arg | Ser 350 | | | | | | | | | | | |

The longest open reading frame comprises 201 amino acids of the 1053 nucleotides of the insert. It starts at nucleotide 169 (TCT ATT . . . ) in a phase 1 translation (starting at the first nucleotide and preceding left to right).

Extensive homology was observed between this sequence and the 20 kD protein of *Clostridium pasteruanium*, the 29 kD surface protein of *Entamoeba histolytica*, a *Helicobacter pylori* protein, and the 22 kD subunit of the alkyl hydroperoxide reductase of *Salmonella typhimurium*, having GenBank accession numbers M75858 (E. hist.), M55507 (H. pylori) and MO5478 (S. typh.), respectively.

This sequence was obtained by the successive generation of sequencing primers as described for clone S34. Table 9 below provides the enzyme restriction map for this clone derived from the sequence.

TABLE 9

Enzyme Restriction Map of DNA from Clone S7

```
                                          529 Xho I                                              1033 Bsi I
                                          462 AvaII                                              1033 Bsi YI
                223 Bsp WI                423 Fnu4H I                        757 Afl II          919 Gsu I
        158 Xca I                         423 Bst71 I           645 Afl III                      919 Bpm I
        158 Bst1107 I                     395 HgiA I            644 BsaA I                       918 BstN I
        158 Acc I                         349 Tth111 II  529 PaeR7 I   694 BstX I        871 Xba I       1027 Sty I
1 Nci I  152 Dra I                        340 Bsm I      529 Ava I     682 Hph I         861 Esp3 I      998 Bbv II
1 Bcn I  120 Ssp I    267 Sfc I           395 Bsp1286 I      583 BstU I    735 BspH I    874 BstY I      1019 Ear I
```

S7FINAL        1055 base pairs        Unique Sites

Antibodies elicited by *C. parvum* immunization that bind to the 23 kD apparent molecular weight peptide also bind to the S7 polypeptide.

The subgroup of antibodies binding to the 23 kD group of polypeptides show substantially no binding to other groups.

Example 21
DNA Sequence of Clone S24.

The DNA nucleotide sequence of the *C. parvum* insert of clone S24 was determined as described for the S34 clone. A partial DNA sequence obtained and its complementary strand are shown in Table 10 below as are the six possible acid sequences deduced therefrom.

TABLE 10

DNA and amino acid sequences of clone S24

SEQUENCE DESCRIPTION: SEQ ID NO. 21:

Thr Leu Asn Gln Xaa Ile Gln Phe Val Asn Leu Ile Xaa Phe Pro Val
                    5                   10              15

Lys Xaa Asn Ile Phe Tyr Lys Ile Gln Tyr Tyr Ser Ile Leu Lys Tyr
            20                  25                  30

Thr Ile Val Tyr Xaa Asn Glu Tyr Ile Ser Xaa Lys Val Ser Thr Lys
        35                  40                  45

Leu Tyr Cys Xaa Ala Val Met Gln Met Val His Ser Glu Val
    50                  55                  60

SEQUENCE DESCRIPTION: SEQ ID NO. 22:

Asp Leu Glu Ser Ile Asn Ser Ile Cys Glu Phe Asn Leu Ile Ser Ser
                5                   10                  15

Lys Val Lys Tyr Phe Leu Gln Asn Ser Val Leu Phe His Phe Lys Val
            20                  25                  30

Tyr Asn Ser Leu Leu Lys Xaa Val His Xaa Leu Glu Ser Xaa His Gln
        35                  40                  45

Thr Leu Leu Leu Ser Cys Tyr Ala Asp Gly Ser Phe Arg Gly
    50                  55                  60

SEQUENCE DESCRIPTION: SEQ ID NO. 23:

Gly Pro Xaa Ile Asn Lys Phe Asn Leu Xaa Ile Xaa Phe Asn Phe Gln
                5                   10                  15

Xaa Ser Glu Ile Phe Phe Thr Lys Phe Ser Ile Ile Pro Phe Xaa Ser
            20                  25                  30

Ile Gln Xaa Ser Ile Glu Met Ser Thr Leu Val Arg Lys Leu Ala Pro
        35                  40                  45

TABLE 10-continued

DNA and amino acid sequences of clone S24

Asn Phe Thr Ala Glu Leu Leu Cys Arg Trp Phe Ile Gln Arg Ser
    50              55                  60

SEQUENCE DESCRIPTION: SEQ ID NO. 33:

| | | | | |
|---|---|---|---|---|
| GGACCTTGAA | TCAATAAATT | CAATTTGTGA | ATTTAATTTA | ATTTCCAGTA | AAGTGAAATA | 60 |
| TTTTTTACAA | AATTCAGTAT | TATTCCATTT | TAAAGTATAC | AATAGTCTAT | TGAAATGAGT | 120 |
| ACATTAGTTA | GAAAGTTAGC | ACCAAACTTT | ACTGCTGAGC | TGTTATGCAG | ATGGTTCATT | 180 |
| CAGAGGTCT  |            |            |            |            |            | 189 |

SEQUENCE DESCRIPTION: SEQ ID NO. 50:

CCT GGA ACT TAG TTA TTT AAG TTA AAC ACT TAA ATT AAA TTA AAG GTC ATT TCA CTT  57

TAT AAA AAA TGT TTT AAG TCA TAA TAA GGT AAA ATT TCA TAT GTT ATC AGA TAA CTT  114

TAC TCA TGT AAT CAA TCT TTC AAT CGT GGT TTG AAA TGA CGA CTC GAC AAT ACG TCT  171

ACC AAG TAA GTC TCC AGA  189

SEQUENCE DESCRIPTION: SEQ ID NO. 44:

Ser Arg Ser Asp Ile Phe Glu Ile Gln Ser Asn Leu Lys Ile Glu Leu Leu Thr Phe
            5               10              15

Tyr Lys Lys Cys Phe Glu Thr Asn Asn Trp Lys Leu Thr Tyr Leu Leu Arg Asn Phe
20              25              30              35

His Thr Cys Xaa Asn Ser Leu Xaa Cys Trp Val Lys Ser Ser Leu Gln Xaa Ala Ser
    40                                      50              55

Pro Glu Asn Leu Pro Arg
        60      63

SEQUENCE DESCRIPTION: SEQ ID NO. 45:

Val Lys Phe Xaa Tyr Ile Xaa Asn Thr Phe Lys Ile Xaa Asn Gly Thr Phe His Phe
            5               10              15

Ile Lys Lys Cys Phe Glu Thr Asn Asn Trp Lys Leu Thr Tyr Leu Leu Arg Asn Phe
20              25              30              35

His Thr Met Leu Xaa Phe Thr Leu Val Leu Ser Xaa Gln Gln Ala Thr Ile Cys Ile
    40              45              50              55

Thr Xaa Glu Ser Thr
    60      62

SEQUENCE DESCRIPTION: SEQ ID NO. 46:

Gly Gln Ile Leu Leu Asn Leu Lys His Ile Xaa Asn Leu Lys Trp Tyr Leu Ser Ile
            5               10              15

Asn Lys Val Phe Asn Leu Ile Ile Gly Asn Xaa Leu Ile Cys Tyr Asp Ile Ser Ile
20              25              30              35

Leu Val Asn Thr Leu Phe Asn Ala Gly Phe Lys Val Ala Ser Ser Asn His Leu His
    40              45              50              55

Asn Met Xaa Leu Asp
    60      62

There is no obvious candidate for the correct reading frame in the 189 nucleotides of the insert. This sequence was obtained by using the universal primers obtained from US Biochemical. Table 11 below provides the enzyme restriction map of this clone as generated from then sequence.

TABLE 11

| Enzyme Restriction Map of DNA for Clone S24 | | | | |
|---|---|---|---|---|
| 8 Tfi I | | 95 Xca I | | 158 Alu I |
| 8 Hinf I | | 95 Bst1107 I | | 155 Dde I |
| 1 Sau96 I | 57 Ssp I | 95 Acc I | | 154 Esp I |
| 1 Ava II | 45 Bsr I | 89 Dra I | 119 Rsa I | 154 Bpu1102 I |

S24-3AND5/4.5H    189 base pairs    Unique Sites

Antibodies raised against *C. parvum* that bind to the 15 and 35 kD apparent molecular weight peptides also bind to the S24 polypeptide. This subgroup of antibodies shows substantially no binding activity with respect to the polypeptides of the other antigenic groups.

Example 22

Agents Suitable for Passive Immunotherapy

The polypeptides of the invention bind to antibodies also specifically binding to epitopes of *C. parvum*. These *C. parvum* epitopes are also recognized by B and T cells. The polypeptides mentioned above are produced in large amounts by reinserting the *C. parvum* DNA from the different clones obtained in the Examples above into an expression vector such as pGEX, pET-9d, or baculovirus. The thus constructed hybrid vector is used to transfect a host. The host cells carrying the hybrid vector are then grown in a nutrient medium to allow the production of the gene product.

pGEX (Pharmacia)(Smith, Gene 67:31 (1988)) or pET-9d (Novagen)/pRSET T7 (Invitrogen) utilize the T7 RNA polymerase and the T7 promoter (Studier, F. W., Meth. Enzymol. 185:60 (1990)) and hosts derived from *E. coli*. The vector sequences may be easily eliminated following protein expression so that the subsequent immunogenic protein contains only Cryptosporidium sequences. These expression systems are commercially available and their use is standard in the art.

Recombinant baculovirus is a simple vehicle for the expression of large quantities of protein from eukaryotic or prokaryotic gene origin. The genes are expressed under the control of the *Autographa californica* multiple nuclear polyhedrosis virus (AcMNPV) polyhedral promoter contained in transfer vectors used to infect *Spodoptera frugiperda* (Sf9 or Sf21) insect cells. A number of transfer vectors are available for the production of protein from both full length and partial cDNA and genomic clones. Fused or non-fused protein products, depending on the vector used, constitute up to 50% of the total protein produced in infected cells. The thus obtained recombinant proteins are frequently immunologically and functionally similar to the corresponding endogenous proteins. Proteins with signal peptides may be secreted into the media while those without secretion signals will aggregate in the cells or be localized at the membrane. Baculovirus expression systems are commercially available (Invitrogen), (Smith, D., and Johnson, K., (1988), supra; Studier, F. W., et al. (1990), supra).

The thus obtained polypeptide is purified by methods known in the art, and the degree of purification varies with the use of the polypeptide. For use in eliciting polyclonal antibodies, the degree of purity may not need to be high. However, in some cases impurities may cause adverse reactions and the degree of purity must be higher.

When used to passively immunize Cryptosporidium infected animals, the polypeptide is first combined with appropriate adjuvants and used for the immunization of cows or other donor animals to produce antibodies which may be administered to patients with cryptosporidiosis infection, particularly to AIDS patients and other immunocompromised hosts, including animals.

Example 23

Agents Suitable for Active Immunotherapy

Polypeptides comprising epitopes of *C. parvum* recognized by B and/or T cells are produced in large amounts by recloning as described in Example 22 above.

The polypeptide thus obtained is purified as described above (e.g. Smith, D., and Johnson, K., (1988), supra).

The degree of purification varies with the use of the polypeptides. For use in eliciting polyclonal antibodies, the degree of purity may be lower than for other applications. For the preparation of a pharmaceutical composition, however, the degree of purity must be high, as is known in the art.

When in a therapeutic composition, the polypeptide is combined with appropriate adjuvants and used for the immunization of immunocompetent patients who are at risk for cryptosporidiosis either at the time of immunization of in the future. This group includes, but is not restricted to, HIV positive individuals who are still able to respond to vaccination, animal workers, health care workers, day care center children and their caretakers, and children in the developing world.

Example 24

Agents Suitable for Immunodiagnostic Use

Polypeptides comprising epitopes of *C. parvum* that are recognized by intact B and/or T cells are produced in large amounts as described above, purified and used to detect or characterize anti-*C. parvum* antibody in the body substances of populations at risk of prior or current cryptosporidial infection. In addition, antibodies to such polypeptides are obtained by immunizing animals, such as rabbits or goats, with the polypeptide plus adjuvant as described. Typical intramuscular immunization schedules are as follows.

1) Polypeptide plus equal volume complete Freunds adjuvant at the beginning.
2) Polypeptide plus equal volume incomplete Freunds adjuvant at week 2.
3) Polypeptide plus equal volume incomplete Freunds adjuvant at week 4.

These antibodies are used to detect Cryptosporidium antigens in body substances, for example, stools of populations at risk of cryptosporidial infection by, e.g., collecting stool samples (Manual of Clinical Microbiology (1986), supra), mixing with Streather's solution 1:4, and incubating with antibody followed by addition of a fluorescein conjugated second antibody as described. However, colorimetric labels which do not require special microscope equipment are suitable.

Example 25

Anti-*C. parvum* Antibodies Eluted from Western Blot

For SDS-PAGE, $2 \times 10^9$ oocysts were lysed by 5 cycles of freeze-thawing in 1% Triton Buffer (150 mM Na CI; 100 mM EDTA; and 1% Triton X-100), in the presence of protease inhibitors (100 µM E64, chymotrypsin, pepstatin, and leupeptin; and 1.6 mM PMSF), and boiled in Sample Buffer (SB). Proteins were electrophoresed in 5–15% gradient gels (Laemmli, U. K., "Cleavage of Structural Proteins During the Assembly of the Head of Bacteriophage T4", Nature 227:680 (1971)) and blotted onto nitrocellulose at 0.7 amp. for 8 hrs. (Petersen, C., et al., "Characterization of an Mr>900,000 *Cryptosporidium parvum* Sporozoites Glycoprotein Recognized by Hyperimmune Bovine Colostral Immunoglobulin", Inf. & Immun. 60(12):5132 (1992)). Western blots were incubated with HBC Ig (lot #40529) (dil 1/500) in 20 ml PBS for 3 hrs. at 4° C., rinsed 3 times with phosphate buffered saline (PBS), and antibodies eluted with 10 ml of glycine buffer (pH 2.6) for 3 min., followed by addition of a 1/10 volume of 2M Tris buffer, pH 8 (Tilley, M., et al., "*Cryptosporidium parvum* (Apicomplexa: Cryptosporidiidae) Oocyst and Sporozoite Antigens Recognized by Bovine Colostral Antibodies", Inf. Imm. 58:2966 (1990)). Eluted antibodies were filter sterilized and concentrated to a final volume of 1 ml in a Centriprep 10 concentrator (Amicon, Mass.).

Example 26

In vitro Inhibition Assay

The in vitro cell culture system of Gut et al. was modified as follows to quantify the effect of antibody on the infection of epithelial cells by *C. parvum* (Gut J., et al., "*Cryptosporidium parvum*: In vitro Cultivation in Madin-Darby Canine Kidney Cells" J. Protozool. 386:72 (1991)). MDCK cells were maintained in RPMI-1640 with the addition of 5% heat inactivated fetal calf serum (FCS). Two ml aliquots containing $2 \times 10^5$ MDCK cells/ml were seeded in 8 well tissue culture plates and allowed to attach to 20 mm square cover glasses for 24 h at 37° C. in a 5% $CO_2$: 95% air atmosphere.

The cells were then rinsed in RPMI without FCS for 30 minutes, exposed to $2 \times 10^6$ purified oocysts resuspended in RPMI medium containing HBC Ig (lot#40529) (1000; 500; 200; 100; and 50 µg/ml IgG), SHAM-HBC Ig (lot #41038) (1500; 250; 150; and 75 µg/ml IgG), eluted antibodies (50–100 µg/ml IgG), or 5% FCS (300–500 µg/ml IgG). In some experiments, controls were also conducted consisting of MDCK cells infected with *C. parvum* oocysts resuspended in RPMI medium with the addition of glycine buffer at the same concentration utilized for the cultures treated with eluted antibody as described above.

The cultures were incubated for 2 hrs. at 37° C., rinsed 4 times with RPMI to remove extracellular sporozoites and unexcysted oocysts, and reincubated for an additional 21 hrs. period in the presence of the respective antibody reagents described above. Monolayers were subsequently fixed in 3.7% formaldehyde in PBS, rinsed, and stained in PBS with the addition of 1 µM Hoescht 33258 dye (Sigma) for 1 hr. at 37° C. (Melamed, M. R., and L. A. Kamentsky, "Automated Cytology", Exp. Pathol. 14:205 (1975)).

The number of intracellular parasites/200–400 cells was quantified in 3 independent experiments in coded slides (n=3–4) by fluorescence microscopy. Differences in the mean number of intracellular parasites/cell were statistically analyzed.

The data were expressed as the E/C ratio (±SEM), where E was the mean number of intracellular parasites in the treated culture, and C the mean number of intracellular parasites in the untreated or SHAM-HBC Ig treated controls (Crane, M. S. J., and J. C. McGaley, "*Eimeria tenella*: Inhibition of Host Cell Invasion by Phospholipase Treatment of Sporozoites", Exp. Parasitol. 72:219 (1991); Doyle, P. S., et al., "*Trypanosoma cruzi*: Quantification and Analysis of the Infectivity of Cloned Stocks", J. Protozool. 31:2806 (1984)).

Example 27

Western Blots

To identify the molecular targets of protective antibody, total *C. parvum* sporozoite and sporozoite/oocyst proteins were boiled in sample buffer (SB), resolved in 5–15% gradient gels by SDS-PAGE and Western blotted with HBC Ig. In addition, sporozoite/oocyst proteins solubilized in Triton-X 100 were immunoprecipitated with HBC Ig at dilutions 1/1,000; 1/5,000; 1/10,000; 1/50,000 and 1/100,000. Controls were *C. parvum* proteins immunoprecipitated under the same conditions but with SHAM-HBC Ig at dilutions 1/1,000 to 1/10,000. Immunoprecipitates were also resolved by SDS-PAGE and Western blotted. Western blots of HBC Ig immunoprecipitates were developed with HBC Ig (dil 1/1,000) and SHAM immunoprecipitates were developed with SHAM-HBC Ig (dil 1/1,000). After incubation with 10 µCi[$^{125}$I]-Protein G for 1 hr. at room temperature, blots were dried and exposed for autoradiography.

Example 28

Discussion of HBC Ig Inhibition Results

The in vitro assay described in Example 26 above was used to determine inhibition of Cryptosporidium invasion and/or intracellular development as a function of HBC Ig titer. HBC Ig, at concentrations ranging from 100–1,000 µg/ml IgG, resulted in a significant reduction in the mean number of intracellular parasites/host cell of up to 61% relative to FCS controls as can be seen in FIG. 1 (p<0.01), while no inhibition was observed at lower HBC Ig (≦50 µg/ml of IgG) concentrations. A second control, SHAM-HBC Ig, was found not to significantly inhibit *C. parvum* infectivity relative to 5% FCS controls, although this reagent does contain some anti-Cryptosporidium activity by ELISA as shown in FIG. 2. In addition, HBC Ig (100–1,000 µg/ml IgG) significantly inhibited Cryptosporidium invasion and/or development when compared to SHAM-HBC Ig controls by 45–55%. Specific anti-*C. parvum* antibodies were affinity purified from Western blot (about 50–100 µg IgG/ml). This eluted antibody also inhibited Cryptosporidium invasion/development relative to SHAM-HBC Ig controls, and controls with the addition of glycine buffer or FCS as shown in FIG. 3 (p<0.01).

Example 29

Discussion of Immunoprecipitation and Western Blots using Antibodies

When total oocyst/sporozoite proteins were immunoprecipitated with HBC Ig at different concentrations and blotted, two sporozoite molecules of >900 kD and about 250 kD were the major antigenic targets identified by protective colostrum (FIG. 4, lanes 1–4) but not by SHAM-HBC Ig (lanes 5–7) at all the Ab concentrations assayed. Most of the C. parvum antigenic proteins recognized by HBC Ig are expressed by sporozoites as evidenced by the comparison of total sporozoite and oocyst/sporozoite proteins recognized by HBC Ig in Western blots (data not shown). Cryptosporidium sporozoites were also radioiodinated to identify antigens localized to their surface. Twenty-two surface iodinatable sporozoite proteins were resolved by SDS-PAGE (FIG. 5, lane 1). Protective anti-Cryptosporidium antibodies (lot#140529) immunoprecipitated most of these surface labeled sporozoite proteins. The number of radiolabeled immunoprecipitated proteins resolved by gel electrophoresis differed for membranes solubilized with SDS or with Triton X-100. Nineteen labeled sporozoite surface proteins extracted with SDS were specifically immunoprecipitated by HBC Ig (FIG. 5, lane 2) including a >900 kD and about 250 kD molecules (FIG. 5B). Only thirteen radioiodinated 1% Triton X-100 soluble proteins were immunoprecipitated by protective HBC immunoglobulins (FIG. 5, lane 3) including the >900 kD species (FIG. 5B). No radioiodinated molecules were observed in TCA precipitated controls of the soluble cytoplasmic fraction (data not shown) indicating that only membrane proteins were iodinated by this methodology.

Example 30

Production of Antibody to Fusion Protein

A recombinant λgt 11 bacteriophage carrying DNA sequences encoding C. parvum polypeptides, such as the S2, S19 and S34 proteins, was used to infect E. coli Y1089 as described in Promega Protocols and Applications, $2^{nd}$ ed., p. 228 (Promega Corp, Madison, Wis.). Lysogens grown on LB agar containing ampicillin and tetracycline at 32° C. were selected when clones exhibited confluent growth at 32° C. but spotty growth at the lytic temperature of 42° C. Single colonies of the lysogens were chosen and grown in LB broth until the $A_{600}$=0.5. The temperature was then raised to 42° C. for 20 min., IPTG was added to 6 mM to induce fusion protein synthesis, and the cultures were grown for an additional 2.5 hrs. at 42° C. The bacteria were harvested by centrifugation, freeze-thawed 3 times, lysozyme treated and vortexed to reduce the viscosity due to released nucleic acids.

The fusion proteins were purified from the bacterial lysates by affinity chromatography on anti-β galactosidase-agarose (Protosorb LacZ, Promega Corp.) according to manufacturers instructions with elution of the fusion proteins using 100 mM sodium carbonate, pH 10.8. S2, S19 and S34 derived fusion proteins were successfully purified using this methodology.

Two CD-1 adult mice were separately immunized intraperitoneally with about 1 µg fusion protein from each clone at 2 to 4 week intervals using the Ribi Adjuvant System (Ribi Immunochem Research, Hamilton, Mont.) Freund's Complete Adjuvant. The mice receiving the S34 antigen were boosted with 5 to 10 µg fusion protein excised from SDS polyacrylamide gel, minced and extruded through a hypodermic needle, which was administered i.p. After 7 total immunizations, the production of ascites was induced by the i.p. inoculation of animals with Freund's Complete Adjuvant. The resulting ascites were used to probe western blotted Cryptosporidium parvum oocyst lysates. As expected, the anti-S2 ascites recognized about 45 kD band, the anti-S19 ascites recognized the about 68 kD band, and the anti-S34 ascites recognized a band migrating at the stacking gel interface (>250 kD).

Example 31

In Vitro Inhibition of C. parvum Infectivity by anti-S19, S34, and S2 Cryptosporidium Protein Antibodies An in vitro cell culture system was utilized to quantify the effect of antibody on the infection of epithelial cells by C. parvum (Doyle, P., et al., "Anti-Cryptosporidium parvum Antibodies Inhibit Infectivity In Vitro and In Vivo", Inf. Immun. (1993), in press). Briefly, MDCK cells were maintained in RPMI-1640 medium with the addition of 5% heat inactivated fetal calf serum (FCS). Two ml aliquots containing $2 \times 10^5$ MDCK cells/ml were seeded in 8 well tissue culture plates and allowed to attach to 20 mm square cover glasses for 24 hrs. at 37° C. in a 5% $CO_2$: 95% air atmosphere.

The cells were then rinsed in RPMI medium without FCS for 30 min., exposed to $2 \times 10^6$ purified oocysts resuspended in RPMI medium containing the antibodies, i.e., anti-S19 ascites; anti-S34 ascites; anti-S2 ascites; hyperimmune bovine colostrum immunoglobulin (HBC Ig); anti-GP900 mouse ascites raised against the denatured purified glycoprotein (anti-GP900 ascites); a SHAM hyperimmune bovine colostrum (SHAM-HBC Ig) control; and a 5% heat inactivated fetal bovine serum (FCS) control.

The cultures were incubated for 2 hrs. at 37° C., rinsed 4 times with RPMI to remove extracellular sporozoites and unexcysted oocysts, and reincubated for an additional 21 hrs. period in the presence of the respective antibody reagents as described above. Monolayers were subsequently fixed in 3.7% formaldehyde in PBS, rinsed, and stained in PBS with the addition of 1 µM Hoescht 33258 dye (Sigma) for 1 hr. at 37° C. The number of intracellular parasites/200–400 cells was quantified in coded slides (n=2) by fluorescence microscopy. Differences in the mean number of intracellular parasites/cell were statistically analyzed. The results were expressed as the mean number of intracellular parasites per cell (±SD) in the treated cultures and SHAM-HBC Ig and FCS controls and are shown in FIG. 6.

The highest degree of inhibition of C. parvum infectivity was shown by the anti-S19 protein antibodies. The anti-S34 and anti-S2 protein antibodies inhibited about ⅔ of the infectivity displayed by the control. The HBC Ig and anti-GP900 protein antibodies showed some inhibitory effect but less so than the previous samples.

Example 32

Inhibition of C. parvum Sporozoite Infectivity

The following results confirm the findings of Example 31 above.

The ascites were tested for their ability to neutralize Cryptosporidium sporozoite infectivity using a modification of the Cryptosporidium invasion assay described by Tilley et al (Tilley et al., Infec. Immun. 59:1002–1007 1991). Briefly, MDBK cells were seeded into 8 well plastic chamber slides (Labtek, Nunc, Napersville, Ill.) at a concentration of $4 \times 10^4$ cells/well in Dylbecca's Modified Eagle medium (DME)/2% Fetal Bovine Serum (FBS) and grown for 3 days to greater than 90% confluency. Purified C. parvum oocysts from a virulent calf isolate, recently passaged in a newborn calf, were excysted by exposure to 0.75% (w/v) sodium taurocholate for 1 hour at 37° C. Sporozoites were purified by passage through a 2 μm polycarbonate filter (Nuclepore, Costar Inc.) in a 25 mm Swinnex filter housing (Millipore Corp., Bedford Mass.). 1.25×10⁶ sporozoites in DME/2% FBS were added to the reaction mixtures containing test or control antibodies at a final dilution of 1:10 in 0.5 ml DME/2% FBS. After 1 hr. of incubation at room temperature, 0.4 ml of each mixture were separately applied to cell monolayers and incubated for 24 hrs. at 37° C. in 5% $CO_2$.

The monolayers were washed with PBS and processed for immunofluorescence as follows. The cells were fixed with 10% formalin for 15 min. at room temperature and permeabilized with methanol for 10 min. After washing the monolayer with PBS, Bovine anti-Cryptosporidium IgG was added at a dilution of about 1 mg/ml IgG in PBS/1% Normal Goat Serum (NGS) for I hr. at room temperature. The cells were then washed 3 times for 5 min. each time with PBS and FITC goat-anti-bovine IgG (Kirkegaard and Perry Labs, Gaithersburg, Md.) was applied at 1:100 in PBS/1% NGS. After 1 hr. at room temperature, the cells were washed with PBS and mounted in 4% n-propyl gallate/80% glycerol for microscopy. Developing cryptosporidial forms were enumerated in 10 fields at 1000× nominal magnification. The results obtained for three different clones are shown in the following Table 12.

TABLE 12

| Inhibition of *C. parvum* Sporozoite Infectivity | | |
|---|---|---|
| Sample | Dilution | % Inhibition of *C. parvum* Sporozoite Infectivity |
| Control mouse sera | 1:10 | 38.75 ± 18 |
| Anti-S2 ascites | 1:10 | 43.75 ± 47 |
| Anti-S19 ascites | 1:10 | 100.00 ± 0 |
| Anti-S34 ascites | 1:10 | 80.00 ± 31 |

These results clearly indicate an inhibitory effect by anti-S19 and anti-S34 antibodies with respect to the control.

The invention now being fully described, it will be apparent to one of ordinary skill in the art that many changes and modifications can be made thereto without departing from the spirit or scope of the invention as set forth herein.

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
( A ) LENGTH: 176 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: Cryptosporidium parvum ( x i ) SEQUENCE DESCRIPTION: SEQ ID NO: 1:

```
Gln His Phe Leu Leu Gln Leu Glu Pro Gln Asp Asn Gln Gln Leu Leu
1               5                   10                  15

Gln Leu Glu Val Gln Ala Asn Gln Leu Leu Leu Pro Leu Ser Lys Ala
            20                  25                  30

Thr Thr Thr Thr Thr Thr Leu Asn Pro Ile Ile Thr Thr Thr Thr Gln
        35                  40                  45

Lys Pro Thr Thr Thr Thr Thr Thr Lys Val Pro Gly Lys Pro Pro Ile
    50                  55                  60

Ala Thr Thr Thr Thr Thr Leu Lys Pro Ile Val Thr Thr Thr Thr Thr
65                  70                  75                  80

Lys Ala Thr Thr Thr Thr Thr Thr Thr Val Pro Thr Thr Thr Thr Thr
                85                  90                  95

Thr Lys Arg Asp Glu Met Thr Thr Thr Thr Thr Pro Leu Pro Asp Ile
            100                 105                 110

Gly Asp Ile Glu Ile Thr Pro Ile Pro Ile Glu Lys Met Leu Asp Lys
        115                 120                 125

Tyr Thr Arg Met Ile Tyr Asp Tyr Asn Ser Gly Leu Leu Leu Asp Ser
    130                 135                 140

Asn Asp Glu Pro Ile Pro Gly Ser Gln Ala Gly Gln Ile Ala Asp Thr
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Ser | Asn | Leu | Phe | Pro | Gly | Ser | Asn | Ser | Gln | Glu | Tyr | Trp | Phe | Thr | Asn |
|     |     |     |     | 165 |     |     |     |     | 170 |     |     |     |     | 175 |     |

( 2 ) INFORMATION FOR SEQ ID NO:2:

( i ) SEQUENCE CHARACTERISTICS:
        ( A ) LENGTH: 201 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( x i ) SEQUENCE DESCRIPTION: SEQ ID NO: 2:

| Ser | Ile | Glu | Met | Ser | Thr | Leu | Val | Arg | Lys | Leu | Ala | Pro | Asn | Phe | Thr |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ala | Glu | Ala | Val | Met | Ala | Asp | Gly | Ser | Phe | Lys | Lys | Val | Ser | Leu | Ser |
|     |     |     | 20 |     |     |     |     | 25 |     |     |     |     | 30 |     |     |
| Asp | Tyr | Arg | Gly | Lys | Tyr | Val | Val | Leu | Phe | Phe | Tyr | Pro | Leu | Asn | Phe |
|     |     | 35 |     |     |     |     | 40 |     |     |     |     | 45 |     |     |     |
| Thr | Phe | Val | Cys | Pro | Ser | Glu | Ile | Leu | Ala | Phe | Asn | Gln | Ala | Gln | Lys |
|     | 50 |     |     |     |     | 55 |     |     |     |     | 60 |     |     |     |     |
| Asp | Phe | Glu | Lys | Leu | Gly | Val | Gln | Leu | Leu | Ser | Cys | Ala | Gln | Leu | Ile |
| 65 |     |     |     |     | 70 |     |     |     |     | 75 |     |     |     |     | 80 |
| Leu | Asn | Thr | Pro | Met | Leu | His | Gly | Asp | Val | Leu | Leu | Leu | Asn | Lys | Val |
|     |     |     |     | 85 |     |     |     |     | 90 |     |     |     |     | 95 |     |
| Glu | Leu | Asp | Gln | Ser | Ile | Ser | His | Leu | Ser | Leu | Thr | His | Leu | Ile | Gln |
|     |     |     | 100 |     |     |     |     | 105 |     |     |     |     | 110 |     |     |
| Leu | Ala | Arg | Thr | Met | Val | Tyr | Phe | Leu | Glu | Glu | Glu | Gly | Ile | Ala | Leu |
|     |     | 115 |     |     |     |     | 120 |     |     |     |     | 125 |     |     |     |
| Arg | Gly | Leu | Phe | Ile | Ile | Asp | Lys | Glu | Gly | Arg | Val | Val | Arg | Ser | Glu |
|     | 130 |     |     |     |     | 135 |     |     |     |     | 140 |     |     |     |     |
| Val | Ile | Tyr | Asp | Leu | Pro | Leu | Gly | Arg | Ser | Val | Glu | Glu | Thr | Leu | Arg |
| 145 |     |     |     |     | 150 |     |     |     |     | 155 |     |     |     |     | 160 |
| Val | Ile | Asp | Ala | Leu | Gln | Phe | Thr | Glu | Thr | Tyr | Gly | Glu | Val | Cys | Pro |
|     |     |     |     | 165 |     |     |     |     | 170 |     |     |     |     | 175 |     |
| Ala | Asn | Trp | Lys | Lys | Gly | Gln | Lys | Gly | Met | Ser | Ala | Thr | His | Glu | Gly |
|     |     |     | 180 |     |     |     |     | 185 |     |     |     |     | 190 |     |     |
| Val | Ser | Ser | Tyr | Leu | Lys | Asp | Ser | Phe |
|     |     | 195 |     |     |     |     | 200 |     |

( 2 ) INFORMATION FOR SEQ ID NO:3:

( i ) SEQUENCE CHARACTERISTICS:
        ( A ) LENGTH: 361 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
     &

-continued

```
Glu Phe Pro Asp Arg Ser Leu Asp Phe Thr Ile Pro Pro Val Ala Gly
 1               5                   10                  15
His Asn Ser Cys Ser Ile Ile Val Gly Val Ser Gly Asp Gly Lys Ile
               20                  25                  30
His Val Ser Pro Tyr Gly Ser Lys Asp Val Ser Leu Ile Ser Ala Pro
           35                  40                  45
Ile Gln Pro Ser Glu Leu Phe Asn Glu Val Tyr Cys Asp Thr Cys Thr
       50                  55                  60
Ala Lys Tyr Gly Ala Ile His Ser Gly Tyr Gln Thr Ser Ala Asp Phe
 65                  70                  75                  80
Val Thr Thr Leu Pro Thr Thr Thr Gly Ala Ala Gly Gln Pro Thr Thr
               85                  90                  95
Thr Thr Thr Gly Ser Pro Ser Lys Pro Thr Thr Thr Thr Thr Ile Xaa
           100                 105                 110
Gly Asn Asn Asn His Asn Asn Ser Xaa Ser Asn His Tyr Asn Asn Asn
       115                 120                 125
Ser Lys Thr Asn Asn Asn Asn Asn Lys Gly Ser Arg Xaa Ala Thr
130                 135                 140
Asn Ser His Asn Asn Asn Asn Ile Lys Ala Asn Ser Tyr Asn Asn Asn
145                 150                 155                 160
Asn Lys Ser Asn Asn Asn Asn Asn Asn Ser Ala Asn Asp Asn Tyr
               165                 170                 175
Tyr Tyr Gln Glu Arg Arg Asn Asp Asn Asn Asn Asp Thr Ile Thr Xaa
           180                 185                 190
Tyr Arg Xaa His Xaa Asn Tyr Thr Asn Pro Asn Xaa Lys Asp Val Gly
           195                 200                 205
Xaa Val His Lys Asn Asp Leu Xaa Leu Xaa Gln Trp Phe Ile Ile Arg
       210                 215                 220
Leu Xaa Xaa Xaa Thr Asn Ser Arg Phe Ser Ser Arg Thr Asn Ser Xaa
225                 230                 235                 240
Tyr Lys Gln Phe Ile Pro Arg Phe Lys Leu Thr Arg Val Leu Val Tyr
               245                 250                 255
Gln Leu Ile Gln Trp Leu Val Phe His Leu Ile Gln Asn Gln Val Ile
           260                 265                 270
Xaa Tyr Ile His Ile Pro Ile Lys Gln Cys Leu Val Tyr Arg Tyr His
       275                 280                 285
Ile Leu Leu Leu Arg Ile Xaa Gln Leu Ile Leu Met Lys Leu Arg Phe
       290                 295                 300
Thr Asn Xaa Tyr Thr His Trp Leu Pro Ile Gly Ser Ser Gln Phe Asp
305                 310                 315                 320
Ser Val Gln Ser Arg Asn Trp Xaa Ile Val Cys Pro Ile Ser Asp Glu
               325                 330                 335
Ile Met Asn Gly Thr Ile Ala Gly Ile Val Ser Gly Ile Ser Ala Ser
           340                 345                 350
Glu Ser Leu Leu Ser Gln Lys Ser Leu
               355                 360
```

( 2 ) INFORMATION FOR SEQ ID NO:4:

( i ) SEQUENCE CHARACTERISTICS:
        ( A ) LENGTH: 361 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
  ( A ) ORGANISM: Cryptosporidium parvum ( i x ) FEATURE:
  ( A ) NAME/KEY: Positions coded by nonsense codons are identified as Xaa.

( x i ) SEQUENCE DESCRIPTION: SEQ ID NO: 4:

| | | | | | | | | | | | | | | | |
|---|---|---|---|---|---|---|---|---|---|---|---|---|---|---|---|
| Arg | Val | Pro | Arg | Xaa | Lys | Phe | Gly | Phe | His | Asn | Ser | Ser | Ser | Ser | Trp |
| | | | | 5 | | | | | 10 | | | | | 15 | |
| Pro | Xaa | Gln | Leu | Phe | Asn | Asn | Ser | Trp | Cys | Glu | Arg | Arg | Trp | Lys | Asn |
| | | | 20 | | | | | 25 | | | | | 30 | | |
| Ser | Arg | Lys | Pro | Ile | Arg | Phe | Xaa | Gly | Cys | Leu | Ser | Asn | Lys | Cys | Ser |
| | | 35 | | | | | 40 | | | | | 45 | | | |
| Asn | Thr | Thr | Phe | Xaa | Val | Ile | Gln | Xaa | Ser | Leu | Leu | Arg | His | Leu | Tyr |
| | 50 | | | | | 55 | | | | | 60 | | | | |
| Cys | Glu | Val | Trp | Cys | Asn | Ser | Leu | Trp | Ile | Ser | Asn | Phe | Ser | Xaa | Phe |
| 65 | | | | | 70 | | | | | 75 | | | | | 80 |
| Arg | Asn | Asn | Thr | Ser | Tyr | Tyr | Asn | Trp | Ser | Arg | Arg | Thr | Thr | Asn | Asn |
| | | | | 85 | | | | | 90 | | | | | 95 | |
| Tyr | Tyr | Asn | Trp | Lys | Ser | Lys | Gln | Thr | Asn | Tyr | Tyr | Tyr | His | Tyr | Leu |
| | | | 100 | | | | | 105 | | | | | 110 | | |
| Arg | Gln | Gln | Gln | Pro | Gln | Gln | Leu | Leu | Ile | Gln | Ser | Leu | Gln | Gln | Gln |
| | | 115 | | | | | 120 | | | | | 125 | | | |
| Leu | Lys | Asn | Gln | Gln | Gln | Gln | Gln | Gln | Gln | Arg | Phe | Gln | Val | Ser | His |
| | 130 | | | | | 135 | | | | | 140 | | | | |
| Gln | Xaa | Pro | Gln | Gln | Gln | Gln | His | Xaa | Ser | Gln | Xaa | Leu | Gln | Gln | Gln |
| 145 | | | | | 150 | | | | | 155 | | | | | 160 |
| Gln | Gln | Lys | Gln | Gln | Gln | Gln | Gln | Gln | Gln | Gln | Cys | Gln | Arg | Gln | Leu |
| | | | | 165 | | | | | 170 | | | | | 175 | |
| Leu | Leu | Pro | Arg | Glu | Thr | Lys | Xaa | Gln | Gln | Gln | Arg | His | His | Tyr | Leu |
| | | | 180 | | | | | 185 | | | | | 190 | | |
| Ile | Ser | Val | Thr | Leu | Lys | Leu | His | Gln | Ser | Gln | Leu | Lys | Arg | Cys | Trp |
| | | 195 | | | | | 200 | | | | | 205 | | | |
| Ile | Ser | Thr | Gln | Glu | Xaa | Phe | Met | Thr | Ile | Thr | Val | Val | Tyr | Tyr | Xaa |
| | 210 | | | | | 215 | | | | | 220 | | | | |
| Thr | Leu | Met | Met | Asn | Gln | Phe | Gln | Val | Leu | Lys | Gln | Asp | Lys | Xaa | Leu |
| 225 | | | | | 230 | | | | | 235 | | | | | 240 |
| Ile | Gln | Ala | Ile | Tyr | Ser | Gln | Val | Gln | Thr | His | Lys | Ser | Thr | Gly | Leu |
| | | | | 245 | | | | | 250 | | | | | 255 | |
| Pro | Ile | Asp | Pro | Met | Val | Gly | Leu | Pro | Phe | Asp | Pro | Lys | Ser | Gly | Asn |
| | | | 260 | | | | | 265 | | | | | 270 | | |
| Leu | Val | His | Pro | Tyr | Thr | Asn | Gln | Thr | Met | Ser | Gly | Leu | Ser | Val | Ser |
| | | 275 | | | | | 280 | | | | | 285 | | | |
| Tyr | Leu | Ala | Ala | Lys | Asn | Leu | Thr | Val | Asp | Thr | Asp | Glu | Thr | Thr | Val |
| | 290 | | | | | 295 | | | | | 300 | | | | |
| Tyr | Gln | Leu | Ile | His | Ser | Leu | Val | Thr | His | Trp | Ile | Gln | Ser | Val | Xaa |
| 305 | | | | | 310 | | | | | 315 | | | | | 320 |
| Phe | Arg | Ser | Ile | Gln | Lys | Leu | Val | Asn | Cys | Leu | Ser | Asn | Ile | Arg | Xaa |
| | | | | 325 | | | | | 330 | | | | | 335 | |
| Asp | Asn | Glu | Trp | Asn | Asn | Cys | Arg | Tyr | Cys | Phe | Arg | Asn | Phe | Cys | Lys |
| | | | 340 | | | | | 345 | | | | | 350 | | |
| Xaa | Val | Ile | Ile | Ile | Ser | Glu | Ile | Ala | | | | | | | |
| | | 355 | | | | | 360 | | | | | | | | |

( 2 ) INFORMATION FOR SEQ ID NO:5:

(i) SEQUENCE CHARACTERISTICS:
  (A) LENGTH: 362 amino acids
  (B) TYPE: amino acid
  (C) STRANDEDNESS: single
  (D) TOPOLOGY: linear (ii) MOLECULE TYPE: peptide (vi) ORIGINAL SOURCE:
  (A) ORGANISM: Cryptosporidium parvum (ix) FEATURE:
  (A) NAME/KEY: Positions coded by nonsense codons are
       identified as Xaa.

(xi) SEQUENCE DESCRIPTION: SEQ ID NO: 5:

| Ala | Ser | Ser | Gln | Ile | Glu | Val | Trp | Ile | Ser | Gln | Phe | Leu | Gln | Xaa | Leu |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Ala | Ile | Thr | Ala | Val | Gln | Xaa | Xaa | Leu | Val | Xaa | Ala | Ala | Met | Glu | Lys |
|     |     |     | 20  |     |     |     |     | 25  |     |     |     |     | 30  |     |     |
| Phe | Thr | Xaa | Ala | His | Thr | Val | Leu | Arg | Met | Ser | Leu | Xaa | Xaa | Val | Leu |
|     |     | 35  |     |     |     |     | 40  |     |     |     |     | 45  |     |     |     |
| Gln | Tyr | Asn | Leu | Leu | Ser | Tyr | Ser | Met | Lys | Phe | Ile | Ala | Thr | Leu | Val |
|     | 50  |     |     |     |     | 55  |     |     |     |     | 60  |     |     |     |     |
| Leu | Arg | Ser | Met | Val | Gln | Phe | Thr | Leu | Asp | Ile | Lys | Leu | Gln | Leu | Ile |
| 65  |     |     |     |     | 70  |     |     |     |     | 75  |     |     |     |     | 80  |
| Ser | Xaa | Gln | His | Phe | Leu | Leu | Gln | Leu | Glu | Pro | Gln | Asp | Asn | Gln | Gln |
|     |     |     |     | 85  |     |     |     |     | 90  |     |     |     |     | 95  |     |
| Leu | Leu | Gln | Leu | Glu | Val | Gln | Ala | Asn | Gln | Leu | Leu | Leu | Pro | Leu | Ser |
|     |     |     | 100 |     |     |     |     | 105 |     |     |     |     | 110 |     |     |
| Lys | Ala | Thr | Thr | Thr | Thr | Thr | Leu | Asn | Pro | Ile | Ile | Thr | Thr | Thr | Thr |
|     |     | 115 |     |     |     |     | 120 |     |     |     |     | 125 |     |     |     |
| Thr | Gln | Lys | Pro | Thr | Thr | Thr | Thr | Thr | Lys | Val | Pro | Gly | Lys | Pro |
|     | 130 |     |     |     |     | 135 |     |     |     |     | 140 |     |     |     |
| Pro | Ile | Ala | Thr | Thr | Thr | Thr | Leu | Lys | Pro | Ile | Val | Thr | Thr | Thr |
| 145 |     |     |     |     | 150 |     |     |     |     | 155 |     |     |     |     | 160 |
| Thr | Thr | Lys | Ala | Thr | Thr | Thr | Thr | Thr | Thr | Val | Pro | Thr | Thr | Thr |
|     |     |     |     | 165 |     |     |     |     | 170 |     |     |     |     | 175 |
| Thr | Thr | Thr | Lys | Arg | Asp | Glu | Met | Thr | Thr | Thr | Thr | Pro | Leu | Pro |
|     |     |     | 180 |     |     |     |     | 185 |     |     |     |     | 190 |     |
| Asp | Ile | Gly | Asp | Ile | Glu | Ile | Thr | Pro | Ile | Pro | Ile | Glu | Lys | Met | Leu |
|     |     | 195 |     |     |     |     | 200 |     |     |     |     | 205 |     |     |     |
| Asp | Lys | Tyr | Thr | Arg | Met | Ile | Tyr | Asp | Tyr | Asn | Ser | Gly | Leu | Leu | Leu |
|     | 210 |     |     |     |     | 215 |     |     |     |     | 220 |     |     |     |     |
| Asp | Ser | Asn | Asp | Glu | Pro | Ile | Pro | Gly | Ser | Gln | Ala | Gly | Gln | Ile | Ala |
| 225 |     |     |     |     | 230 |     |     |     |     | 235 |     |     |     |     | 240 |
| Asp | Thr | Ser | Asn | Leu | Phe | Pro | Gly | Ser | Asn | Ser | Gln | Glu | Tyr | Trp | Phe |
|     |     |     |     | 245 |     |     |     |     | 250 |     |     |     |     | 255 |     |
| Thr | Asn | Xaa | Ser | Asn | Gly | Trp | Ser | Ser | Ile | Xaa | Ser | Lys | Ile | Arg | Xaa |
|     |     |     | 260 |     |     |     |     | 265 |     |     |     |     | 270 |     |     |
| Phe | Ser | Thr | Ser | Ile | Tyr | Gln | Ser | Asn | Asn | Val | Trp | Phe | Ile | Gly | Ile |
|     |     | 275 |     |     |     |     | 280 |     |     |     |     | 285 |     |     |     |
| Ile | Ser | Cys | Cys | Xaa | Glu | Phe | Asp | Ser | Xaa | Tyr | Xaa | Xaa | Asn | Tyr | Gly |
|     | 290 |     |     |     |     | 295 |     |     |     |     | 300 |     |     |     |     |
| Leu | Pro | Ile | Asp | Thr | Leu | Thr | Gly | Tyr | Pro | Leu | Asp | Pro | Val | Ser | Leu |
| 305 |     |     |     |     | 310 |     |     |     |     | 315 |     |     |     |     | 320 |
| Ile | Pro | Phe | Asn | Pro | Glu | Thr | Gly | Glu | Leu | Phe | Val | Gln | Tyr | Gln | Met |
|     |     |     |     | 325 |     |     |     |     | 330 |     |     |     |     | 335 |     |

```
Arg Xaa Xaa Met Glu Gln Leu Gln Val Leu Phe Gln Glu Phe Leu Gln
            340                 345                 350

Val Ser His Tyr Tyr Leu Arg Asn Arg Ser
        355                 360
```

( 2 ) INFORMATION FOR SEQ ID NO:6:

( i ) SEQUENCE CHARACTERISTICS:
        ( A ) LENGTH: 362 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
              identified as Xaa.

( x i ) SEQUENCE DESCRIPTION: SEQ ID NO: 6:

```
Gly Ala Ile Ser Glu Ile Ile Met Thr His Leu Gln Lys Phe Leu Lys
1               5                   10                  15

Gln Tyr Leu Gln Leu Phe His Ser Leu Ser His Leu Ile Leu Asp Lys
            20                  25                  30

Gln Phe Thr Ser Phe Trp Ile Glu Arg Asn Gln Thr Asp Trp Ile Gln
        35                  40                  45

Trp Val Thr Ser Glu Cys Ile Asn Trp Xaa Thr Val Val Ser Ser Val
    50                  55                  60

Ser Thr Val Lys Phe Leu Ala Ala Arg Tyr Asp Thr Asp Lys Pro Asp
65                  70                  75                  80

Ile Val Xaa Leu Val Tyr Gly Cys Thr Lys Leu Pro Asp Phe Gly Ser
                85                  90                  95

Asn Gly Arg Pro Thr Ile Gly Ser Ile Gly Lys Pro Val Leu Leu Xaa
            100                 105                 110

Val Xaa Thr Trp Glu Xaa Ile Ala Cys Ile Ser Tyr Leu Ser Cys Leu
        115                 120                 125

Arg Thr Trp Asn Trp Phe Ile Ile Arg Val Xaa Xaa Xaa Thr Thr Val
    130                 135                 140

Ile Val Ile Asn His Ser Cys Val Leu Ile Gln His Leu Phe Asn Trp
145                 150                 155                 160

Asp Trp Cys Asn Phe Asn Val Thr Asp Ile Arg Xaa Trp Cys Arg Cys
                165                 170                 175

Cys Cys His Phe Val Ser Leu Gly Ser Ser Ser Cys Arg Trp His Cys
            180                 185                 190

Cys Cys Cys Cys Cys Cys Cys Phe Cys Cys Cys Cys Asn Tyr Trp
        195                 200                 205

Leu Xaa Cys Cys Cys Cys Cys Gly Tyr Trp Trp Leu Thr Trp Asn Leu
        210                 215                 220

Cys Cys Cys Cys Cys Cys Trp Phe Leu Ser Cys Cys Cys Asn Asp Trp
225                 230                 235                 240

Ile Lys Ser Cys Cys Gly Cys Cys Cys Leu Arg Xaa Trp Xaa Xaa Xaa
                245                 250                 255

Leu Val Cys Leu Asp Phe Gln Leu Xaa Xaa Leu Leu Val Val Leu Arg
            260                 265                 270

Leu Gln Leu Xaa Xaa Glu Val Leu Leu Arg Asn Gln Leu Lys Phe Asp
        275                 280                 285
```

```
Ile Gln Ser Glu Leu His His Thr Ser Gln Tyr Lys Cys Arg Asn Lys
290                     295                 300

Leu His Xaa Ile Thr Gln Lys Val Val Leu Glu His Leu Leu Glu Arg
305                 310                 315                 320

His Pro Xaa Asn Arg Met Gly Leu Arg Glu Phe Phe His Arg Arg Ser
                325                 330                 335

His Gln Leu Leu Leu Asn Ser Cys Tyr Gly Gln Leu Leu Glu Glu Leu
            340                 345                 350

Xaa Asn Pro Asn Phe Tyr Leu Gly Thr Arg
            355                 360
```

( 2 ) INFORMATION FOR SEQ ID NO:7:

( i ) SEQUENCE CHARACTERISTICS:
        ( A ) LENGTH: 361 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 7:

```
Ser Asp Phe Xaa Asp Asn Asn Asp Ser Leu Ala Glu Ile Pro Glu Thr
1               5                   10                  15

Ile Pro Ala Ile Val Pro Phe Ile Ile Ser Ser Asp Ile Gly Gln Thr
                20                  25                  30

Ile His Gln Phe Leu Asp Xaa Thr Glu Ser Asn Xaa Leu Asp Pro Met
            35                  40                  45

Gly Asn Gln Xaa Val Tyr Gln Leu Val Asn Arg Ser Phe Ile Ser Ile
    50                  55                  60

Asn Cys Gln Ile Leu Ser Ser Lys Ile Xaa Tyr Arg Xaa Thr Arg His
65                  70                  75                  80

Cys Leu Ile Gly Ile Trp Met Tyr Xaa Ile Thr Xaa Phe Trp Ile Lys
                85                  90                  95

Trp Lys Thr Asn His Trp Ile Asn Trp Xaa Thr Ser Thr Leu Val Ser
                100                 105                 110

Leu Asn Leu Gly Ile Asn Cys Leu Tyr Gln Leu Phe Val Leu Leu Glu
            115                 120                 125

Asn Leu Glu Leu Val His His Xaa Ser Leu Ile Ile Asn His Cys Tyr
    130                 135                 140

Ser His Lys Ser Phe Leu Cys Thr Tyr Pro Thr Ser Phe Gln Leu Gly
145                 150                 155                 160

Leu Val Xaa Phe Gln Cys His Arg Tyr Gln Val Met Val Ser Leu Leu
                165                 170                 175

Leu Ser Phe Arg Leu Ser Trp Xaa Xaa Xaa Leu Ser Leu Ala Leu Leu
            180                 185                 190

Leu Leu Leu Leu Leu Leu Leu Leu Leu Leu Leu Xaa Leu Leu Ala
    195                 200                 205

Leu Met Leu Leu Leu Leu Trp Leu Leu Val Ala Tyr Leu Glu Pro Leu
    210                 215                 220

Leu Leu Leu Leu Leu Leu Val Phe Glu Leu Leu Leu Xaa Xaa Leu Asp
225                 230                 235                 240
```

| Xaa | Glu | Leu | Leu | Trp<br>245 | Leu | Leu | Leu | Pro | Xaa<br>250 | Ile | Val | Val | Val | Val<br>255 |
|---|---|---|---|---|---|---|---|---|---|---|---|---|---|---|
| Gly | Leu | Leu | Gly<br>260 | Leu | Pro | Val | Val<br>265 | Val | Val | Gly | Cys | Pro<br>270 | Ala | Ala |
| Pro | Val | Val<br>275 | Val | Gly | Ser | Val | Thr<br>280 | Lys | Ser | Ala | Glu<br>285 | Val | Xaa | Tyr |
| Pro | Glu<br>290 | Xaa | Ile | Ala | Pro | Tyr<br>295 | Phe | Ala | Val | Gln<br>300 | Val | Ser | Gln | Xaa | Thr |
| Ser<br>305 | Leu | Asn | Asn | Ser | Glu<br>310 | Gly | Cys | Ile | Gly | Ala<br>315 | Leu | Ile | Arg | Glu | Thr<br>320 |
| Ser | Leu | Glu | Pro | Tyr<br>325 | Gly | Leu | Thr | Xaa<br>330 | Ile | Phe | Pro | Ser | Pro | Leu<br>335 | Thr |
| Pro | Thr | Ile | Ile<br>340 | Glu | Gln | Leu | Leu | Trp<br>345 | Pro | Ala | Thr | Gly<br>350 | Gly | Ile | Val |
| Lys | Ser | Lys<br>355 | Leu | Leu | Ser | Gly | Asn<br>360 | Ser |

(2) INFORMATION FOR SEQ ID NO:8:

(i) SEQUENCE CHARACTERISTICS:
        (A) LENGTH: 361 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cryptosporidium parvum (ix) FEATURE:
        (A) NAME/KEY: Positions coded by nonsense codons are identified as Xaa.

(xi) SEQUENCE DESCRIPTION: SEQ ID NO: 8:

| Glu<br>1 | Arg | Phe | Leu | Arg<br>5 | Xaa | Xaa | Xaa | Leu | Thr<br>10 | Cys | Arg | Asn | Ser | Xaa<br>15 | Asn |
|---|---|---|---|---|---|---|---|---|---|---|---|---|---|---|---|
| Asn | Thr | Cys | Asn<br>20 | Cys | Ser | Ile | His | Tyr<br>25 | Leu | Ile | Xaa | Tyr | Trp<br>30 | Thr | Asn |
| Asn | Ser | Pro<br>35 | Val | Ser | Gly | Leu | Asn<br>40 | Gly | Ile | Lys | Leu | Thr<br>45 | Gly | Ser | Asn |
| Gly | Xaa<br>50 | Pro | Val | Ser | Val | Ser<br>55 | Ile | Gly | Lys | Pro | Xaa<br>60 | Phe | His | Gln | Tyr |
| Gln<br>65 | Leu | Ser | Asn | Ser | Xaa<br>70 | Gln | Gln | Asp | Met | Ile<br>75 | Pro | Ile | Asn | Gln | Thr<br>80 |
| Leu | Phe | Asp | Trp | Tyr<br>85 | Met | Asp | Val | Leu | Asn<br>90 | Tyr | Leu | Ile | Leu | Asp<br>95 | Gln |
| Met | Glu | Asp | Gln | Pro<br>100 | Leu | Asp | Gln | Leu | Val<br>105 | Asn | Gln | Tyr | Ser | Cys<br>110 | Glu |
| Phe | Glu | Pro | Gly<br>115 | Asn | Lys | Leu | Leu | Val<br>120 | Ser | Ala | Ile | Cys<br>125 | Pro | Ala | Xaa |
| Glu | Pro<br>130 | Gly | Ile | Gly | Ser | Ser<br>135 | Leu | Glu | Ser | Asn | Asn<br>140 | Lys | Pro | Leu | Leu |
| Xaa<br>145 | Ser | Xaa | Ile | Ile | Leu<br>150 | Val | Tyr | Leu | Ser | Asn<br>155 | Ile | Phe | Ser | Ile | Gly<br>160 |
| Ile | Gly | Val | Ile | Ser<br>165 | Met | Ser | Pro | Ile | Ser<br>170 | Gly | Asn | Gly | Val | Val<br>175 | Val |
| Val | Val | Ile | Ser<br>180 | Ser | Leu | Leu | Val | Val<br>185 | Val | Val | Val | Val | Gly<br>190 | Thr | Val |

| | | | | | | | | | | | | | | |
|---|---|---|---|---|---|---|---|---|---|---|---|---|---|---|
| Val | Val | Val | Val | Val | Val | Ala | Phe | Val | Val | Val | Val | Thr | Ile | Gly |
| | | 195 | | | | | 200 | | | | 205 | | | |
| Phe | Asn | Val | Val | Val | Val | Val | Ala | Ile | Gly | Gly | Leu | Pro | Gly | Thr | Phe |
| | 210 | | | | | 215 | | | | | 220 | | | | |
| Val | Val | Val | Val | Val | Val | Gly | Phe | Xaa | Val | Val | Val | Val | Met | Ile | Gly |
| 225 | | | | | 230 | | | | | | 235 | | | | 240 |
| Leu | Arg | Val | Val | Val | Val | Val | Val | Ala | Leu | Asp | Ser | Gly | Ser | Ser | Ser |
| | | | | 245 | | | | | 250 | | | | | 255 | |
| Trp | Phe | Ala | Trp | Thr | Ser | Ser | Cys | Ser | Ser | Cys | Trp | Leu | Ser | Cys | Gly |
| | | | 260 | | | | | | 265 | | | | 270 | | |
| Ser | Ser | Cys | Ser | Arg | Lys | Cys | Cys | Tyr | Glu | Ile | Ser | Xaa | Ser | Leu | Ile |
| | | 275 | | | | | 280 | | | | | 285 | | | |
| Ser | Arg | Val | Asn | Cys | Thr | Ile | Leu | Arg | Ser | Thr | Ser | Val | Ala | Ile | Asn |
| | 290 | | | | | 295 | | | | | 300 | | | | |
| Phe | Ile | Glu | Xaa | Leu | Arg | Arg | Leu | Tyr | Trp | Ser | Thr | Tyr | Xaa | Arg | Asp |
| 305 | | | | | 310 | | | | | 315 | | | | | 320 |
| Ile | Leu | Arg | Thr | Val | Trp | Ala | Tyr | Val | Asn | Phe | Ser | Ile | Ala | Ala | His |
| | | | | 325 | | | | | 330 | | | | | 335 | |
| Thr | Asn | Tyr | Tyr | Xaa | Thr | Ala | Val | Met | Ala | Ser | Tyr | Trp | Arg | Asn | Cys |
| | | | 340 | | | | | 345 | | | | | 350 | | |
| Glu | Ile | Gln | Thr | Ser | Ile | Trp | Glu | Leu | | | | | | | |
| | | 355 | | | | | 360 | | | | | | | | |

( 2 ) INFORMATION FOR SEQ ID NO:9:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 9:

| | | | | | | | | | | | | | | |
|---|---|---|---|---|---|---|---|---|---|---|---|---|---|---|
| Phe | Arg | Gln | Leu | Met | Pro | Asn | Asn | Gln | Leu | Arg | Leu | Ala | Arg | Gly | Gly |
| | | | | 5 | | | | | 10 | | | | | 15 | |
| Asn | Leu | Cys | Xaa | Gln | Val | Gln | Glu | Ile | Ser | Gln | Glu | Ser | Arg | Met | Leu |
| | | | 20 | | | | | 25 | | | | | 30 | | |
| His | Xaa | Thr | Gln | Gln | Pro | Val | Pro | Gln | Val | Cys | Xaa | Thr | Val | | |
| | | 35 | | | | | 40 | | | | | 45 | | | |

( 2 ) INFORMATION FOR SEQ ID NO:10:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
( A ) NAME/KEY: Positions coded by nonsense codons are identified as Xaa.

( x i ) SEQUENCE DESCRIPTION: SEQ ID NO: 10:

Ile Pro Ala Ile Asn Ala Lys Gln Ser Ala Gln Ile Ser Xaa Arg Trp
                 5                   10                  15

Lys Ser Met Leu Thr Ser Pro Gly Asp Lys Pro Gly Val Ala Asn Val
             20                  25                  30

Ala Leu Asn Ser Ala Ala Ser Ser Thr Ser Val Leu Asp Ser
             35              40                  45

( 2 ) INFORMATION FOR SEQ ID NO:11:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 11:

Asn Ser Gly Asn Xaa Cys Gln Thr Ile Ser Ser Asp Xaa Leu Glu Val
                 5                   10                  15

Glu Ile Tyr Val Asn Lys Ser Arg Arg Xaa Ala Arg Ser Arg Glu Cys
             20                  25                  30

Cys Ile Lys Leu Ser Ser Gln Phe His Lys Cys Val Arg Gln Tyr
             35              40                  45

( 2 ) INFORMATION FOR SEQ ID NO:12:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 12:

Ile Leu Ser Asn Thr Leu Val Glu Leu Ala Ala Glu Phe Asn Ala Thr
1                5                   10                  15

Phe Ala Thr Pro Gly Leu Ser Pro Gly Leu Val Asn Ile Asp Phe His
             20                  25                  30

Leu Xaa Leu Ile Xaa Ala Asp Cys Leu Ala Leu Ile Ala Gly Ile
             35              40                  45

( 2 ) INFORMATION FOR SEQ ID NO:13:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide (v i) ORIGINAL SOURCE:
    (A) ORGANISM: Cryptosporidium parvum (i x) FEATURE:
    (A) NAME/KEY: Positions coded by nonsense codons are
        identified as Xaa.

(x i) SEQUENCE DESCRIPTION: SEQ ID NO: 13:

| Thr | Val | Xaa | His | Thr | Cys | Gly | Thr | Gly | Cys | Xaa | Val | Xaa | Cys | Asn | Ile |
|---|---|---|---|---|---|---|---|---|---|---|---|---|---|---|---|
| 1 | | | | 5 | | | | | 10 | | | | | | 15 |

| Arg | Asp | Ser | Trp | Leu | Ile | Ser | Trp | Thr | Cys | Xaa | His | Arg | Phe | Pro | Pro |
|---|---|---|---|---|---|---|---|---|---|---|---|---|---|---|---|
| | | | 20 | | | | | 25 | | | | | 30 | | |

| Leu | Ala | Asn | Leu | Ser | Xaa | Leu | Phe | Gly | Ile | Asn | Cys | Arg | Asn |
|---|---|---|---|---|---|---|---|---|---|---|---|---|---|
| | | 35 | | | | | 40 | | | | | 45 | |

(2) INFORMATION FOR SEQ ID NO:14:

(i) SEQUENCE CHARACTERISTICS:
        (A) LENGTH: 46 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Cryptosporidium parvum (i x) FEATURE:
        (A) NAME/KEY: Positions coded by nonsense codons are
            identified as Xaa.

(x i) SEQUENCE DESCRIPTION: SEQ ID NO: 14:

| Tyr | Cys | Leu | Thr | His | Leu | Trp | Asn | Trp | Leu | Leu | Ser | Leu | Met | Gln | His |
|---|---|---|---|---|---|---|---|---|---|---|---|---|---|---|---|
| 1 | | | | 5 | | | | | 10 | | | | | | 15 |

| Ser | Arg | Leu | Leu | Ala | Tyr | Leu | Leu | Asp | Leu | Leu | Thr | Xaa | Ile | Ser | Thr |
|---|---|---|---|---|---|---|---|---|---|---|---|---|---|---|---|
| | | | 20 | | | | | 25 | | | | | 30 | | |

| Ser | Ser | Xaa | Ser | Glu | Leu | Ile | Val | Trp | His | Xaa | Leu | Pro | Glu |
|---|---|---|---|---|---|---|---|---|---|---|---|---|---|
| | | 35 | | | | | 40 | | | | | 45 | |

(2) INFORMATION FOR SEQ ID NO:15:

(i) SEQUENCE CHARACTERISTICS:
        (A) LENGTH: 350 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Cryptosporidium parvum (i x) FEATURE:
        (A) NAME/KEY: Positions coded by nonsense codons are
            identified as Xaa.

(x i) SEQUENCE DESCRIPTION: SEQ ID NO: 15:

| Gly | Asn | Tyr | Pro | Ser | Leu | Leu | Leu | Arg | Asp | Ile | Thr | Glu | Asp | Ile | Xaa |
|---|---|---|---|---|---|---|---|---|---|---|---|---|---|---|---|
| | | | | 5 | | | | | 10 | | | | | | 15 |

| Val | Gln | Asn | Lys | Leu | Thr | Leu | Asn | Gln | Xaa | Ile | Gln | Phe | Val | Asn | Leu |
|---|---|---|---|---|---|---|---|---|---|---|---|---|---|---|---|
| | | | 20 | | | | | 25 | | | | | 30 | | |

| Ile | Xaa | Phe | Pro | Val | Lys | Xaa | Asn | Ile | Phe | Tyr | Lys | Ile | Arg | Tyr | Tyr |
|---|---|---|---|---|---|---|---|---|---|---|---|---|---|---|---|
| | | 35 | | | | | 40 | | | | | 45 | | | |

| Ser | Ile | Leu | Lys | Tyr | Thr | Ile | Val | Tyr | Xaa | Asn | Glu | Tyr | Ile | Ser | Xaa |
|---|---|---|---|---|---|---|---|---|---|---|---|---|---|---|---|
| | 50 | | | | | 55 | | | | | 60 | | | | |

| | | | | | | | | | | | | | | | |
|---|---|---|---|---|---|---|---|---|---|---|---|---|---|---|---|
| Lys 65 | Val | Ser | Thr | Lys 70 | Leu | Tyr | Cys | Xaa | Ser 75 | Cys | Tyr | Gly | Arg | Trp | Phe 80 |
| Ile | Gln | Glu | Gly | Leu 85 | Leu | Glu | Arg | Leu 90 | Gln | Arg | Lys | Ile | Arg 95 | Cys | Ile |
| Val | Leu | Leu | Ser 100 | Ile | Lys | Leu | His 105 | Ile | Cys | Met | Ser | Ile 110 | Xaa | Asn | Leu |
| Ser | Ile | Gln 115 | Ser | Ser | Thr | Lys 120 | Arg | Leu | Xaa | Glu | Ile 125 | Gly | Ser | Thr | Ala |
| Pro | Leu 130 | Val | Cys | Ser | Val 135 | Asp | Ser | Gln | Tyr | Ser 140 | His | Ala | Ala | Trp | Arg |
| Arg 145 | Thr | Pro | Leu | Glu 150 | Gln | Gly | Gly | Ile | Gly 155 | Pro | Val | Asn | Phe | Pro | Leu 160 |
| Ile | Ser | Asp | Ser 165 | Ser | His | Ser | Ile | Ser 170 | Lys | Asn | Tyr | Gly | Val 175 | Leu | Ser |
| Arg | Gly | Arg | Arg 180 | Tyr | Cys | Ser | Gln | Arg 185 | Phe | Ile | His | His | Xaa 190 | Gln | Gly |
| Gly | Ser | Arg 195 | Cys | Ser | Phe | Xaa | Ser 200 | Asn | Leu | Xaa | Leu | Thr 205 | Ile | Arg | Lys |
| Ile | Ser 210 | Arg | Arg | Asn | Ser | Thr 215 | Cys | Tyr | Xaa | Cys | Thr 220 | Ser | Ile | His | Xaa |
| Asn 225 | Leu | Trp | Xaa | Ser | Leu 230 | Pro | Ser | Lys | Leu | Glu 235 | Glu | Gly | Pro | Lys | Arg 240 |
| Asn | Val | Ser | Tyr | Ser 245 | Xaa | Arg | Cys | Phe | Gln 250 | Leu | Ser | Xaa | Gly | Leu 255 | Ile |
| Leu | Glu | Xaa | Phe 260 | Asn | Phe | Ser | Asn | Glu 265 | Pro | Asn | Phe | Phe | Leu 270 | Ile | Xaa |
| Leu | Phe | Leu 275 | Cys | Ser | Tyr | Lys | Ser 280 | Asp | Ala | Asn | Glu | Tyr 285 | Arg | Arg | Leu |
| His | Ile 290 | Xaa | Ile | Leu | Cys | Gly 295 | Asp | Xaa | Ile | Val | Glu 300 | Xaa | Val | Gln | Ile |
| Asn 305 | Pro | Gly | Val | Val | Asn 310 | Val | Val | Leu | Asn | Phe 315 | Cys | Asn | Leu | Ser | Phe 320 |
| Phe | Phe | Leu | Leu | Thr 325 | Tyr | Leu | Ser | Trp | Cys 330 | Xaa | Gln | Ser | Ser | Ile 335 | Arg |
| Asn | His | Tyr | Ser 340 | Ser | Ser | Lys | Ala | Gly 345 | Arg | Arg | Ser | Pro | Xaa 350 | | |

( 2 ) INFORMATION FOR SEQ ID NO:16:

( i ) SEQUENCE CHARACTERISTICS:
        ( A ) LENGTH: 350 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 16:

| | | | | | | | | | | | | | | | |
|---|---|---|---|---|---|---|---|---|---|---|---|---|---|---|---|
| Arg | Glu | Leu | Pro | Leu 5 | Ile | Ile | Ala | Ser | Arg 10 | Tyr | Asn | Xaa | Gly | Tyr 15 | Leu |
| Gly | Thr | Lys | Xaa 20 | Ile | Asp | Leu | Glu | Ser 25 | Ile | Asn | Ser | Ile | Cys 30 | Glu | Phe |

Asn Leu Ile Ser Ser Lys Val Lys Tyr Phe Leu Gln Asn Ser Leu Leu
            35                  40                  45

Phe His Phe Lys Val Tyr Asn Ser Leu Leu Lys Xaa Val His Xaa Leu
        50                  55                  60

Glu Ser Xaa His Gln Thr Leu Leu Leu Lys Leu Leu Trp Gln Met Val
65                      70                  75                  80

His Ser Arg Arg Ser Pro Xaa Ala Thr Thr Glu Glu Asn Thr Leu Tyr
                85                  90                  95

Cys Ser Ser Ile His Xaa Thr Ser His Leu Tyr Val His Leu Lys Ser
            100                 105                 110

Xaa His Ser Ile Lys His Lys Lys Thr Leu Arg Asn Trp Glu Tyr Ser
        115                 120                 125

Ser Ser Arg Val Leu Ser Xaa Phe Ser Ile Leu Pro Cys Cys Met Glu
    130                 135                 140

Thr Tyr Ser Ser Xaa Thr Arg Trp Asn Trp Thr Ser Gln Phe Pro Thr
145                 150                 155                 160

Tyr Leu Xaa Leu Ile Ser Phe Asn Xaa Gln Glu Leu Trp Cys Thr Phe
                165                 170                 175

Ser Arg Lys Lys Val Leu Leu Ser Glu Val Tyr Ser Ser Leu Thr Arg
            180                 185                 190

Arg Val Ala Leu Phe Val Leu Lys Xaa Ser Met Thr Tyr His Xaa Glu
        195                 200                 205

Asp Gln Ser Lys Lys Leu Tyr Val Leu Leu Met His Phe Asn Ser Leu
    210                 215                 220

Lys Pro Met Val Lys Phe Ala Gln Gln Thr Gly Arg Arg Ala Lys Lys
225                 230                 235                 240

Glu Cys Gln Leu Leu Met Lys Val Phe Pro Val Ile Leu Arg Thr His
                245                 250                 255

Phe Arg Met Ile Xaa Phe Phe Lys Xaa Thr Lys Phe Phe Phe Asn Leu
            260                 265                 270

Thr Phe Phe Met Xaa Leu Xaa Ile Arg Cys Lys Xaa Val Ser Ser Ser
        275                 280                 285

Pro His Leu Asp Pro Leu Trp Arg Leu Asp Cys Gly Ile Gly Ala Asn
    290                 295                 300

Lys Pro Trp Ser Cys Xaa Cys Ser Val Lys Phe Leu Xaa Phe Ile Phe
305                 310                 315                 320

Phe Phe Leu Ile Asn Leu Pro Phe Leu Val Leu Ala Val Phe Tyr Xaa
                325                 330                 335

Lys Ser Leu Leu Phe Phe Gln Gly Arg Lys Lys Val Ser Leu
            340                 345                 350

( 2 ) INFORMATION FOR SEQ ID NO:17:

( i ) SEQUENCE CHARACTERISTICS:
      ( A ) LENGTH: 351 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: Cryptosporidium parvum ( i x ) FEATURE:
      ( A ) NAME/KEY: Positions coded by nonsense codons are
            identified as Xaa.

( x i ) SEQUENCE DESCRIPTION: SEQ ID NO: 17:

| | | | | | | | | | | | | | | |
|---|---|---|---|---|---|---|---|---|---|---|---|---|---|---|
| Pro | Gly | Ile | Thr | Pro<br>5 | His | Tyr | Cys | Phe | Glu<br>10 | Ile | Xaa | Leu | Arg | Ile<br>15 | Phe |

Pro Gly Ile Thr Pro His Tyr Cys Phe Glu Ile Xaa Leu Arg Ile Phe
                    5                       10                    15
Arg Tyr Lys Ile Asn Xaa Pro Xaa Ile Asn Lys Phe Asn Leu Xaa Ile
                 20              25                      30
Xaa Phe Asn Phe Gln Xaa Ser Glu Ile Phe Phe Thr Lys Phe Ala Ile
             35              40                  45
Ile Pro Phe Xaa Ser Ile Gln Xaa Ser Ile Glu Met Ser Thr Leu Val
    50                  55              60
Arg Lys Leu Ala Pro Asn Phe Thr Ala Glu Ala Val Met Ala Asp Gly
65                  70              75                          80
Ser Phe Lys Lys Val Ser Leu Ser Asp Tyr Arg Gly Lys Tyr Val Val
                85                  90                      95
Leu Phe Phe Tyr Pro Leu Asn Phe Thr Phe Val Cys Pro Ser Glu Ile
            100             105                 110
Leu Ala Phe Asn Gln Ala Gln Lys Asp Phe Glu Lys Leu Gly Val Gln
            115             120                 125
Leu Leu Ser Cys Ala Gln Leu Ile Leu Asn Thr Pro Met Leu His Gly
    130                 135                 140
Asp Val Leu Leu Leu Asn Lys Val Glu Leu Asp Gln Ser Ile Ser His
145                 150                 155                     160
Leu Ser Leu Thr His Leu Ile Gln Leu Ala Arg Thr Met Val Tyr Phe
                165                 170                 175
Leu Glu Glu Glu Gly Ile Ala Leu Arg Gly Leu Phe Ile Ile Asp Lys
            180                 185             190
Glu Gly Arg Val Val Arg Ser Glu Val Ile Tyr Asp Leu Pro Leu Gly
        195                 200             205
Arg Ser Val Glu Glu Thr Leu Arg Val Ile Asp Ala Leu Gln Phe Thr
    210             215                 220
Glu Thr Tyr Gly Glu Val Cys Pro Ala Asn Trp Lys Lys Gly Gln Lys
225             230                 235                     240
Gly Met Ser Ala Thr His Glu Gly Val Ser Ser Tyr Leu Lys Asp Ser
            245                 250                 255
Phe Xaa Asn Asp Leu Ile Phe Gln Met Asn Gln Ile Phe Phe Xaa Ser
        260             265                 270
Asp Phe Phe Tyr Val Val Ile Asn Gln Met Gln Met Ser Ile Val Val
    275             280                 285
Ser Thr Ser Arg Ser Ser Val Ala Thr Arg Leu Trp Asn Arg Cys Lys
    290             295                 300
Xaa Thr Leu Glu Leu Leu Met Xaa Cys Xaa Ile Phe Val Ile Tyr Leu
305             310                 315                     320
Phe Phe Ser Tyr Xaa Leu Thr Phe Leu Gly Val Ser Ser Leu Leu Leu
            325                 330                 335
Glu Ile Ile Thr Leu Leu Pro Arg Pro Glu Glu Gly Leu Leu Glu
            340             345                 350

( 2 ) INFORMATION FOR SEQ ID NO:18:

( i ) SEQUENCE CHARACTERISTICS:
        ( A ) LENGTH: 351 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
    ( A ) NAME/KEY: Positions coded by nonsense codons are identified as Xaa.

( x i ) SEQUENCE DESCRIPTION: SEQ ID NO: 18:

| Leu<br>1 | Lys | Glu | Thr | Phe<br>5 | Phe | Arg | Pro | Trp | Lys<br>10 | Lys | Ser | Asn | Asp | Phe<br>15 | Xaa |
|---|---|---|---|---|---|---|---|---|---|---|---|---|---|---|---|
| Xaa | Lys | Thr | Ala<br>20 | Asn | Thr | Lys | Lys | Gly<br>25 | Lys | Leu | Ile | Arg | Lys<br>30 | Lys | Lys |
| Ile | Asn | Tyr<br>35 | Lys | Asn | Leu | Thr | Leu<br>40 | His | Xaa | Gln | Leu | Gln<br>45 | Gly | Leu | Phe |
| Ala | Pro<br>50 | Ile | Pro | Gln | Ser | Ser<br>55 | Arg | His | Arg | Gly | Ser<br>60 | Arg | Cys | Gly | Asp |
| Asp<br>65 | Asp | Thr | His | Leu | His<br>70 | Leu | Ile | Tyr | Asn | Tyr<br>75 | Ile | Lys | Lys | Val | Arg<br>80 |
| Leu | Lys | Lys | Asn | Leu<br>85 | Val | His | Leu | Lys | Asn<br>90 | Xaa | Ile | Ile | Leu | Lys<br>95 | Xaa |
| Val | Leu | Lys | Ile<br>100 | Thr | Gly | Asn | Thr | Phe<br>105 | Met | Ser | Ser | Xaa | His<br>110 | Ser | Phe |
| Leu | Ala | Leu<br>115 | Leu | Pro | Val | Cys | Trp<br>120 | Ala | Asn | Phe | Thr | Ile<br>125 | Gly | Phe | Ser |
| Glu | Leu<br>130 | Lys | Cys | Ile | Asn | Asn<br>135 | Thr | Xaa | Ser | Phe | Phe<br>140 | Asp | Xaa | Ser | Ser |
| Xaa<br>145 | Trp | Xaa | Val | Ile | Asp<br>150 | Tyr | Phe | Arg | Thr | Asn<br>155 | Asn | Ala | Thr | Leu | Leu<br>160 |
| Val | Asn | Asp | Glu | Xaa<br>165 | Thr | Ser | Glu | Ser | Asn<br>170 | Thr | Phe | Phe | Leu | Glu<br>175 | Lys |
| Val | His | His | Ser<br>180 | Ser | Cys | Xaa | Leu | Asn<br>185 | Glu | Met | Ser | Gln | Arg<br>190 | Xaa | Val |
| Gly | Asn | Xaa<br>195 | Leu | Val | Gln | Phe | His<br>200 | Leu | Val | Gln | Glu | Glu<br>205 | Tyr | Val | Ser |
| Met | Gln<br>210 | His | Gly | Ser | Ile | Glu<br>215 | Asn | Gln | Leu | Ser | Thr<br>220 | Arg | Glu | Glu | Leu |
| Tyr<br>225 | Ser | Gln | Phe | Leu | Lys<br>230 | Val | Phe | Leu | Cys | Leu<br>235 | Ile | Glu | Cys | Xaa | Asp<br>240 |
| Phe | Arg | Trp | Thr | Tyr<br>245 | Lys | Cys | Glu | Val | Xaa<br>250 | Trp | Ile | Glu | Glu | Gln<br>255 | Tyr |
| Asn | Val | Phe | Ser<br>260 | Ser | Val | Val | Ala | Gln<br>265 | Gly | Asp | Leu | Leu | Glu<br>270 | Xaa | Thr |
| Ile | Cys | His<br>275 | Asn | Ser | Phe | Ser | Ser<br>280 | Lys | Val | Trp | Cys | Xaa<br>285 | Leu | Ser | Asn |
| Xaa<br>290 | Cys | Thr | His | Phe | Asn<br>295 | Arg | Leu | Leu | Tyr | Thr<br>300 | Leu | Lys | Trp | Asn | Asn |
| Ser<br>305 | Glu | Phe | Cys | Lys | Lys<br>310 | Tyr | Phe | Thr | Leu | Leu<br>315 | Glu | Ile | Lys | Leu | Asn<br>320 |
| Ser | Gln | Ile | Glu | Phe<br>325 | Ile | Asp | Ser | Arg | Ser<br>330 | Ile | Tyr | Phe | Val | Pro<br>335 | Lys |
| Tyr | Pro | Gln | Leu | Tyr<br>340 | Leu | Glu | Ala | Ile | Met<br>345 | Arg | Gly | Asn | Ser | Arg<br>350 | |

( 2 ) INFORMATION FOR SEQ ID NO:19:

( i ) SEQUENCE CHARACTERISTICS:
        ( A ) LENGTH: 350 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
  ( A ) ORGANISM: Cryptosporidium parvum ( i x ) FEATURE:
  ( A ) NAME/KEY: Positions coded by nonsense codons are identified as Xaa.

( x i ) SEQUENCE DESCRIPTION: SEQ ID NO: 19:

```
Gln Gly Asp Leu Leu Pro Ala Leu Glu Glu Xaa Xaa Phe Leu Ile
1               5                   10                  15

Glu Asp Cys Xaa His Gln Glu Arg Xaa Val Asn Lys Lys Lys Asp
            20              25                  30

Lys Leu Gln Lys Phe Asn Thr Thr Leu Thr Thr Pro Gly Phe Ile Cys
        35              40                  45

Thr Tyr Ser Thr Ile Xaa Ser Pro Gln Arg Ile Xaa Met Trp Arg Arg
    50              55                  60

Arg Tyr Ser Phe Ala Ser Asp Leu Xaa Leu His Lys Lys Ser Gln Ile
65              70                  75                  80

Lys Lys Lys Phe Gly Ser Phe Glu Lys Leu Asn His Ser Lys Met Ser
                85                  90                  95

Pro Xaa Asp Asn Trp Lys His Leu His Glu Xaa Leu Thr Phe Leu Phe
        100                 105                 110

Gly Pro Ser Ser Ser Leu Leu Gly Lys Leu His His Arg Phe Gln Xaa
            115                 120                 125

Ile Glu Val His Gln Xaa His Val Glu Phe Leu Arg Leu Ile Phe Leu
    130                 135                 140

Met Val Ser His Arg Leu Leu Gln Asn Glu Gln Arg Asp Pro Pro Cys
145                 150                 155                 160

Gln Xaa Xaa Ile Asn Leu Xaa Glu Gln Tyr Leu Leu Pro Arg Glu Ser
                165                 170                 175

Thr Pro Xaa Phe Leu Leu Ile Glu Xaa Asp Glu Ser Glu Ile Ser Gly
        180                 185                 190

Lys Leu Thr Gly Pro Ile Pro Pro Cys Ser Arg Gly Val Arg Leu His
        195                 200                 205

Ala Ala Trp Glu Tyr Xaa Glu Ser Thr Glu His Thr Arg Gly Ala Val
210                 215                 220

Leu Pro Ile Ser Gln Ser Leu Phe Val Leu Asp Xaa Met Leu Arg Phe
225                 230                 235                 240

Gln Met Asp Ile Gln Met Xaa Ser Leu Met Asp Arg Arg Thr Ile Gln
                245                 250                 255

Arg Ile Phe Leu Cys Ser Arg Ser Arg Arg Pro Ser Xaa Met Asn His
            260                 265                 270

Leu Pro Xaa Gln Leu Gln Gln Xaa Ser Leu Val Leu Thr Phe Xaa Leu
        275                 280                 285

Met Tyr Ser Phe Gln Xaa Thr Ile Val Tyr Phe Lys Met Glu Xaa Xaa
    290                 295                 300

Arg Ile Leu Xaa Lys Ile Phe His Phe Thr Gly Asn Xaa Ile Lys Phe
305                 310                 315                 320

Thr Asn Xaa Ile Tyr Xaa Phe Lys Val Asn Leu Phe Cys Thr Xaa Ile
                325                 330                 335

Ser Ser Val Ile Ser Arg Ser Asn Asn Glu Gly Xaa Phe Pro
            340                 345                 350
```

( 2 ) INFORMATION FOR SEQ ID NO:20:

( i ) SEQUENCE CHARACTERISTICS:
    ( A ) LENGTH: 350 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Cryptosporidium parvum ( i x ) FEATURE:
    ( A ) NAME/KEY: Positions coded by nonsense codons are
        identified as Xaa.

( x i ) SEQUENCE DESCRIPTION: SEQ ID NO: 20:

```
Ser Arg Arg Pro Ser Ser Gly Leu Gly Arg Arg Val Met Ile Ser Asn
 1               5                  10                      15

Arg Arg Leu Leu Thr Pro Arg Lys Val Ser Xaa Xaa Glu Lys Lys Arg
                20                  25                  30

Xaa Ile Thr Lys Ile Xaa His Tyr Ile Asn Asn Ser Arg Val Tyr Leu
        35              40                      45

His Leu Phe His Asn Leu Val Ala Thr Glu Asp Leu Asp Val Glu Thr
    50                  55                  60

Thr Ile Leu Ile Cys Ile Xaa Phe Ile Thr Thr Xaa Lys Lys Ser Asp
65                  70                  75                      80

Xaa Lys Lys Ile Trp Phe Ile Xaa Lys Ile Lys Ser Phe Xaa Asn Glu
                85                  90                  95

Ser Leu Arg Xaa Leu Glu Thr Pro Ser Xaa Val Ala Asp Ile Pro Phe
            100                 105                 110

Trp Pro Phe Phe Gln Phe Ala Gly Gln Thr Ser Pro Xaa Val Ser Val
            115                 120                 125

Asn Xaa Ser Ala Ser Ile Thr Arg Arg Val Ser Ser Thr Asp Leu Pro
    130                 135                 140

Asn Gly Lys Ser Xaa Ile Thr Ser Glu Arg Thr Thr Arg Pro Ser Leu
145                 150                 155                 160

Ser Met Met Asn Lys Pro Leu Arg Ala Ile Pro Ser Ser Ser Arg Lys
                165                 170                 175

Tyr Thr Ile Val Leu Ala Asn Xaa Met Arg Xaa Val Arg Asp Lys Trp
            180                 185                 190

Glu Ile Asp Trp Ser Asn Ser Thr Leu Phe Lys Arg Ser Thr Ser Pro
        195                 200                 205

Cys Ser Met Gly Val Leu Arg Ile Asn Xaa Ala His Glu Arg Ser Cys
    210                 215                 220

Thr Pro Asn Phe Ser Lys Ser Phe Cys Ala Xaa Leu Asn Ala Lys Ile
225                 230                 235                 240

Ser Asp Gly His Thr Asn Val Lys Phe Asn Gly Xaa Lys Asn Asn Thr
            245                 250                 255

Thr Tyr Phe Pro Leu Xaa Ser Leu Lys Glu Thr Phe Leu Asn Glu Pro
            260                 265                 270

Ser Ala Ile Thr Ala Ser Ala Val Lys Phe Gly Ala Asn Phe Leu Thr
            275                 280                 285

Asn Val Leu Ile Ser Ile Asp Tyr Cys Ile Leu Xaa Asn Gly Ile Ile
    290                 295                 300

Ala Asn Phe Val Lys Asn Ile Ser Leu Tyr Trp Lys Leu Asn Xaa Ile
305                 310                 315                 320

His Lys Leu Asn Leu Leu Ile Gln Gly Gln Phe Ile Leu Tyr Leu Asn
                325                 330                 335
```

```
Ile Leu Ser Tyr Ile Ser Lys Gln Xaa Xaa Gly Val Ile Pro
            340                 345                 350
```

( 2 ) INFORMATION FOR SEQ ID NO:21:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 21:

```
Thr Leu Asn Gln Xaa Ile Gln Phe Val Asn Leu Ile Xaa Phe Pro Val
                5                  10                  15
Lys Xaa Asn Ile Phe Tyr Lys Ile Gln Tyr Tyr Ser Ile Leu Lys Tyr
            20                  25                  30
Thr Ile Val Tyr Xaa Asn Glu Tyr Ile Ser Xaa Lys Val Ser Thr Lys
        35                  40                  45
Leu Tyr Cys Xaa Ala Val Met Gln Met Val His Ser Glu Val
        50                  55                  60
```

( 2 ) INFORMATION FOR SEQ ID NO:22:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 22:

```
Asp Leu Glu Ser Ile Asn Ser Ile Cys Glu Phe Asn Leu Ile Ser Ser
                5                  10                  15
Lys Val Lys Tyr Phe Leu Gln Asn Ser Val Leu Phe His Phe Lys Val
            20                  25                  30
Tyr Asn Ser Leu Leu Lys Xaa Val His Xaa Leu Glu Ser Xaa His Gln
        35                  40                  45
Thr Leu Leu Leu Ser Cys Tyr Ala Asp Gly Ser Phe Arg Gly
        50                  55                  60
```

( 2 ) INFORMATION FOR SEQ ID NO:23:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:

( A ) ORGANISM: Cryptosporidium parvum ( i x ) FEATURE:
    ( A ) NAME/KEY: Positions coded by nonsense codons are
          identified as Xaa.

( x i ) SEQUENCE DESCRIPTION: SEQ ID NO: 23:

```
Gly Pro Xaa Ile Asn Lys Phe Asn Leu Xaa Ile Xaa Phe Asn Phe Gln
              5                      10                     15

Xaa Ser Glu Ile Phe Phe Thr Lys Phe Ser Ile Ile Pro Phe Xaa Ser
             20                      25                  30

Ile Gln Xaa Ser Ile Glu Met Ser Thr Leu Val Arg Lys Leu Ala Pro
             35              40                  45

Asn Phe Thr Ala Glu Leu Leu Cys Arg Trp Phe Ile Gln Arg Ser
     50              55                       60
```

( 2 ) INFORMATION FOR SEQ ID NO:24:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 24:

```
Arg Pro Leu Asn Glu Pro Ser Ala Xaa Gln Leu Ser Ser Lys Val Trp
 1               5                   10                     15

Cys Xaa Leu Ser Asn Xaa Cys Thr His Phe Asn Arg Leu Leu Tyr Thr
             20                  25                  30

Leu Lys Trp Asn Asn Thr Glu Phe Cys Leu Leu Tyr Phe Thr Leu Leu
             35              40                  45

Glu Ile Lys Leu Asn Ser Gln Ile Glu Phe Ile Asp Ser Arg Ser
     50              55                       60
```

( 2 ) INFORMATION FOR SEQ ID NO:25:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 25:

```
Thr Ser Glu Xaa Thr Ile Cys Ile Thr Ala Gln Gln Xaa Ser Leu Val
 1               5                   10                     15

Leu Thr Phe Xaa Leu Met Tyr Ser Phe Gln Xaa Thr Ile Val Tyr Phe
             20                  25                  30

Lys Met Glu Xaa Tyr Xaa Ile Leu Xaa Lys Ile Phe His Phe Thr Gly
             35              40                  45
```

Asn Xaa Ile Lys Phe Thr Asn Xaa Ile Lys Xaa Phe Lys Val
    50                  55                  60

( 2 ) INFORMATION FOR SEQ ID NO:26:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 26:

Asp Leu Xaa Met Asn His Leu His Asn Ser Ser Ala Val Lys Phe Gly
1               5                   10                  15

Ala Asn Phe Leu Thr Asn Val Leu Ile Ser Ile Asp Tyr Cys Ile Leu
            20                  25                  30

Xaa Asn Gly Ile Ile Leu Asn Phe Val Lys Asn Ile Ser Leu Tyr Trp
        35                  40                  45

Lys Leu Asn Xaa Ile His Lys Leu Asn Leu Leu Ile Gln Gly
    50                  55                  60

( 2 ) INFORMATION FOR SEQ ID NO:27:

( i ) SEQUENCE CHARACTERISTICS:
        ( A ) LENGTH: 1086 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 27:

```
GCGAGTTCCC AGATAGAAGT TTGGATTTCA CAATTCCTCC AGTAGCTGGC CATAACAGCT    60
GTTCAATAAT AGTTGGTGTG AGCGGCGATG GAAAAATTCA CGTAAGCCCA TACGGTTCTA   120
AGGATGTCTC TCTAATAAGT GCTCCAATAC AACCTTCTGA GTTATTCAAT GAAGTTTATT   180
GCGACACTTG TACTGCGAAG TATGGTGCAA TTCACTCTGG ATATCAAACT TCAGCTGATT   240
TCGTAACAAC ACTTCCTACT ACAACTGGAG CCGCAGGACA ACCAACAACT ACTACAACTG   300
GAAGTCCAAG CAAACCAACT ACTACTACCA CTATCTAAGG CAACAACAAC CACAACAACT   360
CTTAATCCAA TCATTACAAC AACAACTCAA AAACCAACAA CAACAACAAC AACAAAGGTT   420
CCAGGTAAGC CACCAATAGC CACAACAACA ACAACATTAA AGCCAATAGT TACAACAACA   480
ACAACAAAAG CAACAACAAC AACAACAACA ACAGTGCCAA CGACAACTAC TACTACCAAG   540
AGAGACGAAA TGACAACAAC AACGACACCA TTACCTGATA TCGGTGACAT TGAAATTACA   600
CCAATCCCAA TTGAAAAGAT GTTGGATAAG TACACAAGAA TGATTTATGA CTATAACAGT   660
GGTTTATTAT TAGACTCTAA TGATGAACCA ATTCCAGGTT CTCAAGCAGG ACAAATAGCT   720
GATACAAGCA ATTTATTCCC AGGTTCAAAC TCACAAGAGT ACTGGTTTAC CAATTGATCC   780
AATGGTTGGT CTTCCATTTG ATCCAAAATC AGGTAATTTA GTACATCCAT ATACCAATCA   840
```

| | | | | | | |
|---|---|---|---|---|---|---|
| AACAATGTCT | GGTTTATCGG | TATCATATCT | TGCTGCTAAG | AATTTGACAG | TTGATACTGA | 900 |
| TGAAACTACG | GTTTACCAAT | TGATACACTC | ACTGGTTACC | CATTGGATCC | AGTCAGTTTG | 960 |
| ATTCCGTTCA | ATCCAGAAAC | TGGTGAATTG | TTTGTCCAAT | ATCAGATGAG | ATAATGAATG | 1020 |
| GAACAATTGC | AGGTATTGTT | TCAGGAATTT | CTGCAAGTGA | GTCATTATTA | TCTCAGAAAT | 1080 |
| CGCTCC | | | | | | 1086 |

( 2 ) INFORMATION FOR SEQ ID NO:28:

( i ) SEQUENCE CHARACTERISTICS:
        ( A ) LENGTH: 1086 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 28:

| | | | | | | |
|---|---|---|---|---|---|---|
| GGAGCGATTT | CTGAGATAAT | AATGACTCAC | TTGCAGAAAT | TCCTGAAACA | ATACCTGCAA | 60 |
| TTGTTCCATT | CATTATCTCA | TCTGATATTG | GACAAACAAT | TCACCAGTTT | CTGGATTGAA | 120 |
| CGGAATCAAA | CTGACTGGAT | CCAATGGGTA | ACCAGTGAGT | GTATCAATTG | GTAAACCGTA | 180 |
| GTTTCATCAG | TATCAACTGT | CAAATTCTTA | GCAGCAAGAT | ATGATACCGA | TAAACCAGAC | 240 |
| ATTGTTTGAT | TGGTATATGG | ATGTACTAAA | TTACCTGATT | TTGGATCAAA | TGGAAGACCA | 300 |
| ACCATTGGAT | CAATTGGTAA | ACCAGTACTC | TTGTGAGTTT | GAACCTGGGA | ATAAATTGCT | 360 |
| TGTATCAGCT | ATTTGTCCTG | CTTGAGAACC | TGGAATTGGT | TCATCATTAG | AGTCTAATAA | 420 |
| TAAACCACTG | TTATAGTCAT | AAATCATTCT | TGTGTACTTA | TCCAACATCT | TTTCAATTGG | 480 |
| GATTGGTGTA | ATTTCAATGT | CACCGATATC | AGGTAATGGT | GTCGTTGTTG | TTGTCATTTC | 540 |
| GTCTCTCTTG | GTAGTAGTAG | TTGTCGTTGG | CACTGTTGTT | GTTGTTGTTG | TTGTTGCTTT | 600 |
| TGTTGTTGTT | GTTGTAACTA | TTGGCTTTAA | TGTTGTTGTT | GTTGTGGCTA | TTGGTGGCTT | 660 |
| ACCTGGAACC | TTTGTTGTTG | TTGTTGTTGT | TGGTTTTGA | GTTGTTGTTG | TAATGATTGG | 720 |
| ATTAAGAGTT | GTTGTGGTTG | TTGTTGCCTT | AGATAGTGGT | AGTAGTAGTT | GGTTTGCTTG | 780 |
| GACTTCCAGT | TGTAGTAGTT | GTTGGTTGTC | CTGCGGCTCC | AGTTGTAGTA | GGAAGTGTTG | 840 |
| TTACGAAATC | AGCTGAAGTT | TGATATCCAG | AGTGAATTGC | ACCATACTTC | GCAGTACAAG | 900 |
| TGTCGCAATA | AACTTCATTG | AATAACTCAG | AAGGTTGTAT | TGGAGCACTT | ATTAGAGAGA | 960 |
| CATCCTTAGA | ACCGTATGGG | CTTACGTGAA | TTTTTCCATC | GCCGCTCACA | CCAACTATTA | 1020 |
| TTGAACAGCT | GTTATGGCCA | GCTACTGGAG | GAATTGTGAA | ATCCAAACTT | CTATCTGGGA | 1080 |
| ACTCGC | | | | | | 1086 |

( 2 ) INFORMATION FOR SEQ ID NO:29:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID

```
AATTCCGGCA ATTAATGCCA AACAATCAGC TCAGATTAGC TAGAGGTGGA AATCTATGTT    60

AACAAGTCCA GGAGATAAGC CAGGAGTCGC GAATGTTGCA TTAAACTCAG CAGCCAGTTC   120

CACAAGTGTG TTAGACAGTA T                                             141
```

( 2 ) INFORMATION FOR SEQ ID NO:30:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 30:

```
ATACTGTCTA ACACACTTGT GGAACTGGCT GCTGAGTTTA ATGCAACATT CGCGACTCCT    60

GGCTTATCTC CTGGACTTGT TAACATAGAT TTCCACCTCT AGCTAATCTG AGCTGATTGT   120

TTGGCATTAA TTGCCGGAAT T                                             141
```

( 2 ) INFORMATION FOR SEQ ID NO:31:

( i ) SEQUENCE CHARACTERISTICS:
        ( A ) LENGTH: 1053 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 31:

```
CCGGGAATTA CCCCTCATTA TTGCTTCGAG ATATAACTGA GGATATTTAG GTACAAAATA    60

AATTGACCTT GAATCAATAA ATTCAATTTG TGAATTTAAT TTAATTTCCA GTAAAGTGAA   120

ATATTTTTA CAAAATTCGC TATTATTCCA TTTTAAAGTA TACAATAGTC TATTGAAATG    180

AGTACATTAG TTAGAAAGTT AGCACCAAAC TTTACTGCTG AAGCTGTTAT GGCAGATGGT   240

TCATTCAAGA AGGTCTCCTT GAGCGACTAC AGAGGAAAAT ACGTTGTATT GTTCTTCTAT   300

CCATTAAACT TCACATTTGT ATGTCCATCT GAAATCTTAG CATTCAATCA AGCACAAAAA   360

GACTTTGAGA AATTGGGAGT ACAGCTCCTC TCGTGTGCTC AGTTGATTCT CAATACTCCC   420

ATGCTGCATG GAGACGTACT CCTCTTGAAC AAGGTGGAAT TGGACCAGTC AATTTCCCAC   480

TTATCTCTGA CTCATCTCAT TCAATTAGCA AGAACTATGG TGTACTTTCT CGAGGAAGAA   540

GGTATTGCTC TCAGAGGTTT ATTCATCATT GACAAGGAGG GTCGCGTTGT TCGTTCTGAA   600

GTAATCTATG ACTTACCATT AGGAAGATCA GTCGAAGAAA CTCTACGTGT TATTGATGCA   660

CTTCAATTCA CTGAAACCTA TGGTGAAGTT TGCCCAGCAA ACTGGAAGAA GGGCCAAAAA   720

GGAATGTCAG CTACTCATGA AGGTGTTTCC AGTTATCTTA AGGACTCATT TTAGAATGAT   780

TTAATTTTTC AAATGAACCA AATTTTTTTT TAATCTGACT TTTTTATGT AGTTATAAAT    840

CAGATGCAAA TGAGTATCGT CGTCTCCACA TCTAGATCCT CTGTGGCGAC TAGATTGTGG   900

AATAGGTGCA AATAAACCCT GGAGTTGTTA ATGTAGTGTT AAATTTTGT AATTTATCTT    960

TTTTTTTCTT ATTAACTTAC CTTTCTTGGT GTTAGCAGTC TTCTATTAGA AATCATTACT  1020

CTTCTTCCAA GGCCGGAAGA AGGTCTCCTT GAG                               1053
```

( 2 ) INFORMATION FOR SEQ ID NO:32:

( i ) SEQUENCE CHARACTERISTICS:
        ( A ) LENGTH: 1053 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 32:

```
CTCAAGGAGA  CCTTCTTCCG  GCCTTGGAAG  AAGAGTAATG  ATTTCTAATA  GAAGACTGCT    60
AACACCAAGA  AAGGTAAGTT  AATAAGAAAA  AAAAGATAA   ATTACAAAAA  TTTAACACTA   120
CATTAACAAC  TCCAGGGTTT  ATTTGCACCT  ATTCCACAAT  CTAGTCGCCA  CAGAGGATCT   180
AGATGTGGAG  ACGACGATAC  TCATTTGCAT  CTGATTTATA  ACTACATAAA  AAAAGTCAGA   240
TTAAAAAAAA  ATTTGGTTCA  TTTGAAAAAT  TAAATCATTC  TAAAATGAGT  CCTTAAGATA   300
ACTGGAAACA  CCTTCATGAG  TAGCTGACAT  TCCTTTTTGG  CCCTTCTTCC  AGTTTGCTGG   360
GCAAACTTCA  CCATAGGTTT  CAGTGAATTG  AAGTGCATCA  ATAACACGTA  GAGTTTCTTC   420
GACTGATCTT  CCTAATGGTA  AGTCATAGAT  TACTTCAGAA  CGAACAACGC  GACCCTCCTT   480
GTCAATGATG  AATAAACCTC  TGAGAGCAAT  ACCTTCTTCC  TCGAGAAAGT  ACACCATAGT   540
TCTTGCTAAT  TGAATGAGAT  GAGTCAGAGA  TAAGTGGGAA  ATTGACTGGT  CCAATTCCAC   600
CTTGTTCAAG  AGGAGTACGT  CTCCATGCAG  CATGGGAGTA  TTGAGAATCA  ACTGAGCACA   660
CGAGAGGAGC  TGTACTCCCA  ATTTCTCAAA  GTCTTTTGT   GCTTGATTGA  ATGCTAAGAT   720
TTCAGATGGA  CATACAAATG  TGAAGTTTAA  TGGATAGAAG  AACAATACAA  CGTATTTTCC   780
TCTGTAGTCG  CTCAAGGAGA  CCTTCTTGAA  TGAACCATCT  GCCATAACAG  CTTCAGCAGT   840
AAAGTTTGGT  GCTAACTTTC  TAACTAATGT  ACTCATTTCA  ATAGACTATT  GTATACTTTA   900
AAATGGAATA  ATAGCGAATT  TTGTAAAAAA  TATTTCACTT  TACTGGAAAT  TAAATTAAAT   960
TCACAAATTG  AATTTATTGA  TTCAAGGTCA  ATTTATTTTG  TACCTAAATA  TCCTCAGTTA  1020
TATCTCGAAG  CAATAATGAG  GGGTAATTCC  CGG                                 1053
```

( 2 ) INFORMATION FOR SEQ ID NO:33:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 33:

```
GGACCTTGAA  TCAATAAATT  CAATTTGTGA  ATTTAATTTA  ATTCCAGTA   AAGTGAAATA    60
TTTTTACAA   AATTCAGTAT  TATTCCATTT  TAAAGTATAC  AATAGTCTAT  TGAAATGAGT   120
ACATTAGTTA  GAAAGTTAGC  ACCAAACTTT  ACTGCTGAGC  TGTTATGCAG  ATGGTTCATT   180
CAGAGGTCT                                                                189
```

( 2 ) INFORMATION FOR SEQ ID NO:34:

( i ) SEQUENCE CHARACTERISTICS:

(A) LENGTH: 189 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Cryptosporidium parvum (xi) SEQUENCE DESCRIPTION: SEQ ID NO: 34:

```
AGACCTCTGA ATGAACCATC TGCATAACAG CTCAGCAGTA AAGTTTGGTG CTAACTTTCT      60
AACTAATGTA CTCATTTCAA TAGACTATTG TATACTTTAA AATGGAATAA TACTGAATTT     120
TGTAAAAAAT ATTTCACTTT ACTGGAAATT AAATTAAATT CACAAATTGA ATTTATTGAT     180
TCAAGGTCC                                                             189
```

(2) INFORMATION FOR SEQ ID NO:35:

(i) SEQUENCE CHARACTERISTICS:
(A) LENGTH: 362 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: Cryptosporidium parvum (ix) FEATURE:
(A) NAME/KEY: Positions coded by nonsense codons are identified as Xaa.

(xi) SEQUENCE DESCRIPTION: SEQ ID NO: 35:

```
Arg Thr Gly Leu Tyr Phe Asn Pro Asn Xaa Leu Glu Glu Leu Leu Gln Gly Tyr
                5                   10                  15
Cys Ser Asn Leu Leu Leu Gln His Ser Arg Arg His Phe Phe Glu Arg Leu Gly
        20                  25                  30                  35
Met Arg Asn Xaa Pro His Arg Glu Leu Leu His Glu Leu Val Val Lys Gln Thr
            40                  45                  50
Ile Xaa His Leu Lys Asn Arg Cys Lys Tyr Gln Ser Thr His His Leu Glu Ser
55                  60                  65                  70
Gln Ile Asp Phe Lys Leu Gln Asn Arg Leu Leu Val Glu Xaa Xaa Leu Gln Leu
        75                  80                  85                  90
Arg Leu Val Val Leu Leu Xaa Xaa Leu Gln Phe Asp Leu Cys Val Leu Xaa Xaa
                95                  100                 105
Xaa Trp Xaa Arg Leu Cys Cys Cys Gly Cys Cys Ser Lys Ile Trp Asp Asn Cys
    110                 115                 120                 125
Cys Cys Ser Leu Phe Trp Cys Cys Cys Cys Cys Leu Asn Trp Thr Leu Trp
            130                 135                 140
Trp Tyr Gly Cys Cys Cys Cys Cys Xaa Leu Trp Tyr Asn Cys Cys Cys Cys Cys
145                 150                 155                 160
Phe Cys Cys Cys Cys Cys Cys Cys Cys His Trp Arg Cys Ser Ser Ser Gly Leu
        165                 170                 175                 180
Ser Val Phe His Cys Cys Cys Arg Cys Trp Xaa Arg Ile Asp Thr Val Asn Phe
                185                 190                 195
Asn Cys Trp Asp Trp Asn Phe Leu His Gln Ile Leu Val Cys Ser His Asn Ile
    200                 205                 210                 215
Val Ile Val Thr Thr Xaa Xaa Xaa Val Arg Ile Ile Phe Trp Asn Trp Thr Arg
            220                 225                 230
Leu Cys Ser Leu Tyr Ser Ile Cys Ala Ile Xaa Glu Trp Thr Xaa Val Xaa Leu
```

|   235 | | | | | | | 240 | | | | | | | 245 | | | | | | | 250 | |
|---|---|---|---|---|---|---|---|---|---|---|---|---|---|---|---|---|---|---|---|---|---|---|

Leu Val Pro Lys Gly Ile Ser Gly Ile Thr Pro Arg Gly Asn Ser Gly Phe Asp
        255                     260                 265                 270

Pro Leu Lys Thr Cys Gly Tyr Val Leu Xaa Val Ile Asp Pro Lys Asp Thr Asp
            275                 280             285

Tyr Arg Ala Ala Leu Phe Lys Val Thr Ser Val Ser Ser Val Val Thr Xaa Trp
    290                 295                 300                 305

Asn Ile Cys Glu Ser Thr Val Trp Gln Ile Trp Asp Thr Gln Asn Arg Glu Ile
            310                 315                 320

Trp Phe Ser Thr Phe Gln Lys Asp Leu Ile Leu His Ser Leu Ser His Phe Leu
325                     330                 335                 340

Gln Leu Tyr Gln Lys Leu Phe Lys Gln Leu His Thr Met Ile Ile Glu Ser Ile
        345                     350                 355                 360

Ala Gly ( 2 ) INFORMATION FOR SEQ ID NO:36:

( i ) SEQUENCE CHARACTERISTICS:
        ( A ) LENGTH: 361 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
        identified as Xaa.

( x i ) SEQUENCE DESCRIPTION: SEQ ID NO: 36:

Ser Asn Gly Ser Leu Leu Lys Ser Lys Val Ile Gly Gly Thr Ala Pro Trp Leu
1               5                   10                  15

Leu Gln Glu Ile Ile Thr Pro Thr Leu Pro Ser Pro Phe Ile Xaa Thr Leu Gly
    20              25                  30                  35

Tyr Pro Glu Leu Ser Thr Glu Arg Ile Leu Ala Gly Ile Cys Gly Glu Ser Asn
        40                  45                  50

Asn Leu Ser Thr Xaa Gln Ser Val Gln Val Ala Phe Tyr Pro Ala Ile Xaa Glu
55              60                  65                  70

Pro Tyr Xaa Val Glu Ala Ser Lys Thr Val Val Ser Gly Val Val Val Pro Ala
        75              80                  85                  90

Ala Pro Cys Gly Val Val Val Val Val Pro Leu Gly Leu Leu Gly Val Val Val
            95                  100                 105

Val Val Ile Xaa Pro Leu Leu Leu Trp Leu Leu Glu Xaa Asp Leu Xaa Xaa Leu
    110                 115                 120                 125

Leu Leu Glu Phe Val Leu Leu Leu Leu Leu Leu Pro Glu Leu Tyr Ala Val
            130                 135                 140

Leu Leu Trp Leu Leu Leu Leu Met Leu Ala Leu Leu Xaa Leu Leu Leu Leu Leu
145                 150                 155                 160

Leu Leu Leu Leu Leu Leu Leu Leu Leu Ala Leu Ser Leu Xaa Xaa Xaa Trp Ser
            165                 170                 175                 180

Leu Arg Phe Ser Leu Leu Leu Ser Val Met Val Gln Tyr Arg His Cys Gln Phe
            185                 190                 195

Xaa Val Leu Gly Leu Gln Phe Ser Thr Pro Tyr Thr Cys Leu Phe Ser Lys His
    200                 205                 210                 215

Ser Tyr Cys His Asn Ile Ile Leu Ser Xaa His His Val Leu Glu Leu Asn Glu
            220                 225                 230

| | | | | | | | | | | | | | | | |
|---|---|---|---|---|---|---|---|---|---|---|---|---|---|---|---|
| Leu<br>235 | Leu | Val | Phe | Leu | Gln<br>240 | Tyr | Leu | Cys | Asn | Ile<br>245 | Gly | Leu | Asn | Leu<br>250 | Ser | Val | Leu |
| Thr | Ser | Thr<br>255 | Xaa | Trp | Asn | Ile | Trp<br>260 | His | Asn | Thr | Lys | Trp<br>265 | Lys | Ile | Trp | Phe | Xaa<br>270 |
| Thr | Ile | Xaa | Tyr | Met<br>275 | Trp | Ile | Gly | Ile | Leu<br>280 | Cys | His | Arg | Thr | Xaa<br>285 | Arg | Tyr | Xaa |
| Ile | Lys<br>290 | Ser | Ser | Leu | Ile | Gln<br>295 | Cys | Asn | Ile | Ser | Ile<br>300 | Phe | Ser | Arg | Asn<br>305 | Val | Leu |
| Gln | Tyr | Val | Xaa<br>310 | Gln | Asn | Gly | Met | Pro<br>315 | Asp | Leu | Xaa | Asn | Ser<br>320 | Glu | Thr | Xaa | Asp |
| Leu<br>325 | Phe | Gln | His | Ile | Thr<br>330 | Gln | Gly | Ile | Asp | Ser<br>335 | Ser | Ile | Ile | Phe | Pro<br>340 | Val | Ile |
| Ala | Pro | Ile<br>345 | Thr | Glu | Pro | Ile | Glu<br>350 | Ala | Leu | Ser | Asp | Asn<br>355 | Asn | Asp | Xaa | Phe | Asp<br>360 |
| Ser | | | | | | | | | | | | | | | | | |

(2) INFORMATION FOR SEQ ID NO:37:

(i) SEQUENCE CHARACTERISTICS:
        (A) LENGTH: 361 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cryptosporidium parvum (ix) FEATURE:
        (A) NAME/KEY: Positions coded by nonsense codons are identified as Xaa.

(xi) SEQUENCE DESCRIPTION: SEQ ID NO: 37:

| | | | | | | | | | | | | | | | |
|---|---|---|---|---|---|---|---|---|---|---|---|---|---|---|---|
| Leu<br>1 | Glu | Trp | Ile | Ser<br>5 | Thr | Gln | Ile | Glu | Cys<br>10 | Asn | Arg | Trp | Tyr | Ser<br>15 | Ala | Met | Val |
| Ala | Thr<br>20 | Xaa | Tyr | Tyr | Asn | Thr<br>25 | His | Ala | Ala | Ile | Ser<br>30 | Phe | Asn | Val | Tyr<br>35 | Ala | Trp |
| Val | Thr | Arg | Leu<br>40 | Ile | Asp | Arg | Xaa | Tyr<br>45 | Thr | Ser | Trp | Tyr | Leu<br>50 | Arg | Arg | Leu | Xaa |
| Glu<br>55 | Ile | Phe | Asn | Ile | Ala<br>60 | Val | Ser | Thr | Ser | Arg<br>65 | Leu | Ile | Thr | Cys<br>70 | Asn | Val | Arg |
| Ser | Ile | Leu<br>75 | Ser | Xaa | Ser | Ile | Glu<br>80 | Tyr | Cys | Cys | Lys | Arg<br>85 | Ser | Cys | Ser | Ser | Gly<br>90 |
| Cys | Ser | Leu | Trp | Cys<br>95 | Ser | Ser | Cys | Ser | Ser<br>100 | Thr | Trp | Ala | Phe | Trp<br>105 | Ser | Ser | Ser |
| Gly | Ser<br>110 | Asp | Leu | Ala | Val | Val<br>115 | Val | Val | Val | Val | Arg<br>120 | Leu | Gly | Ile | Met<br>125 | Val | Val |
| Val | Val | Xaa<br>130 | Phe | Gly | Val | Val | Val<br>135 | Val | Val | Val | Phe | Thr<br>140 | Gly | Pro | Leu | Gly | Gly |
| Ile<br>145 | Ala | Val | Val | Val | Val<br>150 | Val | Asn | Phe | Gly | Ile<br>155 | Thr | Val | Val | Val<br>160 | Val | Val | Phe |
| Ala | Val | Val<br>165 | Val | Val | Val | Val<br>170 | Thr | Gly | Val | Val | Val<br>175 | Val | Val | Val | Leu<br>180 | Leu |
| Ser | Ser | Ile | Val | Val<br>185 | Val | Val | Val | Gly | Asn<br>190 | Gly | Ser | Ile | Pro | Ser<br>195 | Met | Ser | Ile |
| Val | Gly<br>200 | Ile | Gly | Ile | Ser | Phe<br>205 | Ile | Asn | Ser | Leu | Tyr<br>210 | Val | Leu | Ile | Ile<br>215 | Xaa | Ser |

| | | | | | | | | | | | | | | | |
|---|---|---|---|---|---|---|---|---|---|---|---|---|---|---|---|
|Xaa|Leu|Leu|Pro<br>220|Lys|Asn|Asn|Ser|Glu<br>225|Leu|Ser|Ser|Gly|Ile<br>230|Pro|Glu Xaa|
|Ala<br>235|Pro|Cys|Ile|Ala|Ser<br>240|Val|Leu|Leu|Lys|Asn<br>245|Gly|Pro|Glu|Phe<br>250|Glu Cys Ser|
|Tyr|Gln|Asn<br>255|Val|Leu|Gln|Asp|Leu<br>260|Pro|Gln|Asp|Glu|Met<br>265|Gln|Asp|Leu Ile Leu<br>270|
|Tyr|Asn|Leu|Val|Asp<br>275|Met|Tyr|Trp|Asp|Phe<br>280|Leu|Thr|Gln|Asn|Ile<br>285|Pro Ile Met|
|Asp|Gln<br>290|Gln|Xaa|Ser|Asn|Ser<br>295|Leu|Gln|Tyr|Gln|His<br>300|Phe|Xaa|Pro|Lys Gly Ile<br>305|
|Ser|Val|Ser|Val|Pro<br>310|Xaa|Gly|Asn|Ser|Gly<br>315|Thr|Leu|Lys|Ile<br>320|Gly|Asn Leu Gly|
|Ser<br>325|Val|Pro|Ser|Asn|Asn<br>330|Thr|Trp|Tyr|Xaa|Ile<br>335|Leu|Tyr|His|Ile<br>340|Ser Cys Asn|
|Cys|Thr|Asn<br>345|Asn|Xaa|Ser|Asn|Arg<br>350|Cys|Thr|Leu|Xaa|Xaa<br>355|Xaa|Arg|Leu Phe Arg<br>360|
|Glu| | | | | | | | | | | | | | | |

( 2 ) INFORMATION FOR SEQ ID NO:38:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 38:

| | | | | | | | | | | | | | | | |
|---|---|---|---|---|---|---|---|---|---|---|---|---|---|---|---|
|Ile<br>1|Gly|Ala|Ile|Leu<br>5|Ala|Leu|Cys|Asp|Ala<br>10|Xaa|Ile|Leu|Xaa|Leu<br>15|His Phe Asp|
|Ile|Asn<br>20|Val|Leu|Gly|Pro|Ser<br>25|Leu|Gly|Pro|Thr|Ala<br>30|Phe|Thr|Ala|Asn Phe Glu<br>35|
|Ala|Ala|Leu|Glu<br>40|Val|Leu|Thr|Asn|Ser<br>45|Leu|Ile| | | | | |

( 2 ) INFORMATION FOR SEQ ID NO:39:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 39:

| | | | | | | | | | | | | | | | |
|---|---|---|---|---|---|---|---|---|---|---|---|---|---|---|---|
|Asn<br>1|Arg|Cys|Asn|Ile<br>5|Gly|Phe|Leu|Xaa|Ser<br>10|Leu|Asn|Ala|Leu|Pro<br>15|Pro Phe Arg|
|His|Xaa<br>20|Cys|Thr|Trp|Ser|Ile<br>25|Leu|Trp|Ser|Asp|Arg<br>30|Ile|Asn|Cys|Xaa Val Xaa<br>35|

```
Cys  Gly  Thr  Gly  Cys  Thr  His  Xaa  Val  Thr
               40                      45
```

( 2 ) INFORMATION FOR SEQ ID NO:40:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 40:

```
Glu  Pro  Leu  Xaa  His  Trp  Val  Ile  Leu  Glu  Ser  Xaa  Ser  Ser  Thr  Ser  Ile  Xaa
1                    5                      10                      15

Thr  Leu  Leu  Asp  Leu  Leu  Tyr  Ala  Leu  Leu  Arg  Ser  His  Gln  Met  Leu  Ser  Leu
     20                      25                      30                           35

Leu  Trp  Asn  Trp  Leu  His  Thr  Leu  Cys  Tyr
               40                      45
```

( 2 ) INFORMATION FOR SEQ ID NO:41:

( i ) SEQUENCE CHARACTERISTICS:
        ( A ) LENGTH: 351 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 41:

```
Arg  Ser  Asn  Gly  Arg  Met  Ile  Ala  Glu  Leu  Tyr  Leu  Gln  Pro  Tyr  Lys  Pro  Val
1                    5                      10                      15

Phe  Tyr  Ile  Ser  Arg  Ser  Asp  Ile  Phe  Glu  Ile  Gln  Ser  Asn  Leu  Lys  Ile  Glu
     20                      25                      30                           35

Leu  Leu  Thr  Phe  Tyr  Lys  Lys  Cys  Phe  Glu  Ser  Asn  Asn  Trp  Lys  Leu  Thr  Tyr
               40                      45                      50

Leu  Leu  Arg  Asn  Phe  His  Thr  Cys  Xaa  Asn  Ser  Leu  Xaa  Cys  Trp  Val  Lys  Ser
55                        60                      65                      70

Ser  Phe  Ser  Asn  His  Cys  Ile  Thr  Xaa  Glu  Leu  Leu  Asp  Gly  Gln  Ala  Val  Val
          75                        80                      85                           90

Ser  Ser  Phe  Val  Asn  Tyr  Gln  Glu  Glu  Ile  Trp  Xaa  Val  Glu  Cys  Lys  Tyr  Thr
               95                      100                     105

Trp  Arg  Phe  Asp  Xaa  Cys  Glu  Ile  Leu  Cys  Leu  Phe  Val  Lys  Leu  Phe  Gln  Ser
     110                     115                          120                     125

Tyr  Leu  Glu  Glu  Arg  Thr  Ser  Leu  Gln  Asn  Glu  Ile  Ser  Gly  His  Gln  Met  Ser
               130                     135                     140

Val  Tyr  Glu  Glu  Gln  Val  Leu  His  Phe  Gln  Val  Leu  Xaa  Asn  Gly  Val  Xaa  Arg
145                     150                     155                     160
```

```
Gln  Ser  Met  Glu  Asn  Leu  Xaa  Cys  Ser  Ser  His  His  Val  Lys  Glu  Leu  Phe  Phe
          165                 170                     175                          180

Thr  Asn  Ser  Glu  Ser  Thr  Xaa  Glu  Asp  Asn  Val  Leu  Leu  Thr  Ala  Asn  Asn  Thr
                    185                 190                          195

Arg  Phe  Tyr  Asp  Ile  Val  Xaa  Trp  Xaa  Ser  Ser  Xaa  Asp  Phe  Phe  Ser  Xaa  Thr
          200                 205                     210                          215

Asn  Asn  Ile  Cys  Lys  Leu  Glu  Ser  Phe  Gly  Ile  Thr  Phe  Asn  Ala  Trp  Cys  Val
               220                      225                     230

Pro  Leu  Leu  Ala  Leu  Phe  Ser  His  Xaa  Ser  Ser  Met  Phe  Thr  Asn  Gly  Thr  Ile
235                      240                 245                          250

Lys  Leu  Val  Xaa  Lys  Leu  Ile  Ile  Xaa  Asn  Lys  Leu  His  Val  Leu  Asn  Lys  Lys
               255                 260                     265                          270

Leu  Arg  Val  Lys  Lys  Ile  Tyr  Asn  Tyr  Ile  Leu  His  Leu  His  Thr  Asp  Asp  Asp
                    275                      280                     285

Gly  Cys  Arg  Ser  Gly  Arg  His  Arg  Ser  Ser  Gln  Pro  Ile  Pro  Ala  Phe  Leu  Gly
          290                      295                     300                          305

Gln  Leu  Gln  Xaa  His  Leu  Thr  Leu  Asn  Lys  Tyr  Asn  Ile  Lys  Lys  Lys  Arg  Ile
               310                      315                     320

Leu  Lys  Gly  Lys  Lys  Thr  Asn  Ala  Thr  Lys  Xaa  Xaa  Phe  Asp  Asn  Ser  Lys  Lys
325                      330                      335                          340

Trp  Pro  Arg  Phe  Phe  Thr  Glu  Lys  Leu
          345                 350
```

( 2 ) INFORMATION FOR SEQ ID NO:42:

( i ) SEQUENCE CHARACTERISTICS:
        ( A ) LENGTH: 350 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 42:

```
Pro  Phe  Xaa  Gly  Glu  Asn  Asn  Ser  Arg  Ser  Ile  Val  Ser  Ser  Ile  Xaa  Thr  Cys
1                   5                      10                     15

Phe  Leu  Asn  Val  Lys  Phe  Xaa  Tyr  Ile  Xaa  Asn  Thr  Phe  Lys  Ile  Xaa  Asn  Gly
     20                      25                     30                          35

Thr  Phe  His  Phe  Ile  Lys  Xaa  Leu  Ile  Arg  Xaa  Xaa  Glu  Met  Lys  Phe  Tyr  Val
               40                      45                     50

Ile  Thr  Xaa  Gln  Phe  Ser  Tyr  Met  Leu  Xaa  Phe  Thr  Leu  Val  Leu  Ser  Xaa  Gln
55                       60                      65                          70

Gln  Leu  Gln  Xaa  Pro  Leu  His  Asn  Met  Xaa  Ser  Pro  Arg  Arg  Ser  Arg  Ser  Cys
               75                      80                     85                          90

Leu  Phe  Ile  Arg  Gln  Ile  Thr  Arg  Arg  Asp  Met  Leu  Ser  Xaa  Met  Gln  Ile  Asp
               95                      100                    105

Met  Gln  Phe  Arg  Leu  Met  Xaa  Asp  Leu  Val  Phe  Leu  Ser  Gln  Ser  Ile  Pro  Leu
     110                     115                    120                          125

Val  Ala  Gly  Arg  Thr  His  Glu  Thr  Ser  Glu  Xaa  Tyr  Glu  Trp  Ala  Ala  His  Leu
               130                     135                    140

Arg  Val  Gly  Arg  Ser  Cys  Pro  Pro  Ile  Pro  Gly  Thr  Leu  Lys  Gly  Ser  Ile  Glu
145                      150                     155                          160
```

| Ser | Glu | Asp | Xaa | Glu | Ile | Leu | Leu | Phe | Xaa | Pro | Thr | Ser | Glu | Arg | Pro | Leu | Leu |
| | | 165 | | | | 170 | | | | | | 175 | | | | | 180 |

| Tyr | Gln | Glu | Xaa | Leu | Asn | Ile | Xaa | Xaa | Gln | Cys | Pro | Pro | Asp | Arg | Gln | Glu | Asn |
| | | | | 185 | | | | | 190 | | | | | 195 | | | |

| Gln | Leu | Leu | Arg | His | Ser | Val | Met | Leu | Phe | Ile | Leu | Arg | Leu | Phe | Glu | Val | His |
| | 200 | | | | | 205 | | | | 210 | | | | | | 215 | |

| Xaa | Gln | His | Val | Glu | Ile | Xaa | Gln | Phe | Arg | His | His | Leu | Lys | Gly | Leu | Leu | Ser |
| | | | 220 | | | | | 225 | | | | | 230 | | | | |

| Ser | Ser | Pro | Gly | Phe | Leu | Phe | Thr | Leu | Xaa | Glu | His | Leu | His | Lys | Trp | Asn | Asp |
| 235 | | | | | 240 | | | | | 245 | | | | | 250 | | |

| Xaa | Pro | Ser | Met | Lys | Ser | His | Asn | Leu | Lys | Glu | Phe | Ser | Gly | Phe | Lys | Lys | Lys |
| | | 255 | | | | | 260 | | | | | 265 | | | | | 270 |

| Ile | Gln | Ser | Lys | Lys | His | Leu | Xaa | Leu | Asp | Ser | Ala | Phe | Ser | Tyr | Arg | Arg | Arg |
| | | | | 275 | | | | | 280 | | | | | 285 | | | |

| Trp | Met | Xaa | Ile | Arg | Gln | Pro | Ser | Xaa | Ile | Thr | Ser | Tyr | Thr | Cys | Ile | Phe | Gly |
| | 290 | | | | | 295 | | | | | 300 | | | | | 305 | |

| Pro | Thr | Thr | Leu | Thr | Thr | Asn | Phe | Lys | Gln | Leu | Lys | Asp | Lys | Lys | Lys | Asn | |
| | | | 310 | | | | | 315 | | | | 320 | | | | | |

| Val | Xaa | Arg | Glu | Gln | His | Xaa | Cys | Asp | Glu | Ile | Leu | Phe | Xaa | Xaa | Glu | Glu | Glu |
| 325 | | | | | 330 | | | | | 335 | | | | | 340 | | |

| Leu | Ala | Pro | Leu | Leu | Asp | Gly | Gln | | | | | | | | | | |
| | | 345 | | | | | 350 | | | | | | | | | | |

( 2 ) INFORMATION FOR SEQ ID NO:43:

( i ) SEQUENCE CHARACTERISTICS:
        ( A ) LENGTH: 350 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
        identified as Xaa.

( x i ) SEQUENCE DESCRIPTION: SEQ ID NO: 43:

| Pro | Ile | Val | Gly | Xaa | Xaa | Gln | Lys | Ser | Ile | Tyr | Ser | Leu | Ile | Asn | Leu | Tyr | Leu |
| 1 | | | | 5 | | | | | 10 | | | | | 15 | | | |

| Ile | Phe | Gln | Gly | Gln | Ile | Leu | Leu | Asn | Leu | Lys | His | Ile | Xaa | Asn | Leu | Lys | Trp |
| | 20 | | | | | 25 | | | | | 30 | | | | | 35 | |

| Tyr | Leu | Ser | Ile | Asn | Lys | Val | Phe | Asn | Ala | Ile | Ile | Gly | Asn | Xaa | Leu | Ile | Cys |
| | | | 40 | | | | | 45 | | | | | 50 | | | | |

| Tyr | Asp | Ile | Ser | Ile | Leu | Val | Asn | Thr | Leu | Phe | Asn | Ala | Gly | Phe | Lys | Val | Ala |
| 55 | | | | | 60 | | | | | 65 | | | | | 70 | | |

| Ser | Ala | Thr | Ile | Ala | Ser | Pro | Glu | Asn | Leu | Phe | Thr | Glu | Lys | Leu | Ser | Xaa | Leu |
| | | 75 | | | | | 80 | | | | | 85 | | | | | 90 |

| Pro | Phe | Tyr | Thr | Thr | Asn | Asn | Lys | Xaa | Gly | Asn | Phe | Lys | Val | Asn | Thr | His | Gly |
| | | | | 95 | | | | | 100 | | | | | 105 | | | |

| Asp | Ser | Ile | Lys | Ala | Asn | Leu | Xaa | Ala | Cys | Phe | Ser | Lys | Ser | Phe | Asn | Pro | Thr |
| | 110 | | | | | 115 | | | | | 120 | | | | | 125 | |

| Cys | Ser | Arg | Glu | His | Ala | Xaa | Asn | Ile | Arg | Leu | Val | Gly | Met | Ser | Cys | Pro | Ser |
| | | | 130 | | | | | 135 | | | | | 140 | | | | |

| Thr | Ser | Arg | Lys | Phe | Leu | Thr | Ser | Asn | Ser | Trp | Asp | Ile | Glu | Trp | Lys | Asp | Arg |
| 145 | | | | | 150 | | | | | 155 | | | | | 160 | | |

```
Val  Xaa  Arg  Met  Xaa  Asn  Ala  Leu  Val  Ile  Thr  Tyr  Lys  Arg  Ser  Ser  Ser  Pro
     165            170                           175                           180

Ile  Ala  Arg  Leu  Pro  Lys  Asn  Met  Met  Ser  Leu  Ser  Pro  Arg  Thr  Thr  Arg  Glu
               185                      190                      195

Ser  Thr  Ile  Xaa  Ser  Lys  Gly  Asn  Pro  Leu  Asp  Thr  Ser  Ser  Val  Arg  Arg  Thr
     200                 205                      210                           215

Ile  Ser  Ala  Ser  Xaa  Asn  Val  Ser  Val  Xaa  Pro  Ser  Thr  Gln  Gly  Ala  Phe  Gln
               220                      225                      230

Phe  Phe  Pro  Trp  Phe  Pro  Ile  Asp  Ala  Val  Xaa  Ser  Pro  Thr  Glu  Leu  Xaa  Arg
235            240                           245                      250

Leu  Ser  Glu  Asn  Xaa  Phe  Ser  Lys  Ile  Lys  Xaa  Ile  Phe  Trp  Ile  Lys  Lys  Xaa
          255                 260                      265                           270

Asp  Ser  Lys  Lys  Xaa  Thr  Thr  Ile  Phe  Xaa  Ile  Cys  Ile  Leu  Ile  Thr  Thr  Glu
                    275                 280                           285

Val  Asp  Leu  Asp  Glu  Thr  Ala  Val  Leu  Asn  His  Phe  Leu  His  Leu  Tyr  Val  Arg
     290                 295                      300                      305

Ser  Asn  Asn  Ile  Tyr  His  Xaa  Ile  Lys  Thr  Ile  Xaa  Arg  Lys  Lys  Glu  Xaa  Xaa
               310                      315                 320

Ser  Val  Lys  Arg  Pro  Thr  Leu  Leu  Arg  Arg  Asn  Ser  Ile  Met  Val  Arg  Arg  Gly
325                 330                           335                      340

Leu  Gly  Ser  Ser  Pro  Arg  Arg  Ser
               345                 350
```

( 2 ) INFORMATION FOR SEQ ID NO:44:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:
        ( A ) NAME/KEY: Positions coded by nonsense codons are
            identified as Xaa.

( x i ) SEQUENCE DESCRIPTION: SEQ ID NO: 44:

```
Ser  Arg  Ser  Asp  Ile  Phe  Glu  Ile  Gln  Ser  Asn  Leu  Lys  Ile  Glu  Leu  Leu  Thr
1                   5                      10                      15

Phe  Tyr  Lys  Lys  Cys  Phe  Glu  Thr  Asn  Asn  Trp  Lys  Leu  Thr  Tyr  Leu  Leu  Arg
     20                 25                      30                           35

Asn  Phe  His  Thr  Cys  Xaa  Asn  Ser  Leu  Xaa  Cys  Trp  Val  Lys  Ser  Ser  Leu  Gln
               40                      45                      50

Xaa  Ala  Ser  Pro  Glu  Asn  Leu  Pro  Arg
55                  60
```

( 2 ) INFORMATION FOR SEQ ID NO:45:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Cryptosporidium parvum ( i x ) FEATURE:

(A) NAME/KEY: Positions coded by nonsense codons are
identified as Xaa.

(xi) SEQUENCE DESCRIPTION: SEQ ID NO: 45:

| Val | Lys | Phe | Xaa | Tyr | Ile | Xaa | Asn | Thr | Phe | Lys | Ile | Xaa | Asn | Gly | Thr | Phe | His |
|-----|-----|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |     |     |
| Phe | Ile | Lys | Lys | Cys | Phe | Glu | Thr | Asn | Asn | Trp | Lys | Leu | Thr | Tyr | Leu | Leu | Arg |
|     | 20  |     |     |     |     | 25  |     |     |     |     | 30  |     |     |     |     | 35  |     |
| Asn | Phe | His | Thr | Met | Leu | Xaa | Phe | Thr | Leu | Val | Leu | Ser | Xaa | Gln | Gln | Ala | Thr |
|     |     |     | 40  |     |     |     |     | 45  |     |     |     |     | 50  |     |     |     |     |
| Ile | Cys | Ile | Thr | Xaa | Glu | Ser | Thr |
|-----|-----|-----|-----|-----|-----|-----|-----|
| 55  |     |     |     | 60  |     |     |     |

(2) INFORMATION FOR SEQ ID NO:46:

(i) SEQUENCE CHARACTERISTICS:
  (A) LENGTH: 62 amino acids
  (B) TYPE: amino acid
  (C) STRANDEDNESS: single
  (D) TOPOLOGY: linear (ii) MOLECULE TYPE: peptide (vi) ORIGINAL SOURCE:
  (A) ORGANISM: Cryptosporidium parvum (ix) FEATURE:
  (A) NAME/KEY: Positions coded by nonsense codons are
  identified as Xaa.

(xi) SEQUENCE DESCRIPTION: SEQ ID NO: 46:

| Gly | Gln | Ile | Leu | Leu | Asn | Leu | Lys | His | Ile | Xaa | Asn | Leu | Lys | Trp | Tyr | Leu | Ser |
|-----|-----|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |     |     |
| Ile | Asn | Lys | Val | Phe | Asn | Leu | Ile | Ile | Gly | Asn | Xaa | Leu | Ile | Cys | Tyr | Asp | Ile |
|     | 20  |     |     |     |     | 25  |     |     |     |     | 30  |     |     |     |     | 35  |     |
| Ser | Ile | Leu | Val | Asn | Thr | Leu | Phe | Asn | Ala | Gly | Phe | Lys | Val | Ala | Ser | Ser | Asn |
|     |     |     | 40  |     |     |     |     | 45  |     |     |     |     | 50  |     |     |     |     |
| His | Leu | His | Asn | Met | Xaa | Leu | Asp |
|-----|-----|-----|-----|-----|-----|-----|-----|
| 55  |     |     |     |     | 60  |     |     |

(2) INFORMATION FOR SEQ ID NO:47:

(i) SEQUENCE CHARACTERISTICS:
  (A) LENGTH: 1086 base pairs
  (B) TYPE: nucleic acid
  (C) STRANDEDNESS: double
  (D) TOPOLOGY: linear (ii) MOLECULE TYPE: DNA (genomic)

(vi) ORIGINAL SOURCE:
  (A) ORGANISM: Cryptosporidium parvum (xi) SEQUENCE DESCRIPTION: SEQ ID NO: 47:

| CGC | TCA | AGG | GTC | TAT | CTT | CAA | ACC | TAA | AGT | GTT | AAG | GAG | GTC | ATC | GAC | 48  |
| CGG | TAT | TGT | CGA | CAA | GTT | ATT | ATC | AAC | CAC | ACT | CGC | CGC | TAC | CTT | TTT | 96  |
| AAG | TGC | ATT | CGG | GTA | TGC | CAA | GAT | TCC | TAC | AGA | GAG | ATT | ATT | CAC | GAG | 144 |
| GTT | ATG | TTG | GAA | GAC | TCA | ATA | AGT | TAC | TTC | AAA | TAA | CGC | TGT | GAA | CAT | 192 |
| GAC | GCT | TCA | TAC | CAC | GTT | AAG | TGA | GAC | CTA | TAG | TTT | GAA | GTC | GAC | TAA | 240 |
| AGC | ATT | GTT | GTG | AAG | GAT | GAT | GTT | GAC | CTC | GGC | GTC | CTG | TTG | GTT | GTT | 288 |
| GAT | GAT | GTT | GAC | CTT | CAG | GTT | CGT | TTG | GTT | GAT | GAT | GAT | GGT | GAT | AGA | 336 |
| TTC | CGT | TGT | TGT | TGG | TGT | TGT | TGA | GAA | TTA | GGT | TAG | TAA | TGT | TGT | TGT | 384 |

```
TGA GTT TTT GGT TGT TGT TGT TGT TGT TGT TTC CAA GGT CCA TTC GGT     432
GGT TAT CGG TGT TGT TGT TGT TGT AAT TTC GGT TAT CAA TGT TGT TGT     480
TGT TGT TTT CGT TGT TGT TGT TGT TGT TGT CAC GGT TGC TGT TGA         528
TGA TGA TGG TTC TCT CTG CTT TAC TGT TGT TGT TGC TGT GGT AAT GGA     576
CTA TAG CCA CTG TAA CTT TAA TGT GGT TAG GGT TAA CTT TTC TAC AAC     624
CTA TTC ATG TGT TCT TAC TAA ATA CTG ATA TTG TCA CCA AAT AAT AAT     672
CTG AGA TTA CTA CTT GGT TAA GGT CCA AGA GTT CGT CCT GTT TAT CGA     720
CTA TGT TCG TTA AAT AAG GGT CCA AGT TTG AGT GTT CTC ATG ACC AAA     768
TGG TTA ACT AGG TTA CCA ACC AGA AGG TAA ACT AGG TTT TAG TCC ATT     816
AAA TCA TGT AGG TAT ATG GTT AGT TTG TTA CAG ACC AAA TAG CCA TAG     864
TAT AGA ACG ACG ATT CTT AAA CTG TCA ACT ATG ACT ACT TTG ATG CCA     912
AAT GGT TAA CTA TGT GAG TGA CCA ATG GGT AAC CTA GGT CAG TCA AAC     960
TAA GGC AAG TTA GGT CTT TGA CCA CTT AAC AAA CAG GTT ATA GTC TAC    1008
TCT ATT ACT TAC CTT GTT AAC GTC CAT AAC AAA GTC CTT AAA GAC GTT    1056
CAC TCA GTA ATA ATA GAG TCT TTA GCG AGG                            1086
```

( 2 ) INFORMATION FOR SEQ ID NO:48:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 48:

```
TTA AGG CCG TTA ATT ACG GTT TGT TAG TCG AGT CTA ATC GAT CTC CAC     48
CTT TAG ATA CAA TTG TTC AGG TCC TCT ATT CGG TCC TCA GCG CTT ACA     96
ACG TAA TTT GAG TCG TCG GTC AAG GTG TTC ACA CAA TCT GTC ATA        141
```

( 2 ) INFORMATION FOR SEQ ID NO:49:

( i ) SEQUENCE CHARACTERISTICS:
        ( A ) LENGTH: 1053 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 49:

```
GGC CCT TAA TGG GGA GTA ATA ACG AAG CTC TAT ATT GAC TCC TAT AAA     48
TCC ATG TTT TAT TTA ACT GGA ACT TAG TTA TTT AAG TTA AAC ACT TAA     96
ATT AAA TTA AAG GTC ATT TCA CTT TAT AAA AAA TGT TTT AAG CGA TAA    144
TAA GGT AAA ATT TCA TAT GTT ATC AGA TAA CTT TAC TCA TGT AAT CAA    192
TCT TTC AAT CGT GGT TTG AAA TGA CGA CTT CGA CAA TAC CGT CTA CCA    240
AGT AAG TTC TTC CAG AGG AAC TCG CTG ATG TCT CCT TTT ATG CAA CAT    288
```

| | | | | | | | | | | | | | | | |
|---|---|---|---|---|---|---|---|---|---|---|---|---|---|---|---|
|AAC|AAG|AAG|ATA|GGT|AAT|TTG|AAG|TGT|AAA|CAT|ACA|GGT|AGA|CTT|TAG|336|
|AAT|CGT|AAG|TTA|GTT|CGT|GTT|TTT|CTG|AAA|CTC|TTT|AAC|CCT|CAT|GTC|384|
|GAG|GAG|AGC|ACA|CGA|GTC|AAC|TAA|GAG|TTA|TGA|GGG|TAC|GAC|GTA|CCT|432|
|CTG|CAT|GAG|GAG|AAC|TTG|TTC|CAC|CTT|AAC|CTG|GTC|AGT|TAA|AGG|GTG|480|
|AAT|AGA|GAC|TGA|GTA|GAG|TAA|GTT|AAT|CGT|TCT|TGA|TAC|CAC|ATG|AAA|528|
|GAG|CTC|CTT|CTT|CCA|TAA|CGA|GAG|TCT|CCA|AAT|AAG|TAG|TAA|CTG|TTC|576|
|CTC|CCA|GCG|CAA|CAA|GCA|AGA|CTT|CAT|TAG|ATA|CTG|AAT|GGT|AAT|CCT|624|
|TCT|AGT|CAG|CTT|CTT|TGA|GAT|GCA|CAA|TAA|CTA|CGT|GAA|GTT|AAG|TGA|672|
|CTT|TGG|ATA|CCA|CTT|CAA|ACG|GGT|CGT|TTG|ACC|TTC|TTC|CCG|GTT|TTT|720|
|CCT|TAC|AGT|CGA|TGA|GTA|CTT|CCA|CAA|AGG|TCA|ATA|GAA|TTC|CTG|AGT|768|
|AAA|ATC|TTA|CTA|AAT|TAA|AAA|GTT|TAC|TTG|GTT|TAA|AAA|AAA|ATT|AGA|816|
|CTG|AAA|AAA|ATA|CAT|CAA|TAT|TTA|GTC|TAC|GTT|TAC|TCA|TAG|CAG|CAG|864|
|AGG|TGT|AGA|TCT|AGG|AGA|CAC|CGC|TGA|TCT|AAC|ACC|TTA|TCC|ACG|TTT|912|
|ATT|TGG|GAC|CTC|AAC|AAT|TAC|ATC|ACA|ATT|TAA|AAA|CAT|TAA|ATA|GAA|960|
|AAA|AAA|AGA|ATA|ATT|GAA|TGG|AAA|GAA|CCA|CAA|TCG|TCA|GAA|GAT|AAT|1008|
|CTT|TAG|TAA|TGA|GAA|GAA|GGT|TCC|GGC|CTT|CTT|CCA|GAG|GAA|CTC| |1053|

( 2 ) INFORMATION FOR SEQ ID NO:50:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cryptosporidium parvum ( x i ) SEQUENCE DESCRIPTION: SEQ ID NO: 50:

| | | | | | | | | | | | | | | | |
|---|---|---|---|---|---|---|---|---|---|---|---|---|---|---|---|
|CCT|GGA|ACT|TAG|TTA|TTT|AAG|TTA|AAC|ACT|TAA|ATT|AAA|TTA|AAG|GTC|48|
|ATT|TCA|CTT|TAT|AAA|AAA|TGT|TTT|AAG|TCA|TAA|TAA|GGT|AAA|ATT|TCA|96|
|TAT|GTT|ATC|AGA|TAA|CTT|TAC|TCA|TGT|AAT|CAA|TCT|TTC|AAT|CGT|GGT|144|
|TTG|AAA|TGA|CGA|CTC|GAC|AAT|ACG|TCT|ACC|AAG|TAA|GTC|TCC|AGA| |189|

What is claimed as novel and desired to be patented by Letters Patent of the United States is:

1. A hybrid vector comprising a regulatory DNA segment operably coupled to a DNA fragment encoding a polypeptide to which anti-Cryptosporidium antibodies specifically bind, wherein said sequence comprises SEQ ID NO 27 or SEQ ID NO 28.

2. The hybrid vector of claim 1, wherein said sequence further encodes a fusion protein comprising the polypeptide to which anti-cryptosporidium antibodies bind, operably coupled to another unrelated polypeptide sequence.

3. A host cell comprising the vector of claim 1.

4. A host cell comprising the vector of claim 2.

* * * * *